US010238730B2

(12) United States Patent
Sanders et al.

(10) Patent No.: US 10,238,730 B2
(45) Date of Patent: Mar. 26, 2019

(54) COLD-ADAPTED-VIRAL-ATTENUATION (CAVA) AND NOVEL ATTENUATED POLIOVIRUS STRAINS

(71) Applicant: Janssen Vaccines & Prevention B.V., Leiden (NL)

(72) Inventors: Barbara Petronella Sanders, Leiden (NL); Jerome Hubertina Henricus Victor Custers, Leiden (NL); Diana Edo-Matas, Leiden (NL); Taco Gilles Uil, Leiden (NL); John A. Lewis, Little Compton, RI (US)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 76 days.

(21) Appl. No.: 15/316,051

(22) PCT Filed: Jun. 16, 2015

(86) PCT No.: PCT/EP2015/063489
§ 371 (c)(1),
(2) Date: Dec. 2, 2016

(87) PCT Pub. No.: WO2015/193324
PCT Pub. Date: Dec. 23, 2015

(65) Prior Publication Data

US 2017/0087240 A1 Mar. 30, 2017

Related U.S. Application Data

(60) Provisional application No. 62/013,379, filed on Jun. 17, 2014.

(30) Foreign Application Priority Data

Jul. 8, 2014 (EP) .................................... 14176071

(51) Int. Cl.
*A61K 39/12* (2006.01)
*C12N 7/00* (2006.01)
*C07K 14/005* (2006.01)
*A61K 39/00* (2006.01)

(52) U.S. Cl.
CPC ............ *A61K 39/12* (2013.01); *C07K 14/005* (2013.01); *C12N 7/00* (2013.01); *A61K 2039/5252* (2013.01); *A61K 2039/5254* (2013.01); *A61K 2039/70* (2013.01); *C12N 2770/32621* (2013.01); *C12N 2770/32634* (2013.01); *C12N 2770/32664* (2013.01); *Y02A 50/466* (2018.01)

(58) Field of Classification Search
None
See application file for complete search history.

(56) References Cited

U.S. PATENT DOCUMENTS 4,525,349 A 6/1985 Montagnon et al.
8,546,123 B2 10/2013 Lewis

FOREIGN PATENT DOCUMENTS

WO 2007007344 A1 1/2007
WO 2008017870 A1 2/2008
WO 2012090000 A1 5/2012
WO 2015193324 A1 12/2015

OTHER PUBLICATIONS

Chapin et al. Science 1956 vol. 124, pp. 586-588.*
Dubes et al. Science 1956 vol. 124, pp. 586-588 (listed as Chapin on the IDS).*
Chapin et al. Cold-adapted genetic variants of polio viruses. , Science (New York, N. Y.) Sep. 28, 1956, vol. 124, No. 3222, Sep. 28, 1956 (Sep. 28, 1956), pp. 586-587, XP002733375, ISSN: 0036-8075, the whole document.
Dove et al. "Cold-adapted poliovirus mutants bypass a postentry replication block.", Journal of Virology Jun. 1997, vol. 71, No. 6, Jun. 1997 (Jun. 1997) pp. 4728-4735, XP002733377, ISSN: 0022-538X p. 4728.
International Search Report for International Application No. PCT/EP2015/063489, dated Sep. 15, 2015, 5 pages.
Database Medline [Online] US National Liberty of Medicine (NLM), Bethesda, MD, US; May 2011 (May 2011) , Verdijk Pauline et al: "Clinical development of a novel inactivated poliomyelitis vaccine based on attenuated Sabin poliovirus strains", XP002733376, Database accession No. NLM21604984 abstract & Verdijk Pauline et al: "Clinical development of a novel inactivated poliomyelitis vaccine based on attenuated Sabin poliovirus strains", Expert Review of Vaccines May 2011, vol. 10, No. 5, May 2011 (May 2011), pp. 635-644.
Written Opinion of the International Search Authority for International Application No. PCT/EP2015/063489, dated Sep. 15, 2015, year, 9 pages.

(Continued)

*Primary Examiner* — Shanon A. Foley
*Assistant Examiner* — Myron G Hill
(74) *Attorney, Agent, or Firm* — Kramer Amado, P.C.

(57) ABSTRACT

A poliovirus (PV) strain was attenuated by a novel method of Cold-Adapted-Viral-Attenuation (CAVA). The resulting recombinant attenuated PV, CAVA-PV, shows wild-type replication at 30° C., but no substantial replication at 37° C. The inability to replicate at 37° C. is defined by an inability to quantify virus during infection at this temperature by titration (infectious units), qPCR (viral RNA) or Electron Microscopy (visual signs of infection). CAVA-PV is genetically stable under production conditions and shows utility for use as the backbone to produce attenuated strains with the same antigenic profile as conventional vaccines by replacing the sequence coding for the capsid of CAVA-PV with sequences coding for capsids of different PV strains. Furthermore, mutations identified in CAVA-PV can be engineered into different, even wild-type and neurovirulent poliovirus background strains to obtain additional CAVA-PV strains.

22 Claims, 23 Drawing Sheets

Specification includes a Sequence Listing.

(56) References Cited

OTHER PUBLICATIONS

Beale et al., 1961, The D-antigen content in poliovaccine as a measure of potency, Lancet 2(7213): 1166-1168.
Bouchard et al., Determinants of attenuation and temperature sensitivity in the type 1 poliovirus Sabin vaccine, J Virol 69(8): 4972-4978.
Enders et al., 1952, Alteration in pathogenicity for monkeys of Brunhilde strain of poliomyelitis virus following cultivatior in human tissues, Fed Proc 11: 467.
Grassly et al., Immunogenicity and Effectiveness of Routine Immunization With 1 or 2 Doses of Inactivated Poliovirus Vaccine: Systematic Review and Meta-analysis, J Infect Dis.
Hawken et al., 2012, Adjuvants and inactivated polio vaccine: a systematic review, Vaccine 30(49): 6971-6979.
Heinsbroek et al., 2010 , The global introduction of inactivated polio vaccine can circumvent the oral polio vaccine paradox, Vaccine 28(22): 3778-3783.
Henderson et al., 1964, Paralytic Disease Associated with Oral Polio Vaccines, Jama 190: 41-48.
Jahan et al., 2011, A host-specific, temperature-sensitive translation defect determines the attenuation phenotype of a human rhinovirus/poliovirus chimera, PV1(RIPO), J Virol 85(14): 7225-7235.
Jiang et al., 1986, Inactivation of poliovirus with beta-propiolactone, J Biol Stand 14(2): 103-109.
John et al., 2004, A developing country perspective on vaccine-associated paralytic poliomyelitis, Bull World Health Organ 82(1): 53-57; discussion 57-58.
John et al., 2009, Role of injectable and oral polio vaccines in polio eradication, Expert Rev Vaccines 8(1): 5-8.
Koike et al., 1991, Transgenic mice susceptible to poliovirus, Proc Natl Acad Sci U S A 88(3): 951-955.
Liao et al., 2012, Safety and immunogenicity of inactivated poliovirus vaccine made from Sabin strains: a phase II, randomized, positive-controlled trial, J Infect Dis 205(2): 237-243.
Mahmood et al., 2013, Hexavalent IPV-based combination vaccines for public-sector markets of low-resource countries: A product review, Hum Vaccin Immunother 9(9).
Minor et al., 1999, Poliovirus vaccination: current understanding of poliovirus interactions in humans and implications for the eradication of poliomyelitis, Expert Rev Mol Med 1999: 1-17.
Montagnon et al., 1984, Industrial-scale production of inactivated poliovirus vaccine prepared by culture of Vero cells on microcarrier, Rev Infect Dis 6 Suppl 2: S341-344.
Okada et al., 2013, Phase II and III Clinical Studies of Diphtheria-Tetanus-Acellular Pertussis Vaccine Containing Inactivated Polio Vaccine Derived from Sabin Strains (DTaP-sIPV), J Infect Dis 208(2): 275-283.
Pfeiffer et al., 2010, Innate host barriers to viral trafficking and population diversity: lessons learned from poliovirus, Adv Virus Res 77: 85-118.
Racaniello et al., One hundred years of poliovirus pathogenesis, Virology 344(1): 9-16.
Resik et al., 2013, Priming after a fractional dose of inactivated poliovinrs vaccine, N Engl J Med 368(5): 416-424.
Sabin et al., 1956, Present status of attenuated live-virus poliomyelitis vaccine, J Am Med Assoc 162(18): 1589-1596.
Sabin et al., 1973, History of Sabin attenuated poliovirus oral live vaccine strains, Journal of Biological Standardization 1: 115-118.
Salk et al., 1953, Studies in human subjects on active immunization against poliomyelitis. I. A preliminary report of experiments in progress, J Am Med Assoc 151(13): 1081-1098.
Sanders et al., 2015, Brunenders: A partially attenuated historic poliovirus Type I vaccine strain, J Gen Virol.
Sanders et al., 2012, PER.C6((R)) cells as a serum-free suspension cell platform for the production of high titer poliovirus: a potential low cost of goods option for world supply of inactivated poliovirus vaccine, Vaccine 31(5): 850-856.
Skern et al., 1994, Picornains 2A and 3C, Methods Enzymol 244: 583-595.
Toyoda et al., 1984, Complete nucleotide sequences of all three poliovirus serotype genomes. Implication for genetic relationship, gene function and antigenic determinants, J Mol Biol 174(4): 561-585.
Van der Werf et al., Synthesis of infectious poliovirus RNA by purified T7 RNA polymerase, Proc Natl Acad Sci U S A 83(8): 2330-2334.
Van Wezel et al., 1978, New approach to the production of concentrated and purified inactivated polio and rabies tissue culture vaccines, Dev Biol Stand 41: 159-168.
Verdijk et al., 2011, Clinical development of a novel inactivated poliomyelitis vaccine based on attenuated Sabin poliovirus strains, Expert Rev Vaccines 10(5): 635-644.
Westdijk et al., 2011, Characterization and standardization of Sabin based inactivated polio vaccine: proposal for a new antigen unit for inactivated polio vaccines, Vaccine 29(18): 3390-3397.
WHO, 1988, Polio eradication by the year 2000. Rep. Resolution 41.28. W. H. Assembly, Geneva, WHO.
WHO, 2005, Cessation of routine oral polio vaccine use after global polio eradication. Framework for National Policy Makers in OPV-Using Countries, Geneva, WHO.
WHO, 2006, Inactivated poliovirus vaccine following oral poliovirus vaccine cessation, Wkly Epidemiol Rec 81(15): 137-144.
WHO (2009). WHO global action plan to minimize poliovirus facility-associated risk after eradication of wild polioviruses and cessation of routine OPV use. Geneva, WHO.
Zehrung, 2010, Improving the affordability of inactivated poliovirus vaccines (IPV) for use in low- and middle-income countries. An economic analysis of strategies to reduce the cost of routine IPV immunization PATH.

* cited by examiner

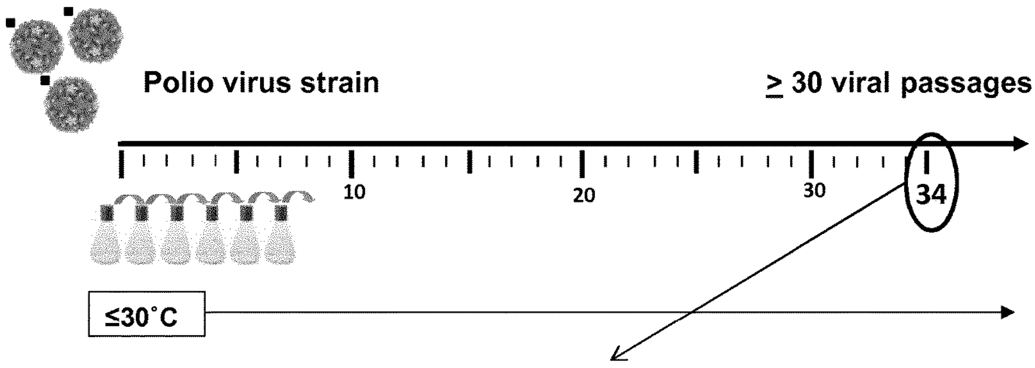
Isolating of temperature sensitive clones with *impaired* growth at 37°C:
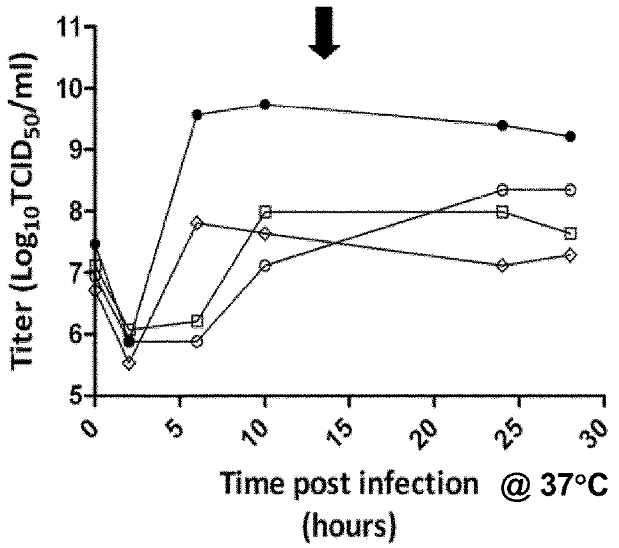
Sequencing of temperature sensitive clones and identifying mutations by comparing sequences to the original poliovirus strain
⬇
Synthesizing CAVA-PV by combining mutations from different clones into the genome of the parental poliovirus strain
⬇
Rescuing the CAVA-PV strain
Fig. 1

A
CAVA-PVMahoney
Virus Neutralization Titer (log 2)
0
2
4
6
8
10
2
4
8
16
32
64
DU/dose
B
CAVA-PVMEF-1
Virus Neutralization Titer (log 2)
0
2
4
6
8
10
12
0.5
1
2
4
8
16
DU/dose
C
CAVA-PVSaukett
Virus Neutralization Titer (log 2)
0
2
4
6
8
10
2
4
8
16
32
64
DU/dose

SEQUENCE LISTING

```
<160> NUMBER OF SEQ ID NOS: 10

<210> SEQ ID NO 1
<211> LENGTH: 7444
<212> TYPE: RNA
<213> ORGANISM: Poliovirus

<400> SEQUENCE: 1

uuaaaacagc ucugggguug uucccacccc agaggcccac guggcggcca guacaccggu      60

accacgguac ccuuguacgc cuguuuuaua cuccccuccc cguaaacuag aagcacgaaa     120

cacaaguuca auagaagggg guacagacca guaccaccac gaacaagcac uucuguuccc     180

ccggugaggu cacauagacu guccccacgg ucaaaaguga cugauccguu auccgcucac     240
```

-continued

```
guacuucgga aagccuagua ccaccuugga aucuacgaug cguugcgcuc agcacucgac    300
cccggagugu agcuuaggcu gaugagucug gacguucccc acuggugaca gugguccagg    360
cugcguuggc ggccuaccug ugguccaaaa ccacaggacg cuaguaguga acaaggugug    420
aagagcccac ugagcuaccu gagaauccuc cggccccuga augcggcuaa ucccaaccac    480
ggagcaggua aucgcaaacc agcggucagc cugucguaac gcguaagucu guggcggaac    540
cgacuacuuu ggguguccgu guuuccuuuu auuuuuaugg uggcugcuua uggugacaau    600
cauagauugu uaucauaaag caaauuggau uggccauccg gagugagcua aacuaucuau    660
uucucugagu guuggauucg uuucacccac auucugaaca aucagccuca uuaguguuac    720
ccuguuaaua agacgauauc aucacgaugg gugcucaggu uucaucacag aaagugggcg    780
cacacgaaaa cucaaauaga gcauauggug guucuaccau caauuacacc accauuaauu    840
auuauagaga uucagcuagc aaugcggcuu cgaaacagga cuucucucaa gauccaucca    900
aguucaccga gcccgucaag gacgucuuga uaaagacagc cccaaugcua aacucgccaa    960
acauagaggc uugcggguau agcgauagag uccugcaauu aacacuggga aacuccacua   1020
uaaccacaca ggaagcggcu aauucaauag ucgcuuaugg gcguuggccu gaguaccuga   1080
gagacagcga agccaaucca guggaucaac cgacagaacc agacgucgcu gcauguaggu   1140
uuuauacacu agacaccgug ucuuggacga aagagucgcg agggugguggg uggaaguugc   1200
cugaugcacu gagggacaug ggacuguuug ggcaaaauuu guacuaccac uaccuaggua   1260
gguccgggua cacuguacau guacagugua acgccuccaa auuccaccag ggagcgcuug   1320
ggguauucgc cguaccagag augugcuugg ccggggacag uaacaccacu accacacaca   1380
ccagcuauca aaaugccaau ccuggcgaga aaggaggcac uuucacaggu acguucaccc   1440
cugacaacaa ccagacaucg ccugcccgca gguuuugccc gguggauuac cuuuuuggaa   1500
acggcacauu guuggggaac gccuuugugu ucccgcacca gauaauaaac uuacggacca   1560
auaacugugc cacauuggug cucccuuacg ugaacucccu cucgauagau aguaugguga   1620
agcacaauaa uuggggaauc gcaauaguac cauuggcccc auuaaauuuu gcuaaugagu   1680
ccuccccaga aauuccaauc accuuaacca uagccccuau gugcugugag uucaauggau   1740
uaagaaacau uacccugcca cguuuacagg gccugccggu caugaacacc ccugguagua   1800
aucaauaucu uacugcagac aacuuccagu caccgugugc gcugccugaa uuugacguaa   1860
ccccaccuau ugacauaccc ggugaaguua agaacaugau ggaauuggcu gaaauugaca   1920
ccaugauucc cuuugacuua agugccacga aaaagaacac cauggaaaug uauaggguuc   1980
gguuaaguga caaaccacac acagacgacc ccauacucug ucugucgcuu ucuccagcuu   2040
cagauccuag guugucacau accaugcuag gagaaauccu aaauuacuac acacacuggg   2100
caggaucccu gaaguucacg uuucuguucu gugggguccau gauggcaacu ggcaaacugu   2160
uggugucaua cgcgccuccu ggagccgacc caccaaagaa gcguaaggag gcaauguugg   2220
gaacacaugu gaucugggac auaggacugc aauccucaug cacuauggua guaccaugga   2280
uaagcaacac cacguaccgg cagaccauug augauaguuu caccgaaggc ggauacauca   2340
gcgucuucua ccaaaccaga auaguggugc cccuuucgac gcccagggag auggacaucc   2400
uugguuuugu gucagcgugu aaugacuuca gugugcgcuu guugcgagac acuacacaca   2460
uagagcaaaa agcgcuagca cagggguuag gucagaugcu ugaaagcaug auugacaaca   2520
caguccguga gacgaugggg gcggcaacgu cuagagacgc ucucccaaac accgaagcca   2580
```

-continued guggaccggc acacuccaag gaaaucccgg cacucaccgc aguggaaacu ggggcuacaa 2640
auccacuagu cccuucugac acagugcaaa ccagacaugu uauacaacac aggucuaggu 2700
cagagucuag cauagagucu uucuucgcgc ggggcgcaug cgugaccauc augacuguag 2760
acaacucagc uuccaccaca aacaaggaca agcuauuuuc aguguggaaa aucacguaua 2820
aagacacugu ucaguuacgg aggaaauugg aguuuuucac cuauucuaga uuugauaugg 2880
aauuuaccuu uguagucacu gcaaauuuca cugagacuaa caaugggcau gcuuuaaauc 2940
agguguacca aauuauguac guaccaccag gcgcuccagu gccugagaaa ugggacgacu 3000
acacauggca aaccucauca aacccaucaa uuuuuuacac cuacggaaca gcuccagccc 3060
ggaucucggu accguauguu gguauuucga acgccuauuc acacuuuuac gacgguuuuu 3120
cuaaaguacc acugaaggac cagucggcag cacuaggcga cucccucuau gguguagcau 3180
cucuaaacga uuucgguauu uuggcuguua gaguagucaa ugaucacaac ccgaccaaag 3240
ucaccuccaa agucagagug uaucuaaaac ccaagcacau cagagucugg ugcccgcguc 3300
caccgagggc aguggcguac uacggcccug gaguggauua caaggauggu acgcucacac 3360
cccuuuccac caaggaacug accacauaug gauucggaca ccaaaacaaa gcgguguaca 3420
cugcagguua uaaaauuugc aacuaccauu uggccacuca ggaggauuug caaaacgcag 3480
ugaaugucau guggaacaga gaucuuuuag uuacagaauc aaaagcccag gguacggacu 3540
cgauugccag gugcaguugu aaugcaggag uguauuacug cgaguccaga aggaaauacu 3600
acccaaucuc cuucgucggc cccacuuucc aguauaugga ggccaacgac uacuacccag 3660
cuagauacca aucccauaug uugauugggc auggcuuugc uucgcccggc gauuguggug 3720
guauccucag gugucaacau ggugucauug ggauugugac agcuggugga gaggguuugg 3780
ucgcguucuc ugacauaagg gaccuauaug cuuaugagga ggaagcuaug gagcagggca 3840
uuacaaauua cauugaguca cuuggcgcug cauucgguag cgggguucacc cagcaaauag 3900
gggauaagau aucagaacua acuagcaugg uaaccagcac aaucacagag aaacuacuaa 3960
aaaaucuaau caaaauuauu ucaucucugg ugauaaucac cagaaauuau gaagacacua 4020
ccacagugcu ugccacuuua gcucuccuug ggugugacgu uucaccgugg cagugguuga 4080
agaagaaggc augugacauc uuggagauuc ccuauguuau uaaacagggu gauaguuggu 4140
uaaagaaauu cacugaggca uguaacgcag ccaagggguu ggagugggug uccaacaaaa 4200
uuucaaaauu caucgacugg cugaaggaga gaaucauccc acaagccagg gacaagcuug 4260
aauuuguaac caaauugaaa caguuggaaa ugcuugagaa ucaaauaucc acaauacacc 4320
aguccugccc aagucaggaa caccaggaag uuuuauucaa caauguacgc ugguugucca 4380
uccaaucuaa aagauucgcu ccauuauacg cgcucgaagc caagagaaua caaaagcugg 4440
aacacaccau uaauaacuac auacaguuca agagcaaaca ccguauugaa ccaguauguu 4500
uguuggugca ugggagccca ggcacaggga aaucaguugc gaccaaucug auugcuaggg 4560
ccauagcuga gaaagagaac accuccacuu acucacuacc accagauccg ucucacuuug 4620
augguuauaa acaacaaggc gugguuauua uggaugaccu gaaccaaaac ccagacgggg 4680
cagacaugaa gcucuucugu caaaauggugu ccacugugga guuuauccca ccuauggccu 4740
cacuggaaga aaagggcauu uuguucacau ccaacuaugu cuuagccucu accaacucca 4800
gucguaucac accacccaca guagcucaca gugacgcgcu ggcccggaga uuugcuuuug 4860
auauggacau acaggugaug ggcgaauacu ccagagaugg uaaacucaau auggcaaugg 4920
cuacagaaau gugcaagaac ugccaccaac cggcaaacuu uaaaagaugc uguccuuuag 4980

-continued ugugugcaa ggcaauucaa uuaauggaca aaucuucuag aguuagauac aguauugauc 5040
agaucacuac aaugauuauc aaugagagaa acagaagauc caacauuggu aauugcaugg 5100
aggcuuuguu ccaaggacca cuccaauaca aagacuugaa aauugauauc aagacgaguc 5160
ccccuccuga auguauuaau gauuugcucc aagcaguuga cucccaggaa gugagggauu 5220
auugcgaaaa gaaagguugg aucgucaaua uuacuaguca agugcaaaca gagagaaaca 5280
ucaaucgagc aaugaccauc uugcaagcag uaacaacuuu ugcugcagug gcugguqucg 5340 uguauguuau guacaaguua uucgcuggac accagggagc auacacuggu cuaccaaaca 5400
aaagacccaa ugugccuacc auuagaacag caaaagugca aggaccuggg uuugacuacg 5460
caguggcuau ggcuaaaaga aacauuguua cagcaacuac uaguaaagga gaguucacaa 5520 ugcuggggu ucaugacaac guggccauuu uaccaacuca ugccucaccu ggugagagua 5580
uugugauuga uggcaaagag guugagauuc uggacgcuaa agcccucgaa gaccaggcag 5640
guacuaaucu ggaaaucacc auaauaaccc ucaaaagaaa ugaaaaauuc agagauauca 5700
gaccacauau acccacucaa aucaccgaga cgaaugaugg aguucugauu gugaacacua 5760
guaaguaccc caauauguau guuccugucg gugcugugac ugagcaggga uaucuaaauc 5820
ucgguggacg ccaaaccgcu cguacuuuaa uguacaacuu uccaaccaga gcagggcagu 5880
gugguggagu caucacaugu acugggaagg ucaucgggau gcauguuggu gggaacgguu 5940
cacacggguu ugcagcggcc cugaagcgau cauacuucac ucagagucaa ggugaaauuc 6000
aguggaugag accaucgaag gaagugggau acccaauuau aaacgccccg uccaaaacca 6060
agcuugaacc cagugcuuuu cacuauguau uugaaggagu gaaggaacca gcaguccuua 6120
ccaaaaacga ucccaggcuu aaaacagacu uugaggaggc aauuuucucc aaguacgugg 6180
gcaacaagau cacugaagug gaugaguaca ugaaagaggc aguagaccac uaugcuggcc 6240
aacucauguc acuagacauu gacacagaac agauguguuu ggaggaugcc auguauggca 6300 cugaugguou ggaagcacuu gauuuaucca ccagugcugg cuacccuuau guaacaaugg 6360
gaaagaagaa aagagauauu uuaaacaaac aaaccaggga caccaaggaa augcaaaaac 6420
ucuuagauac uuauggaauc aauuuaccgu uaguaacgua ugucaaagau gagcuaaggu 6480
cuaaaaccaa aguggagcag ggaaaaucca gauugauuga agccuccagc uuaaaugauu 6540
caguagcuau gagaauggca uuuggaaauc ucuaugcagc auuccauaaa aacccaggag 6600
uuauuacugg cagugcaguu gguugugacc cagaucuguu cuggagcaag auuccaguac 6660
ugauggaaga aaagcuuuuc gccuuugacu auacaggcua ugaugcauca cucagcccag 6720
cuugguuuga ggcacucaaa augguauugg agaaaauugg auucggggac agaguggacu 6780
acauugacua ccucaaucau ucacaccacu uguacaagaa caaaacauac ugugucaagg 6840
gcggcaugcc aucuggcugc ucuggcaccu caaucuucaa cucgaugauc aacaaucuga 6900
ucauuaggac gcuuuugcua aaaaccuaca agggcauaga cuuagaccac cuaaaaauga 6960
uugccuaugg ugaugaugua aucgcuuccu acccccauga gguugacgcu agucuccuag 7020
cccaaucagg aaaagacuau ggacuaacua ugacuccagc agauaaaucu gccacuuuug 7080
aaacagucac augggagaau guaacauuuu ugaaaagauu cuucagagca gacgagaagu 7140
auccauuucu uauucaucca guaaugccaa ugaaggaaau ucaugaauca aucagaugga 7200
ccaaggaucc uagaaacaca caggaucacg uacgcucuuu gugcuuauug gcuuggcaca 7260
auggagaaga agaauacaac aaguuccuag cuaaaauuag gagcgugcca auuggaagag 7320

-continued

```
ccuugcugcu cccagaguac ucaacauugu accgacguug gcucgacucg uuuuaguaac   7380

ccuaccucag ucgaauugga uugggucaua cuguuguagg gguaaauuuu ucuuuaauuc   7440

gggg                                                                7444


<210> SEQ ID NO 2
<211> LENGTH: 881
<212> TYPE: PRT
<213> ORGANISM: Poliovirus

<400> SEQUENCE: 2

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Arg Asp Ser Ala Ser Asn Ala Ala Ser Lys Gln Asp Phe Ser Gln
        35                  40                  45

Asp Pro Ser Lys Phe Thr Glu Pro Ile Lys Asp Val Leu Ile Lys Thr
    50                  55                  60

Ala Pro Met Leu Asn Ser Pro Asn Ile Glu Ala Cys Gly Tyr Ser Asp
65                  70                  75                  80

Arg Val Leu Gln Leu Thr Leu Gly Asn Ser Thr Ile Thr Thr Gln Glu
                85                  90                  95

Ala Ala Asn Ser Val Val Ala Tyr Gly Arg Trp Pro Glu Tyr Leu Arg
            100                 105                 110

Asp Ser Glu Ala Asn Pro Val Asp Gln Pro Thr Glu Pro Asp Val Ala
        115                 120                 125

Ala Cys Arg Phe Tyr Thr Leu Asp Thr Val Ser Trp Thr Lys Glu Ser
    130                 135                 140

Arg Gly Trp Trp Trp Lys Leu Pro Asp Ala Leu Arg Asp Met Gly Leu
145                 150                 155                 160

Phe Gly Gln Asn Met Tyr Tyr His Tyr Leu Gly Arg Ser Gly Tyr Thr
                165                 170                 175

Val His Val Gln Cys Asn Ala Ser Lys Phe His Gln Gly Ala Leu Gly
            180                 185                 190

Val Phe Ala Val Pro Glu Met Cys Leu Ala Gly Asp Ser Asn Thr Thr
        195                 200                 205

Thr Met His Thr Ser Tyr Gln Asn Ala Asn Pro Gly Glu Lys Gly Gly
    210                 215                 220

Thr Phe Thr Gly Thr Phe Thr Pro Asp Asn Asn Gln Thr Ser Pro Ala
225                 230                 235                 240

Arg Arg Phe Cys Pro Val Asp Tyr Leu Leu Gly Asn Gly Thr Leu Leu
                245                 250                 255

Gly Asn Ala Phe Val Phe Pro His Gln Ile Ile Asn Leu Arg Thr Asn
            260                 265                 270

Asn Cys Ala Thr Leu Val Leu Pro Tyr Val Asn Ser Leu Ser Ile Asp
        275                 280                 285

Ser Met Val Lys His Asn Asn Trp Gly Ile Ala Ile Leu Pro Leu Ala
    290                 295                 300

Pro Leu Asn Phe Ala Ser Glu Ser Ser Pro Glu Ile Pro Ile Thr Leu
305                 310                 315                 320

Thr Ile Ala Pro Met Cys Cys Glu Phe Asn Gly Leu Arg Asn Ile Thr
                325                 330                 335

Leu Pro Arg Leu Gln Gly Leu Pro Val Met Asn Thr Pro Gly Ser Asn
            340                 345                 350
```

-continued

```
Gln Tyr Leu Thr Ala Asp Asn Phe Gln Ser Pro Cys Ala Leu Pro Glu
        355                 360                 365

Phe Asp Val Thr Pro Pro Ile Asp Ile Pro Gly Glu Val Lys Asn Met
    370                 375                 380

Met Glu Leu Ala Glu Ile Asp Thr Met Ile Pro Phe Asp Leu Ser Ala
385                 390                 395                 400

Thr Lys Lys Asn Thr Met Glu Met Tyr Arg Val Arg Leu Ser Asp Lys
                405                 410                 415

Pro His Thr Asp Asp Pro Ile Leu Cys Leu Ser Leu Ser Pro Ala Ser
            420                 425                 430

Asp Pro Arg Leu Ser His Thr Met Leu Gly Glu Ile Leu Asn Tyr Tyr
        435                 440                 445

Thr His Trp Ala Gly Ser Leu Lys Phe Thr Phe Leu Phe Cys Gly Ser
    450                 455                 460

Met Met Ala Thr Gly Lys Leu Leu Val Ser Tyr Ala Pro Pro Gly Ala
465                 470                 475                 480

Asp Pro Pro Lys Lys Arg Lys Glu Ala Met Leu Gly Thr His Val Ile
                485                 490                 495

Trp Asp Ile Gly Leu Gln Ser Ser Cys Thr Met Val Val Pro Trp Ile
            500                 505                 510

Ser Asn Thr Thr Tyr Arg Gln Thr Ile Asp Asp Ser Phe Thr Glu Gly
        515                 520                 525

Gly Tyr Ile Ser Val Phe Tyr Gln Thr Arg Ile Val Val Pro Leu Ser
    530                 535                 540

Thr Pro Arg Glu Met Asp Ile Leu Gly Phe Val Ser Ala Cys Asn Asp
545                 550                 555                 560

Phe Ser Val Arg Leu Leu Arg Asp Thr Thr His Ile Glu Gln Lys Ala
                565                 570                 575

Leu Ala Gln Gly Leu Gly Gln Met Leu Glu Ser Met Ile Asp Asn Thr
            580                 585                 590

Val Arg Glu Thr Val Gly Ala Ala Thr Ser Arg Asp Ala Leu Pro Asn
        595                 600                 605

Thr Glu Ala Ser Gly Pro Thr His Ser Lys Glu Ile Pro Ala Leu Thr
    610                 615                 620

Ala Val Glu Thr Gly Ala Thr Asn Pro Leu Val Pro Ser Asp Thr Val
625                 630                 635                 640

Gln Thr Arg His Val Val Gln His Arg Ser Arg Ser Glu Ser Ser Ile
                645                 650                 655

Glu Ser Phe Phe Ala Arg Gly Ala Cys Val Thr Ile Met Thr Val Asp
            660                 665                 670

Asn Pro Ala Ser Thr Thr Asn Lys Asp Lys Leu Phe Ala Val Trp Lys
        675                 680                 685

Ile Thr Tyr Lys Asp Thr Val Gln Leu Arg Arg Lys Leu Glu Phe Phe
    690                 695                 700

Thr Tyr Ser Arg Phe Asp Met Glu Leu Thr Phe Val Val Thr Ala Asn
705                 710                 715                 720

Phe Thr Glu Thr Asn Asn Gly His Ala Leu Asn Gln Val Tyr Gln Ile
                725                 730                 735

Met Tyr Val Pro Pro Gly Ala Pro Val Pro Glu Lys Trp Asp Asp Tyr
            740                 745                 750

Thr Trp Gln Thr Ser Ser Asn Pro Ser Ile Phe Tyr Thr Tyr Gly Thr
        755                 760                 765
```

```
Ala Pro Ala Arg Ile Ser Val Pro Tyr Val Gly Ile Ser Asn Ala Tyr
    770                 775                 780

Ser His Phe Tyr Asp Gly Phe Ser Lys Val Pro Leu Lys Asp Gln Ser
785                 790                 795                 800

Ala Ala Leu Gly Asp Ser Leu Tyr Gly Ala Ala Ser Leu Asn Asp Phe
                805                 810                 815

Gly Ile Leu Ala Val Arg Val Val Asn Asp His Asn Pro Thr Lys Val
            820                 825                 830

Thr Ser Lys Ile Arg Val Tyr Leu Lys Pro Lys His Ile Arg Val Trp
        835                 840                 845

Cys Pro Arg Pro Pro Arg Ala Val Ala Tyr Tyr Gly Pro Gly Val Asp
    850                 855                 860

Tyr Lys Asp Gly Thr Leu Thr Pro Leu Ser Thr Lys Asp Leu Thr Thr
865                 870                 875                 880

Tyr


<210> SEQ ID NO 3
<211> LENGTH: 879
<212> TYPE: PRT
<213> ORGANISM: Poliovirus

<400> SEQUENCE: 3

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Arg Asp Ser Ala Ser Asn Ala Ala Ser Lys Gln Asp Phe Ala Gln
        35                  40                  45

Asp Pro Ser Lys Phe Thr Glu Pro Ile Lys Asp Val Leu Ile Lys Thr
    50                  55                  60

Ala Pro Thr Leu Asn Ser Pro Asn Ile Glu Ala Cys Gly Tyr Ser Asp
65                  70                  75                  80

Arg Val Met Gln Leu Thr Leu Gly Asn Ser Thr Ile Thr Thr Gln Glu
                85                  90                  95

Ala Ala Asn Ser Val Val Ala Tyr Gly Arg Trp Pro Glu Tyr Ile Lys
            100                 105                 110

Asp Ser Glu Ala Asn Pro Val Asp Gln Pro Thr Glu Pro Asp Val Ala
        115                 120                 125

Ala Cys Arg Phe Tyr Thr Leu Asp Thr Val Thr Trp Arg Lys Glu Ser
    130                 135                 140

Arg Gly Trp Trp Trp Lys Leu Pro Asp Ala Leu Lys Asp Met Gly Leu
145                 150                 155                 160

Phe Gly Gln Asn Met Phe Tyr His Tyr Leu Gly Arg Ala Gly Tyr Thr
                165                 170                 175

Val His Val Gln Cys Asn Ala Ser Lys Phe His Gln Gly Ala Leu Gly
            180                 185                 190

Val Phe Ala Val Pro Glu Met Cys Leu Ala Gly Asp Ser Thr Thr His
        195                 200                 205

Met Phe Thr Lys Tyr Glu Asn Ala Asn Pro Gly Glu Lys Gly Gly Glu
    210                 215                 220

Phe Lys Gly Ser Phe Thr Leu Asp Thr Asn Ala Thr Asn Pro Ala Arg
225                 230                 235                 240

Asn Phe Cys Pro Val Asp Tyr Leu Phe Gly Ser Gly Val Leu Ala Gly
                245                 250                 255
```

-continued

```
Asn Ala Phe Val Tyr Pro His Gln Ile Ile Asn Leu Arg Thr Asn Asn
            260                 265                 270

Cys Ala Thr Leu Val Leu Pro Tyr Val Asn Ser Leu Ser Ile Asp Ser
        275                 280                 285

Met Thr Lys His Asn Asn Trp Gly Ile Ala Ile Leu Pro Leu Ala Pro
    290                 295                 300

Leu Asp Phe Ala Thr Glu Ser Ser Thr Glu Ile Pro Ile Thr Leu Thr
305                 310                 315                 320

Ile Ala Pro Met Cys Cys Glu Phe Asn Gly Leu Arg Asn Ile Thr Val
                325                 330                 335

Pro Arg Thr Gln Gly Leu Pro Val Leu Asn Thr Pro Gly Ser Asn Gln
            340                 345                 350

Tyr Leu Thr Ala Asp Asn Tyr Gln Ser Pro Cys Ala Ile Pro Glu Phe
        355                 360                 365

Asp Val Thr Pro Pro Ile Asp Ile Pro Gly Glu Val Arg Asn Met Met
    370                 375                 380

Glu Leu Ala Glu Ile Asp Thr Met Ile Pro Leu Asn Leu Thr Asn Gln
385                 390                 395                 400

Arg Lys Asn Thr Met Asp Met Tyr Arg Val Glu Leu Asn Asp Ala Ala
                405                 410                 415

His Ser Asp Thr Pro Ile Leu Cys Leu Ser Leu Ser Pro Ala Ser Asp
            420                 425                 430

Pro Arg Leu Ala His Thr Met Leu Gly Glu Ile Leu Asn Tyr Tyr Thr
        435                 440                 445

His Trp Ala Gly Ser Leu Lys Phe Thr Phe Leu Phe Cys Gly Ser Met
    450                 455                 460

Met Ala Thr Gly Lys Leu Leu Val Ser Tyr Ala Pro Pro Gly Ala Glu
465                 470                 475                 480

Ala Pro Lys Ser Arg Lys Glu Ala Met Leu Gly Thr His Val Ile Trp
                485                 490                 495

Asp Ile Gly Leu Gln Ser Ser Cys Thr Met Val Val Pro Trp Ile Ser
            500                 505                 510

Asn Thr Thr Tyr Arg Gln Thr Ile Asn Asp Ser Phe Thr Glu Gly Gly
        515                 520                 525

Tyr Ile Ser Met Phe Tyr Gln Thr Arg Val Val Val Pro Leu Ser Thr
    530                 535                 540

Pro Arg Lys Met Asp Ile Leu Gly Phe Val Ser Ala Cys Asn Asp Phe
545                 550                 555                 560

Ser Val Arg Leu Leu Arg Asp Thr Thr His Ile Ser Gln Glu Ala Met
                565                 570                 575

Pro Gln Gly Leu Gly Asp Leu Ile Glu Gly Val Val Glu Gly Val Thr
            580                 585                 590

Arg Asn Ala Leu Thr Pro Leu Thr Pro Ala Asn Asn Leu Pro Asp Thr
        595                 600                 605

Gln Ser Ser Gly Pro Ala His Ser Lys Glu Thr Pro Ala Leu Thr Ala
    610                 615                 620

Val Glu Thr Gly Ala Thr Asn Pro Leu Val Pro Ser Asp Thr Val Gln
625                 630                 635                 640

Thr Arg His Val Ile Gln Lys Arg Thr Arg Ser Glu Ser Thr Val Glu
                645                 650                 655

Ser Phe Phe Ala Arg Gly Ala Cys Val Ala Ile Ile Glu Val Asp Asn
            660                 665                 670

Asp Ala Pro Thr Lys Arg Ala Ser Lys Leu Phe Ser Val Trp Lys Ile
```

```
        675                 680                 685

Thr Tyr Lys Asp Thr Val Gln Leu Arg Arg Lys Leu Glu Phe Phe Thr
    690                 695                 700

Tyr Ser Arg Phe Asp Met Glu Phe Thr Phe Val Val Thr Ser Asn Tyr
705                 710                 715                 720

Thr Asp Ala Asn Asn Gly His Ala Leu Asn Gln Val Tyr Gln Ile Met
                725                 730                 735

Tyr Ile Pro Pro Gly Ala Pro Ile Pro Gly Lys Trp Asn Asp Tyr Thr
            740                 745                 750

Trp Gln Thr Ser Ser Asn Pro Ser Val Phe Tyr Thr Tyr Gly Ala Pro
        755                 760                 765

Pro Ala Arg Ile Ser Val Pro Tyr Val Gly Ile Ala Asn Ala Tyr Ser
    770                 775                 780

His Phe Tyr Asp Gly Phe Ala Lys Val Pro Leu Ala Gly Gln Ala Ser
785                 790                 795                 800

Thr Glu Gly Asp Ser Leu Tyr Gly Ala Ala Ser Leu Asn Asp Phe Gly
                805                 810                 815

Ser Leu Ala Val Arg Val Val Asn Asp His Asn Pro Thr Lys Leu Thr
            820                 825                 830

Ser Lys Ile Arg Val Tyr Met Lys Pro Lys His Val Arg Val Trp Cys
        835                 840                 845

Pro Arg Pro Pro Arg Ala Val Pro Tyr Tyr Gly Pro Gly Val Asp Tyr
    850                 855                 860

Lys Asp Gly Leu Ala Pro Leu Pro Gly Lys Gly Leu Thr Thr Tyr
865                 870                 875


<210> SEQ ID NO 4
<211> LENGTH: 878
<212> TYPE: PRT
<213> ORGANISM: Poliovirus

<400> SEQUENCE: 4

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Lys Asp Ser Ala Ser Asn Ala Ala Ser Lys Gln Asp Tyr Ser Gln
        35                  40                  45

Asp Pro Ser Lys Phe Thr Glu Pro Leu Lys Asp Val Leu Ile Lys Thr
    50                  55                  60

Ala Pro Thr Leu Asn Ser Pro Asn Val Glu Ala Cys Gly Tyr Ser Asp
65                  70                  75                  80

Arg Val Leu Gln Leu Thr Leu Gly Asn Ser Thr Ile Thr Thr Gln Glu
                85                  90                  95

Ala Ala Asn Ser Val Val Ala Tyr Gly Arg Trp Pro Glu Phe Ile Arg
            100                 105                 110

Asp Asp Glu Ala Asn Pro Val Asp Gln Pro Thr Glu Pro Asp Val Ala
        115                 120                 125

Thr Cys Arg Phe Tyr Thr Leu Asp Thr Val Met Trp Gly Lys Glu Ser
    130                 135                 140

Lys Gly Trp Trp Trp Lys Leu Pro Asp Ala Leu Arg Asp Met Gly Leu
145                 150                 155                 160

Phe Gly Gln Asn Met Tyr Tyr His Tyr Leu Gly Arg Ser Gly Tyr Thr
                165                 170                 175
```

-continued

```
Val His Val Gln Cys Asn Ala Ser Lys Phe His Gln Gly Ala Leu Gly
            180                 185                 190

Val Phe Ala Ile Pro Glu Tyr Cys Leu Ala Gly Asp Ser Asp Lys Gln
        195                 200                 205

Arg Tyr Thr Ser Tyr Ala Asn Ala Asn Pro Gly Glu Lys Gly Gly Lys
    210                 215                 220

Phe Tyr Ser Gln Phe Asn Arg Asp Thr Ala Val Thr Ser Pro Lys Arg
225                 230                 235                 240

Glu Phe Cys Pro Val Asp Tyr Leu Leu Gly Cys Gly Val Leu Leu Gly
                245                 250                 255

Asn Ala Phe Val Tyr Pro His Gln Ile Ile Asn Leu Arg Thr Asn Asn
            260                 265                 270

Ser Ala Thr Ile Val Leu Pro Tyr Val Asn Ala Leu Ala Ile Asp Ser
        275                 280                 285

Met Val Lys His Asn Asn Trp Gly Ile Ala Ile Leu Pro Leu Ser Pro
    290                 295                 300

Leu Asp Phe Ala Gln Asp Ser Ser Val Glu Ile Pro Ile Thr Val Thr
305                 310                 315                 320

Ile Ala Pro Met Cys Ser Glu Phe Asn Gly Leu Arg Asn Val Thr Ala
                325                 330                 335

Pro Lys Phe Gln Gly Leu Pro Val Leu Asn Thr Pro Gly Ser Asn Gln
            340                 345                 350

Tyr Leu Thr Ser Asp Asn His Gln Ser Pro Cys Ala Ile Pro Glu Phe
        355                 360                 365

Asp Val Thr Pro Pro Ile Asp Ile Pro Gly Glu Val Lys Asn Met Met
    370                 375                 380

Glu Leu Ala Glu Ile Asp Thr Met Ile Pro Leu Asn Leu Glu Asn Thr
385                 390                 395                 400

Lys Arg Asn Thr Met Asp Met Tyr Arg Val Thr Leu Ser Asp Ser Ala
                405                 410                 415

Asp Leu Ser Gln Pro Ile Leu Cys Leu Ser Leu Ser Pro Ala Ser Asp
            420                 425                 430

Pro Arg Leu Ser His Thr Met Leu Gly Glu Val Leu Asn Tyr Tyr Thr
        435                 440                 445

His Trp Ala Gly Ser Leu Lys Phe Thr Phe Leu Phe Cys Gly Ser Met
    450                 455                 460

Met Ala Thr Gly Lys Ile Leu Val Ala Tyr Ala Pro Pro Gly Ala Gln
465                 470                 475                 480

Pro Pro Thr Ser Arg Lys Glu Ala Met Leu Gly Thr His Val Ile Trp
                485                 490                 495

Asp Leu Gly Leu Gln Ser Ser Cys Thr Met Val Val Pro Trp Ile Ser
            500                 505                 510

Asn Val Thr Tyr Arg Gln Thr Thr Gln Asp Ser Phe Thr Glu Gly Gly
        515                 520                 525

Tyr Ile Ser Met Phe Tyr Gln Thr Arg Ile Val Val Pro Leu Ser Thr
    530                 535                 540

Pro Lys Ser Met Ser Met Leu Gly Phe Val Ser Ala Cys Asn Asp Phe
545                 550                 555                 560

Ser Val Arg Leu Leu Arg Asp Thr Thr His Ile Ser Gln Ser Ala Leu
                565                 570                 575

Pro Gln Gly Ile Glu Asp Leu Ile Thr Glu Val Ala Gln Gly Ala Leu
            580                 585                 590

Thr Leu Ser Leu Pro Lys Gln Gln Asp Ser Leu Pro Asp Thr Lys Ala
```

```
        595                 600                 605

Ser Gly Pro Ala His Ser Lys Glu Val Pro Ala Leu Thr Ala Val Glu
    610                 615                 620

Thr Gly Ala Thr Asn Pro Leu Val Pro Ser Asp Thr Val Gln Thr Arg
625                 630                 635                 640

His Val Ile Gln Arg Arg Ser Arg Ser Glu Ser Thr Ile Glu Ser Phe
                645                 650                 655

Phe Ala Arg Gly Ala Cys Val Ala Ile Ile Glu Val Asp Asn Glu Glu
            660                 665                 670

Pro Thr Thr Arg Ala Gln Lys Leu Phe Ala Thr Trp Arg Ile Thr Tyr
        675                 680                 685

Lys Asp Thr Val Gln Leu Arg Arg Lys Leu Glu Phe Phe Thr Tyr Ser
    690                 695                 700

Arg Phe Asp Met Glu Phe Thr Phe Val Val Thr Ala Asn Phe Thr Asn
705                 710                 715                 720

Thr Asn Asn Gly His Ala Leu Asn Gln Val Tyr Gln Ile Met Tyr Ile
                725                 730                 735

Pro Pro Gly Ala Pro Thr Pro Lys Ser Trp Asp Asp Tyr Thr Trp Gln
            740                 745                 750

Thr Ser Ser Asn Pro Ser Ile Phe Tyr Thr Tyr Gly Ala Ala Pro Ala
        755                 760                 765

Arg Ile Ser Val Pro Tyr Val Gly Leu Ala Asn Ala Tyr Ser His Phe
    770                 775                 780

Tyr Asp Gly Phe Ala Lys Val Pro Leu Lys Thr Asp Ala Asn Asp Gln
785                 790                 795                 800

Ile Gly Asp Ser Leu Tyr Ser Ala Met Thr Val Asp Asp Phe Gly Val
                805                 810                 815

Leu Ala Ile Arg Val Val Asn Asp His Asn Pro Thr Lys Val Thr Ser
            820                 825                 830

Lys Val Arg Ile Tyr Met Lys Pro Lys His Val Arg Val Trp Cys Pro
        835                 840                 845

Arg Pro Pro Arg Ala Val Pro Tyr Tyr Gly Pro Gly Val Asp Tyr Lys
    850                 855                 860

Asp Asn Leu Asn Pro Leu Ser Glu Lys Gly Leu Thr Thr Tyr
865                 870                 875


<210> SEQ ID NO 5
<211> LENGTH: 7502
<212> TYPE: RNA
<213> ORGANISM: Poliovirus

<400> SEQUENCE: 5

uuaaaacagc ucugggguug uucccacccc agaggcccac guggcggcca guacacuggu      60

auugcgguac cuuuguacgc cuguuuuaua cuccccuuccc ccguaacuua gaagcacaau    120

guccaaguuc aauaggaggg gguacaaacc aguaccacca cgaacaagca cuucuguucc    180

cccggugagg cuguauaggc uguuuccacg gcuaaaagcg gcugauccgu uauccgcuca    240

uguacuucga gaagccuagu aucaccuugg aaucuucgau gcguugcgcu caacacucaa    300

ccccagagug uagcuuaggu cgaugagucu ggacguuccu caccggcgac gguggucag     360

gcugcguugg cggccuaccu guggcccaaa gccacaggac gcuaguugug aacaaggugu    420

gaagagccua uugagcuacc ugagaguccu ccggccccug aaugcggcua auccuaacca    480

cggagcaggc aguggcaauc cagcgaccag ccugucguaa cgcgcaaguu cguggcggaa    540
```

-continued

```
ccgacuacuu ugggugucog uguuuccuuu uauuuuuaca auggcugcuu auggugacaa    600
ucauugauug uuaucauaaa gcaaauugga uuggccaucc ggugagaauu ugauuauuaa    660
auuacucucu uguugggauu gcuccuuuga aauccugugc acucacaccu auuggaauua    720
ccucauuguu aagauaucau caccacuaug ggcgcccaag ucucaucaca gaaaguugga    780
gcccaugaga auucaaacag agcuuauggc ggauccacca uuaauuacac uacuauuaau    840
uauuacaggg auucugcgag caaugccgcu aguaagcagg acuuugcaca agacccaucc    900
aaguucacug aaccuauuaa agauguucuc auuaagaccg cucccacgcu aaacucuccu    960
aauaucgagg cgugugggua uagcgacaga gugaugcaac uaacccuagg caauuccacc   1020
auuaccacac aggaggcggc caauucuguc guugcauacg gccgguggcc cgaguacauc   1080
aaggacucag aagcaaaucc uguggaccag ccaacugaac cggacguugc cgcgugcagg   1140
uuuuacacac uagacacugu uacuuggcgc aaggagucca gagggguggug guggaaacug   1200
ccugaugcac uaaaggacau gggauuauuc ggccagaaca uguucuacca cuaccucggg   1260
agggcuggcu auacugugca cguacagugu aaugcuucaa aguuucacca gggcgcccuc   1320
gggguauucg caguuccaga aaugugccug gcaggcgaca gcacaaccca cauguuuaca   1380
aaauaugaga augcaaaucc gggugagaaa gggggugaau ucaaagggag uuuuacucug   1440
gauacuaacg cuaccaaccc ugcacgcaac uuuugucccg uugauuaucu cuucgggagc   1500
ggaguacugg cgggaaaugc guuuguuuac ccacaucaga uaauuaaucu gcgcaccaac   1560
aacugugcca cguuggugcu gccauacguu aauucacuuu ccauagacag caugacaaaa   1620
cacaacaauu ggggaauugc uauccuuccg cuggcaccac uugacuuugc caccgagucc   1680
uccacugaga uacccauuac ucuaacuauu gccccuaugu guugugaauu caaugggguug   1740
cgcaacauca cuguacccag aacucaaggg uugccagucu uaaacacucc aggaagcaac   1800
caguacuuaa cagcagacaa cuaucaaucc ccaugugcga uacccgaguu ugauguaaca   1860
ccacccauag acaucccggg ggaagugcgc aacaugaugg aauuggcaga gauagacacc   1920
augauaccuc ucaaucugac gaaccagcgc aagaacacca uggauaugua cagagucgaa   1980
cugaaugaug cggcucacuc ugacacacca auauuguguc ucucacuguc uccagcauca   2040
gauccuaggc uagcacacac uaugcuaggu gaaauacuga acuacuacac acacugggca   2100
gggucauuga aguucacauu ucucuucugc ggcucaauga uggccacugg uaaauugcua   2160
guguccuaug caccuccugg ugcggaagcc ccuaaaagcc gcaaagaagc gaugcucggc   2220
acccacguga ucugggacau cggauuacag ucaucaugca cuaugguggu accuuggauu   2280
agcaacacca cauacagaca aaccaucaac gauagcuuca cagaaggagg guacaucagu   2340
auguuuuacc aaacuagagu uguugugcca uuguccaccc cuagaaagau ggacauauug   2400
ggcuuugugu cagccugcaa ugacuucagu gugcgccugu ugcgugacac gacgcacaua   2460
agccaagagg cuaugccaca aggauugggu gauuuaauug aaggggguugu ugagggaguc   2520
acgagaaaug ccuugacacc acugacaccu gccaacaacu ugccugauac acaaucuagc   2580
ggcccagccc acucuaagga aacaccagcg cuaacagccg uagagacagg ggccaccaac   2640
ccauuggugc cuucagacac gguacaaacu cgucacguca uccaaaagcg gacgcggucg   2700
gagucuacgg uugagucuuu cuucgcaaga ggagcuugug uggccauuau ugaaguggau   2760
aaugaugcuc caacaaagcg ugccaguaaa uuauuuucag ucuggaagau aacuuacaaa   2820
gacaccguuc aguuaagacg uaaguuggag uucuuuacau auucaagguu ugacauggag   2880
uucaccuuug ugguuacauc caauuauacc gaugcaaaca augggcacgc acuaaaucaa   2940
```

-continued guuuaccaga uaauguacau accaccuggg gcaccgaucc cuggcaagug gaaugauuac 3000
acauggcaaa cgucaucuaa cccaucagug uuuuacacuu acggggcacc uccagcuaga 3060
auaucagugc ccuacguggg cauugccaau gcauauucuc auuuuuacga uggguuugcc 3120
aaaguaccac uagcaggcca agccucaaca gagggugacu cgcuguaugg agcggcuuca 3180
uugaaugacu ucggaucacu ggcuguucga guggugaaug accacaaccc uacgaaacuc 3240
acuucaaaaa ucagagugua caugaaacca aagcacguca gagugugggug uccgcgaccc 3300 ccucgagcag ucccauacua cggaccaggg guugacuaca aggauggacu agccccacug 3360
ccagggaaag gcuugacaac cuaugguuuu ggccaccaaa auaaggcagu guacacggca 3420
gguuacaaaa uuugcaauua ccaccucgcc acccaggaag acuuacaaaa ugcgguaaac 3480
auuaugugga uuagagaccu uuuaguagug gaauccaaag cccaaggcau agacacaauu 3540
gcuagaugua acugccacac uggaguguac uacugugaau ccaggaggaa guacuacccg 3600
gucucuuuua cuggccccac cuuucaguac auggaagcaa augaguacua uccagcccga 3660
uaccaauccc acauguuaau uggccauggu uuugcaucuc caggggacug uggugggauu 3720
cucaggugcc aacauggagu aauuggaauc auuacagcug gaggagaagg ccuagucgcu 3780
uucgcggaca ucagagaucu guacgcauac gaggaggagg cuauggagca gggagucucc 3840
aacuauauug agucccuugg ggcugcauuu gggaguggau ucacucagca aauaggaaac 3900
aaaauuucag aacucacuag cauggucacc agcacuauaa cugagaaacu acuaaagaau 3960
cucauuaaaa uaauuucauc ccuuguuauc aucaccagaa acuaugaaga cacgaccaca 4020
gugcuggcua cccuugcucu ccucgguugu gaugcguccc cauggcaaug gcuaaagaag 4080
aaagccugug acaucuugga aaucccccuac aucaugcgac agggcgauag cugguugaag 4140
aaguuuacag aggcaugcaa ugcagccaag ggauuggaau gggugucuaa uaaaauaucc 4200
aaauuuauug acuggcucaa agagaagauc auuccacagg cuagagacaa gcuagaguuu 4260
guuaccaaac ugaagcaacu agaaauguug gagaaccaaa uugcaaccau ucaucaaucg 4320
ugcccaaguc aggagcauca agaaauccug uucaauaacg ugagaugguu auccauacag 4380
ucaaagagau uugccccgcu cuaugcgguu gaggcuaaga gaauacaaaa guuagagcac 4440
acgauuaaca acuacguaca guucaagagc aaacaccgua uugaaccagu auguuuguug 4500
gugcacggua gcccaggcac gggcaaguca guugccacca auuuaauugc cagagcaaua 4560
gcagagaagg agaacaccuc cacauacuca cuaccaccag aucccuccca uuucgauggg 4620
uacaagcaac aagguguggu gaucauggau gauuugaauc agaacccaga cggagcagac 4680
augaagcugu uugucagau ggucuccacu guagaauuca uaccaccaau ggcuucgcua 4740
gaagaaaagg guauuuuguu cacaucuaau uacguuuugg ccucaaccaa uuccagucgc 4800
aucaccccac caacuguugc gcacagcgau gcccuagcca ggcgcuuugc auuugacaug 4860
gacauacaaa ucaugagcga guauucuaga gauggaaaau ugaacauggc gauggcaacu 4920
gaaaugugua agaacuguca ucaaccagca aacuucaaga gauguugccc auuggugugu 4980
ggcaaagcca uccagcugau ggacaaaucu uccagaguca gauauaguau agaucagauu 5040
acuaccauga uuauuaauga gaggaacaga agaucaagua ucgguaauug cauggaggca 5100
cuuuuccaag guccucuuca auacaaagac cugaaaauag acauuaagac cacaccuccu 5160
ccugagugca ucaaugauuu gcuccaagca guugauucuc aagagguaag agacuacugu 5220
gagaagaagg guuggauagu agacaucacu agucaggugc aaaccgaaag aaacaucaau 5280

-continued

```
agagcaauga cuauucuuca ggcggucacc acauuugccg caguugcugg aguggugua u   5340
gugauguaca aacucuuugc agggcaucaa ggagcguaua cagggcuucc caauaagaga    5400
cccaaugucc ccaccaucag gacugccaag guucagggcc caggauuuga cuacgcagug    5460
gcaauggcca aaagaaacau ucuuacggca acuaccauua agggagaguu cacaaugcuc    5520
ggagugcaug auaauguggc cauucuacca acccacgcau caccggguga aacaauaguc    5580
auugauggca aggaaguaga gguacuggau gcuaaagccc uggaggacca ggccgggacc    5640
aaccuagaaa ucaccaucgu cacucuuaag agaaaugaga aguucaggga caucagacca    5700
cacaucccca cucaaaucac ugagacaaau gauggaguuu uaauugugaa cacuaguaag    5760
uaccccaaca uguauguucc ugucggugcu gugacugaac aggggguaucu caaucucggu   5820
ggacgccaaa cugcucguac uuuaauguac aacuuuccaa cgagagcagg ucaauguggu    5880
ggaguuauca ccugcacugg caaggucauc gggaugcaug uuggugggaa cgguucacau    5940
ggguucgcag cagcccugaa gcgauccuau uucacucaga gucaagguga aauccagugg    6000
augagaccau caaaagaagu gggcuacccc guuauuaaug cuccaucuaa aacuaaacug    6060
gaacccagug cauuccauua uguguuugaa ggugucaagg aaccagcugu gcucaccaaa    6120
agugacccca gauugaagac agauuuugaa gaggcuaucu uuuccaagua ugugggaaau    6180
aagauuacug aaguggauga guacaugaaa gaagcugucg aucauuacgc aggccagcuc    6240
augucacuag acaucaacac agaacaaaug ugccuugagg augcaaugua uggcacugac    6300
ggucucgaag cucuagaccu caguaccagu gcuggguauc ccuauguggc aaugggggaaa   6360
aagaaaagag acauuuugaa uaagcaaacc agagacacaa aggaaaugca aaggcuucug    6420
gacaccuaug guauuaauuu accuuuaguc accuauguga aagaugagcu uagauccaag    6480
accaaagugg aacagggcaa guccaggcua auugaggccu caagucucaa ugacucuguc    6540
gccaugagga uggcuuuugg caacuuguac gcagcauucc acaagaaccc agguguagug    6600
acaggaucgg cuguuggcug ugacccagau uuguuuugga guaaaauacc aguccucaug    6660
gaggaaaaac ucuuugcauu ugauuacacg gguuaugaug cuucacuaag ccccgccugg    6720
uuugaggcuc ucaagauggu ucuagagaaa auuggguuug gugacagagu ggauuacauu    6780
gauuaucuga aucacucgca ccaucuauau aaaaauaaga cauauugugu uaagggcggc    6840
augccaucug gcugcucugg caccucaauu uuuaauucaa ugauuaauaa ucuaauaauc    6900
aggacucucu uacugaaaac cuacaagggc auagauuuag accaccugaa gaugauagcc    6960
uauggugaug auguaauugc uuccuacccc caugagguug augcuagucu ccuagcccaa    7020
ucaggaaaag acuauggacu aaccaugaca ccagcugaca aaucagccac cuuugaaaca    7080
gucacauggg agaauguaac auucuugaaa agauucuuua gagcagauga aaaguauccc    7140
uuucugauac auccagugau gccaaugaaa gaaauucacg aaucaauuag auggacuaaa    7200
gaucccagaa acacucagga ucauguucgc ucacugugcu uauuggcuug gcacaauggc    7260
gaggaagagu acaauaaauu uuuagcuaag auuagaagug ugccaaucgg aagagcauua    7320
cugcucccug aguacuccac auuguaccgc cguuggcucg acucauuuua guaacccuac    7380
cucagucgaa uuggauuggg ucauacuguu guagggguaa auuuuucuuu aauucggaga    7440
aaaaaaaaaa aaaaaaaaaa aaaaaaaaaa aaaaaaaaaa aaaaaaaaaa aaaaaaaaaa    7500
aa                                                                   7502
```

<210> SEQ ID NO 6
<211> LENGTH: 7440

-continued

<212> TYPE: RNA
<213> ORGANISM: Poliovirus

<400> SEQUENCE: 6
uuaaaacagc ucuggggguug uacccacccc agaggcccac guggcggcua guacuccggu 60
auugcgguac ccuuguacgc cuguuuuaua cucccuuccc guaacuuaga cgcacaaaac 120
caaguucaau agaagggggu acaaaccagu accaccacga acaagcacuu cuguuucccc 180
ggugaugucg uauagacugc uugcgugguu gaaagcgacg gauccguuau ccgcuuaugu 240
acuucgagaa gcccaguacc accucggaau cuucgaugcg uugcgcucag cacucaaccc 300
cagaguguag cuuaggcuga ugagucugga caucccucac cggugacggu gguccaggcu 360
gcguuggcgg ccuaccuaug gcuaacgcca ugggacgcua guugugaaca aggugugaag 420
agccuauuga gcuacauaag aauccuccgg ccccugaaug cggcuaaucc caaccucgga 480
gcaggugguc acaaaccagu gauuggccug ucguaacgcg caaguccgug gcggaaccga 540
cuacuuuggg uguccguguu uccuuuuauu uuauuguggc ugcuuauggu gacaaucaca 600
gauuguuauc auaaagcgaa uuggauuggc cauccgguga aagugagacu cauuaucuau 660
cuguuugcug gauccgcucc auugagugug uuuacucuaa guacaauuuc aacaguuauu 720
ucaaucagac aauuguauca uaaugggugc ucagguuuca ucacagaaag ugggcgcaca 780
ugaaaacuca aauagagcgu augguggguuc uaccauuaau uacaccacca uuaauuauua 840
uagagauuca gcuaguaacg cggcuucgaa acaggacuuc ucucaagacc cuuccaaguu 900
caccgagccc aucaaggaug uccugauaaa aacagcccca augcuaaacu cgccaaacau 960
agaggcuugc ggguauagcg auagaguacu gcaauuaaca cugggaaacu ccacuauaac 1020
cacacaggag gcggcuaauu caguagucgc uuaugggcgu uggccugaau aucugaggga 1080
cagcgaagcc aauccagugg accagccgac agaaccagac gucgcugcau gcagguuuua 1140
uacgcuagac accgugucuu ggacgaaaga gucgcgaggg ugguggugga aguugccuga 1200
ugcacugagg gacaugggac ucuuugggca aaauauguac uaccacuacc uagguagguc 1260
cggguacacc gugcauguac aguguaacgc cuccaaauuc caccaggggg cacuaggggu 1320
auucgccgua ccagagaugu gucuggccgg ggauagcaac accacuacca ugcacaccag 1380
cuaucaaaau gccaauccug gcgagaaagg aggcacuuuc acggguacgu ucacuccuga 1440
caacaaccag acaucaccug cccgcagguu cugcccggug gauuaccucc uuggaaaugg 1500
cacguuguug ggaaaugccu uuguguuccc gcaccagaua auaaaccuac ggaccaacaa 1560
cugugcuaca cugguacucc cuuacgugaa cucccucucg auagauagua ugguaaagca 1620
caauaauugg ggaauugcaa uauuaccauu ggccccauua aauuuugcua gugaguccuc 1680
cccagagauu ccaaucaccu ugaccauagc cccuaugugc ugugaguuca auggauuaag 1740
aaacaucacc cugccacgcu uacagggccu gccggucaug aacaccccug guagcaauca 1800
auaucuuacu gcagacaacu uccagucacc gugugcgcug ccugaauuug augugacccc 1860
accuauugac auacccggug aaguaaagaa caugauggaa uuggcagaaa ucgacaccau 1920
gauucccuuu gacuuaagug ccacaaaaaa gaacaccaug gaaauguaua ggguucgguu 1980
aagugacaaa ccacauacag acgaucccau acucugccug ucacucucuc cagcuucaga 2040
uccuagguug ucacauacua ugcuuggaga aauccuaaau uacuacacac acugggcagg 2100
aucccugaag uucacguuuc uguucugugg auucaugaug gcaacuggca aacuguuggu 2160
gucauacgcg ccuccuggag ccgacccacc aaagaagcgu aaggaggcga uguugggaac 2220

-continued acaugugauc ugggacauag gacugcaguc cucauguacu augguagugc cauggauuag 2280
caacaccacg uaucggcaaa ccauagauga uaguuucacc gaaggcggau acaucagcgu 2340
cuucuaccaa acuagaauag ucgucccucu uucgacaccc agagagaugg acauccuugg 2400
uuuuguguca gcguguaaug acuucagcgu gcgcuuguug cgagauacca cacauauaga 2460
gcaaaaagcg cuagcacagg gguuagguca gaugcuugaa agcaugauug acaacacagu 2520
ccgugaaacg gugggggcgg caacaucuag agacgcucuc ccaaacacug aagccagugg 2580
accaacacac uccaaggaaa uuccggcacu caccgcagug gaaacugggg ccacaaaucc 2640
acuagucccu ucugauacag ugcaaaccag acauguugua caacauaggu caaggucaga 2700
gucuagcaua gagucuuucu ucgcgcgggg ugcaugcgug accauuauga ccguggauaa 2760
cccagcuucc accacgaaua aggauaagcu auuugcagug uggaagauca cuuauaaaga 2820
uacuguccag uuacggagga aauuggaguu cuucaccuau ucuagauuug auauggaacu 2880
uaccuuugug guuacugcaa auuucacuga gacuaacaau gggcaugccu uaaaucaagu 2940
guaccaaauu auguacguac caccaggcgc uccagugccc gagaaauggg acgacuacac 3000
auggcaaacc ucaucaaauc caucaaucuu uuacaccuac ggaacagcuc cagcccggau 3060
cucgguaccg uauguuggua uuucgaacgc cuauucacac uuuuacgacg guuuuuccaa 3120
aguaccacug aaggaccagu cggcagcacu aggugacucc cuuuauggug cagcaucucu 3180
aaaugacuuc gguauuuugg cuguuagagu agucaaugau cacaacccga ccaaggucac 3240
cuccaaaauc agaguguauc uaaaacccaa acacaucaga gucuggugcc cgcguccacc 3300
gagggcagug gcguacuacg gcccuggagu ggauuacaag gaugguacgc uuacaccccu 3360
cuccaccaag gaucugacca cauauggauu cggacaccaa aacaaagcgg uguacacugc 3420
agguuacaaa auuugcaacu accacuuggc cacucaggau gauuugcaaa acgcagugaa 3480
cgucaugugg aguagagacc ucuuagucac agaaucaaga gcccagggca ccgauucaau 3540
cgcaaggugc aauugcaacg caggggugua cuacugcgag ucuagaagga aauacuaccc 3600
aguauccuuc guuggcccaa cguuccagua cauggaggcu aauaacuauu acccagcuag 3660
guaccagucc cauaugcuca uuggccaugg auucgcaucu ccaggggauu gugguggcau 3720
acucagaugu caccacgggg ugauagggau cauuacugcu gguggcgaag gguugguugc 3780
auuuucagac auuagagacu uguaugccua cgaagaagaa gccauggaac aaggcaucac 3840
caauuacaua gagucacuug ggccgcauu uggaagugga uuuacucagc agauuagcga 3900
caaaauaaca gaguugacca auauggugac caguaccauc acugaaaagc uacuuaagaa 3960
cuugaucaag aucauauccu cacuaguuau uauaacuagg aacuaugaag acaccacaac 4020
agugcucgcu acccuggccc uucuugggug ugaugcuuca ccauggcagu ggcuuagaaa 4080
gaaagcaugc gauguucugg agauaccuua ugucaucaag caaggugaca guugguugaa 4140
gaaguuuacu gaagcaugca acgcagcuaa gggacuggag ugggugucaa acaaaaucuc 4200
aaaauucauu gauuggcuca aggagaaaau uaucccacaa gcuagagaua aguuggaauu 4260
uguaacaaaa cuuagacaac uagaaaugcu ggaaaaccaa aucucaacua uacaccaauc 4320
augcccuagu caggaacacc aggaaauucu auucaauaau gucagauggu uauccaucca 4380
gucuaagagg uuugccccuc uuuacgcagu ggaagccaaa agaauacaga aacuagagca 4440
uacuauuaac aacuacauac aguucaagag caaacaccgu auugaaccag uauguuugcu 4500
aguacauggc agccccggaa cagguaaauc uguagcaacc aaccugauug cuagagccau 4560
agcugaaaga gaaaacacgu ccacguacuc gcuacccccg gauccaucac acuucgacgg 4620
auacaaacaa cagggagugg ugauuaugga cgaccugaau caaaacccag auggugcgga 4680
caugaagcug uucugucaga ugguaucaac aguggaguuu auaccaccca uggcaucccu 4740
ggaggagaaa ggaauccugu uuacuucaaa uuacguucua gcauccacaa acucaagcag 4800
aauuuccccc cccacugugg cacacaguga ugcauuagcc aggcgcuuug cguucgacau 4860
ggacauucag gucaugaaug aguauucuag agaugggaaa uugaacaugg ccauggcuac 4920
ugaaaugugu aagaacuguc accaaccagc aaacuuuaag agaugcuguc cuuuagugug 4980
ugguaaggca auucaauuaa uggacaaauc uuccagaguu agauacagua uugaccagau 5040
cacuacaaug auuaucaaug agagaaacag aagauccaac auuggcaauu guauggaggc 5100
uuuguuucaa ggaccacucc aguauaaaga cuugaaaauu gacaucaaga cgagucccc 5160 uccugaaugu aucaaugacu ugcuccaagc aguugacucc caggagguga gagauuacug 5220
ugagaagaag gguuggauag ucaacaucac cagccagguu caaacagaaa ggaacaucaa 5280
cagggcaaug acaauucuac aagcggugac aaccuucgcc gcaguggcug gaguugucua 5340
ugucauguau aaacuguuug cuggacacca gggagcauac acugguuuac caaacaaaaa 5400
acccaacgug cccaccauuc ggacagcaaa gguacaagga ccaggguucg auuacgcagu 5460
ggcuauggcu aaaagaaaca uuguuacagc aacuacuagc aagggagagu ucacuauguu 5520
aggaguccac gacaacgugg cuauuuuacc aacccacgcu ucaccuggug aaagcauugu 5580
gaucgauggc aaagaagugg agaucuugga ugccaaagcg cucgaagauc aagcaggaac 5640
caaucuugaa aucacuauaa ucacucuaaa gagaaaugaa aaguucagag acauuagacc 5700
acauauaccu acucaaauca cugagacaaa ugauggaguc uugaucguga acacuagcaa 5760
guaccccaau auguauguuc cugucggugc ugugacugaa cagggauauc uaaaucucgg 5820
ugggcgccaa acugcucgua cucuaaugua caacuuucca accagagcag gacagugugg 5880
uggagucauc acauguacug ggaaagucau cgggaugcau guugguggga acgguucaca 5940
cggguuugca gcggcccuga agcgaucaua cuucacucag agucaaggug aaauccagug 6000
gaugagaccu ucgaaggaag ugggauaucc aaucauaaau gccccgucca aaaccaagcu 6060
ugaacccagu gcuuuccacu auguguuuga aggggugaag gaaccagcag uccucacuaa 6120
aaacgauccc aggcuuaaga cagacuuuga ggaggcaauu uucuccaagu acgugggguaa 6180 caaaauuacu gaaguggaug aguacaugaa agaggcagua gaccacuaug cuggccagcu 6240
caugucacua gacaucaaca cagaacaaau gugcuuggag gaugccaugu auggcacuga 6300
uggucuagaa gcacuugauu uguccaccag ugcuggcuac ccuuauguag caaugggaaa 6360
gaagaagaga gacaucuuga acaaacaaac cagagacacu aaggaaaugc aaaaacugcu 6420
cgacacauau ggaaucaacc ucccacuggu gacuuaugua aaggaugaac uuagauccaa 6480
aacaaagguu gagcagggga aauccagauu aauugaagcu ucuaguuuga augacucagu 6540
ggcaaugaga auggcuuuug ggaaccuaua ugcugcuuuu cacaaaaacc caggagugau 6600
aacagguuca gcagugggggu gcgauccaga uuuguuuugg agcaaaauuc cgguauugau 6660
ggaagagaag cuguuugcuu uugacuacac aggguaugau gcaucucuca gcccugcuug 6720
guucgaggca cuaaagaugg ugcuugagaa aaucggauuc ggagacagag uugacuacau 6780
cgacuaccua aaccacucac accaccugua caagaauaaa acauacugug ucaagggcgg 6840
uaugccaucu ggcugcucag gcacuucaau uuuuaacuca augauuaaca acuugauuau 6900
caggacacuc uuacugaaaa ccuacaaggg cauagauuua gaccaccuaa aaaugauugc 6960

-continued cuauggugau gauguaauug cuuccuaccc ccaugaaguu gacgcuaguc uccuagccca 7020
aucaggaaaa gacuauggac uaacuaugac uccagcugac aaaucagcua cauuugaaac 7080
agucacaugg gagaauguaa cauucuugaa gagauucuuc agggcagacg agaaauaccc 7140
auuucuuauu cauccaguaa ugccaaugaa ggaaauucau gaaucaauua gauggacuaa 7200
agauccuagg aacacucagg aucacguucg cucucugugc cuuuuagcuu ggcacaaugg 7260
cgaagaagaa uauaacaaau uccuagcuaa aaucaggagu gugccaauug gaagagcuuu 7320
auugcuccca gaguacucaa cauuguaccg ccguuggcuu gacucauuuu aguaacccua 7380
ccucagucga auuggauugg gucauacugu uguaggggua aauuuuucuu uaauucggag 7440

<210> SEQ ID NO 7
<211> LENGTH: 7471
<212> TYPE: RNA
<213> ORGANISM: Poliovirus

<400> SEQUENCE: 7
uuaaaacagc ucugggguug uacccacccc agaggcccac guggcggcua guacuccggu 60
accacgguac ccuuguacgc cuguuuuaua cucccuuccc ccgcaauuua gaagcucaug 120
aucaaguuca auaggagggg guacaaacca guaccaccac gaacaagcac uucuguuucc 180
ccggugaugu uguauagacu gcucgcgcgg uuaaaagcga cggauccguu auccgcucau 240
guacuucgag aagccuagua uuaccucggg aucuucgacg cguugcgcuc agcacucaac 300
cccagagugu agcuuagguc gaugagucug gacauuccuc accggcgacg gugguccagg 360
cugcguuggc ggccuaccua uggcuaacgc cauaggacgc uaguugugaa caagguguga 420
agagccuauu gagcuacaug agaguccucc ggccccugaa ugcggcuaau cccaaccucg 480
gagcaggcga ucacaagcca gugauuggcc ugucguaaug cguaaguccg agacggaacc 540
gacuacuuug gguguccgug uuuccuuuua uuuuuaucau ggcugccuau ggugacaauc 600
agugauuguu gucauagagc gaauuggauu ggccauccgg ugaaaacaaa gucaauuacu 660
uucucacuug uuggaccuac acccgauacg cuuuaccccc aagcuaauua aaauuauuag 720
aaguuaggac uacgguguca caaugggagc ucaaguuucg ucccaaaaag uaggcgcuca 780
ugaaaauucc aaccgggccu ccgguggcuc caccaucaac uacaccacaa uuaauuauua 840
uaaagauucu gcuaguaaug cggcgucuaa gcaagacuac ucacaggacc cuucaaaguu 900
caccgagccg cuaaaggaug ugcucauaaa gacagcucca gcacucaauu caccaaaugu 960
ggaggcgugc ggguauagcg auagaguguu acaacucacu uuaggcaauu ccaccauuac 1020
uacacaggag gcagccaacu caguaguagc cuacggacgg uggccugaau ucauuagaga 1080
ugaugaagca aacccagugg aucaaccaac ugagccagac guugccacau gcagauuuua 1140
cacucuagac acuguaaugu ggggcaagga guccaaaggu ugguggugga aguugccuga 1200
ugcacugaga gacaugggug uguuuggaca aaacauguau uaccacuacc uaggaagauc 1260
uggguacacu gugcacgugc agugcaacgc uucuaaauuu caucaaggcg cacuaggggu 1320
guuugcgauu ccugaruauu gucuggcagg cgacagugac aagcaaaggu acacuaguua 1380
ugcaaaugca aauccaggcg aaaagggagg gaaauuuuac ucccaguuca acaaggauaa 1440
cgcaguaacg uccccaaaaa gagaguuuug cccaguggau uaucuccugg gaugcggggu 1500
guugcuggga aaugccuuug uauacccaca ccagaucauu aaucugagga ccaauaacag 1560
cgcaaccauu guccuaccau acgugaaugc uuuagcuauu gacucaaugg uuaaacacaa 1620 caacugggge auugccauuu ugcccuuauc accguuggac uuugcucagg auucaucagu 1680
ugaaauuccg auuaccguga caauugcccc aauguguagu gaguucaaug gucuccgcaa 1740
cgugacugca cccaaauuuc aaggrcuacc agugcugaau acaccuggaa guaaccagua 1800
ccuaacauca gacaaccacc aaucaccaug cgcaaucccu gaauuugaug ucacuccgcc 1860
uaucgauauc ccaggygagg uuaaaaacau gauggagcuc gccgagauag acaccaugau 1920
cccccucaau uuggagaaua cuaagagaaa uacaauggac auguacaggg ucacucugag 1980
cgacagugcc gaucuaucgc aaccaauucu gugcuugucg cuaucuccgg caucugaucc 2040
gcgcuugucg cacaccaugc uuggggaagu gcugaacuau uauacucauu gggcuggauc 2100
uuugaaguuc acuuuucugu ucuguggcuc aaugauggcu acagggaaaa ucuuagugc 2160 cuaugcacca ccgggcgcac aaccccccac cagucguaag gaggccaugu ugggcacaca 2220
ucucauuugg gaucuugguc ugcaaucauc cugcaccaug gugguaccau ggauuagcaa 2280
cgugacauac agacagacua cacaagauag cuucacugaa ggcggauaua uuagcauguu 2340
uuaccaaaca aggauuguag ugccacuauc cacccccaag aguaugaaca ugcugggguu 2400
ugugucagcc uguaacgacu uuagugugcg auugcuacga gacaccacuc acauuucaca 2460
aucagcgcuu ccacagggca uugaagaauu gauuuccgaa gucgcgcaag gcgcccuaac 2520
uuuaucacuc cccaagcagc aggacagcuu accugacacc aaggccagug gcccggcgca 2580
cuccaaggag gugccugcac ucacugcagu cgagacuggg gcuaccaauc cucugguacc 2640
auccgacaca guucaaacgc gccauguaau ccaacggcgu agcaggucag aguccacgau 2700
agaaucauuc uucgcacgcg gggcgugcgu ugcuaucauu gagguagaca acgaacaacc 2760
aaccacccgg gcacagaaac uuuuugccac guggcgcauu acguacaaag auacaguaca 2820
auuacgccgc aaauuggagu ucuuuacaua cucccguuuu gacauggaau ucaccuuugu 2880
aguaacugcu aacuucacca acgccaauaa cgggcaugcc cugaaccaag uguaccagau 2940
aauguacauc cccccaggag caccuacacc aaagucaugg gacgacuaca ccuggcaaac 3000
aucuuccaac ccgucuauau ucuacaccua uggggcugca ccggcgcgaa uuucaguacc 3060 auacguggg uuggccaaug cuuacucaca cuuuuacgac ggcuuugcca aggugccacu 3120
gaaaacagac gccaacgacc aaauugguga uuccuuguac agugcuauga caguggacga 3180
cuuuggugug uuggcaauuc gaguugucaa ugaucacaac ccccacuaarg uaaccuccaa 3240 aauccgcauu uacaugaaac ccaaacacgu gcgugucugg ugcccuagac caccacgcgc 3300
gguaccuuuu uauggaccag ggguggacua caaagacaac uugaaccccu ugucugygaa 3360
agguuugacc accuauggcu uuggacauca gaauaaggcu guuuauaccg cuggauacaa 3420
gauuuguaac uaucaccuug cuacccaaga ggaucuacaa aaugcugugu guaucaugug 3480
gaacagagau cuuguguuug uugauucaaa agcucaaggc accgacucga uagcuagaug 3540
uaacugcaac gcaggggugu auuacuguga guccaggaga aaauacuacc cugugucauu 3600
cauaggaccc accuuucagu uuauggaggc caaugacuau uacccugcaa gguaucaguc 3660
ccacauguua auugggcacg guuuugccuc accaggcgau uguggcggca uucuuagaug 3720
ccagcauggc guuauuggga uuauaacagc ugguggugaa ggcuuggucg cauuuucaga 3780
cauaagagau cuuuaugcau augaagagga agcuauggag cagggaauau ccaauuacau 3840
agagucgcuc ggagcagcgu ucggcagcgg guuuacucag caaauagggg acaagaucuc 3900
agagcugacu agcaugguga ccagcacaau uacggagaaa uuacuaaaga accuaaucaa 3960
gaucaucuca ucacugguga ucauaaccag aaacuacgag gacaccacca cagugcuugc 4020

-continued caccuuagcu cucccuuggau gugacaucuc gccauggcag ugguuaaaga agaaggcaug 4080
ugauauucug gaaauaccau augucauuaa acagggugau agcugguuga agaaguuuac 4140
ugaggcaugc aacgccgcca aggggcuaga gugggugucu aauaaaauuu caaaguuuau 4200
ugauugguua aaggagaaaa uuauuccaca ggcgagagau aaacuugagu uugucaccaa 4260
acuuaaacaa uuggaaaugc ucgaaaauca gauuuccacg auacaucaau cuugccccag 4320
ccaggaacac caggaaguuc uguucaacaa cgugcggugg uugucaauuc agucuaagaa 4380
guuugcgcca cuuuaugcgc uugaggccaa gagaauacaa aaguuagaac acaccaucaa 4440
uaauuacaua caguucaaga gcaaacaccg uauugaacca guguguuugu uggugcacgg 4500
gagcccaggc accggaaaau caguugcgac caaucuaauu gcuagagcca uagcagagaa 4560
agagaacaca uccaccuacu cacugccacc agacccgucu cacuuugaug guuauaaaca 4620
gcaaggugug gucaucaugg augauuugaa ccaaaaccca gauggggcag auaugaaacu 4680
cuuuugucaa augguaucua cuguggaguu caucccgccu auggccucac uggaagaaaa 4740
aggcauuuug uucacaucca auuaugucuu ggcuuccacc aacuccaguc guaucacacc 4800
acccacagua gcccauagug acgcgcuggc uaggagauuc gccuucgaua uggacauaca 4860
aguaaugggc gaguauucca gagaugguaa acucaacaug gcaauggcca cugagaugug 4920
uaaaaacugc caccaaccag caaacuucaa gagaugcugc ccuuuggugu guggcaaggc 4980
uauucaguug auggacaaau ccucuagagu uagauacagu auugaccaga ucaccacuau 5040
gauuaucaau gagagaaaca gaagauccaa cauagguaau ugcauggagg cucuauucca 5100
aggaccacuc caguacaaag accugaaaau ugacaucaaa acgagucccc ccccugagug 5160
uaucaaugac cugcuacaag caguugacuc ccaagaagug agggauuauu gugaaaagaa 5220
agguuggauu guuaacauua ccagucaagu ucaaacagag agaaacauua aucgggcaau 5280
gacuauuuua caagcaguga caacauucgc ugcaguggcc ggugucgugu acguuaugua 5340
caaacuguuc gcuggccacc agggagcaua cacuggacug ccaaacaaaa gaccuaaugu 5400
acccaccauu agaacagcaa aagugcaagg gccuggauuu gacuacgcug uggcuauggc 5460
caaaagaaac auuguuacag caaccacuag uaagggagag uucaccaugc ugggagugca 5520
cgacaacgug gccauacuac cgacccaugc cucgccuggu gagagcaucg ugaucgaugg 5580
caaggagguu gaaauuuuag acgccaaagc ccucgaagau caagcaggca ccaaucugga 5640
aaucacuaua auaacccuca aaagaaauga gaaguucaga gacaucagau cucacauacc 5700
cacccaaauc acugagacaa augauggagu cuugaucgua aacacuagua aguaccccaa 5760
cauguauguu ccuguuggug cugugaccga acagggauau cucaaucucg gcggacguca 5820
gaccgcgcgu acauugaugu acaacuuucc aacacgagcg ggucaaugcg guggagucau 5880
caccugcacu ggcaaaguca ucgggaugca ugucgguggg aacgguucac auggguucgc 5940
agcagcccua aagcgaucuu acuucacuca gagucaaggu gagauucagu ggaugagacc 6000
aucaaaagag gugggguacc ccaucaucaa ugccccaucu aaaaccaagc uugagcccag 6060
cgccuuucac uauguguuug aagguguuaa agaaccagca guacucacau ggaaugaccc 6120
cagauugaaa acggacuuug aagaagccau cuucuccaag uauguaggga acaagauuac 6180
ugaaguggau gaguacauga aagaagcugu ugaccacuau gcuggucagc ucaugucccu 6240
ggacaucaac acugagcaga ugugccuaga agaugccaug uacggaacug auggauugga 6300
ggccuuggac cuaagcacua gugcaggaua ucccuaugug gcgaugggaa agaagaaaag 6360
agacaucuug aacaaacaga ccagagacac uaaggagaug cagagacugc ucgacaccua 6420

-continued

```
uggaaucaac cuuccguugg ugacguaugu caaagaugag cucagaucaa aagugaaggu   6480

ggaacagggc aagucuagac uaauugaggc auccagcuug aaugauuccg uugccaugag   6540

aauggcauuu gggaaucugu acgcugccuu ucauaagaau ccaggcguug uaacagguuc   6600

cgcaguugga ugugauccag accuauuuug gagcaggauc ccagugcuaa uggaggagaa   6660

gcuuuuugcc uuugauuaca cagguuauga cgccucgcuc aguccugcgu gguuugaggc   6720

acuuaaaaug gugcuugaga aaauuggcuu uggagacaga guagauuaca ucgacuaucu   6780

caaccauucu caccauuugu acaagaacaa aaccuauugu guuaagggug gcaugccauc   6840

uggcugcucu ggcacuucaa uuuucaauuc uaugauuaau aacuuaauua uuaggacacu   6900

auuacugaaa accuacaagg gcauagauuu agaccgccua aagaugaucg ccuaugguga   6960

ugauguaauu gcuuccuacc cccaugaggu ugacgcuagu cuccuagccc aaucaggaaa   7020

agacuaugga cuaaccauga caccagccga uaagucaacg acuuuugaaa cugucacaug   7080

ggagaaugua acauucuuga aaagauucuu cagagcagau gaaaaguacc ccuuucuaau   7140

acacccagua augccaauga aggagauuca cgaaucaauu agauggacaa aagauccaag   7200

gaacacacag gaucauguuc gcucacuaug ccuauuggcg uggcauaaug gcgaagaaga   7260

auauaacaaa uuuuuagcua aaauuagaag ugugccaauc ggaagagcuu uguugcuccc   7320

agaguacucu acacuguacc gccguuggcu ugacucauuu uaguaacccu accucagucg   7380

aauuggauug ggucauacug uuguggggu aaauuuuucu uuaauucgga gaaaaaaaaa   7440

aaaaaaaaaa aaaaaaaaaa aaaaaaaaaa a                                 7471
```

<210> SEQ ID NO 8
<211> LENGTH: 7452
<212> TYPE: DNA
<213> ORGANISM: Poliovirus

<400> SEQUENCE: 8

```
ttaaaacagc tctggggttg ttcccacccc agaggcccac gtggcggcta gtacactggt     60

atcacggtac ctttgtacgc ctgttttata ctccctcccc cgcaacttag aagcatacaa    120

ttcaagctca ataggagggg gtgcaagcca gcgcctccgt gggcaagcac tactgtttcc    180

ccggtgaggc cgcatagact gttcccacgg ttgaaagtgt ccgatccgtt atccgctcat    240

gtacttcgag aagcctagta tcgctctgga atcttcgacg cgttgcgctc agcactcaac    300

cccggagtgt agcttgggcc gatgagtctg gacagtcccc actggcgaca gtggtccagg    360

ctgcgctggc ggcccacctg tggcccaaag ccacgggacg ctagttgtga acagggtgtg    420

aagagcctat tgagctacat gagagtcctc cggcccctga atgcggctaa ttctaaccat    480

ggagcaggca gctgcaaccc agcagccagc ctgtcgtaac gcgcaagtcc gtggcggaac    540

cgactacttt gggtgtccgt gtttcctttt attcttgaat ggctgcttat ggtgacaatc    600

atagattgtt atcataaagc gagttggatt ggccatccag tgtgaatcag attaattact    660

cccttgtttg ttggatccac tcccgaaacg ttttactcct taacttattg aaattgtttg    720

aagacaggat ttcagtgtca caatgggagc tcaagtatca tcccaaaaag taggcgctca    780

cgagaattct aaccgagcct acggtggttc tacgatcaac tacaccacaa ttaattatta    840

taaagattcc gcaagtaatg cggcgtccaa acaagattac tcacaggatc catcaaaatt    900

caccgagcca ctaaaggacg tgctcataaa aacagctcca gcactcaatt caccaaatgt    960

ggaagcgtgt gggtatagtg atagagtgtt gcaactcact ttaggcaatt ccactattac   1020
```

-continued

```
tacacaggag gcagcaaatt cagtagtggc ttacggacgt tggcctgagt ttattagaga   1080
tgacgaagca aacccggtgg accaaccaac tgaaccagat gtggctacat gcagattcta   1140
cacactagac actgtaatgt ggggtaagga gtcgaaaggc tggtggtgga agttacctga   1200
cgcactgaga gacatgggtc tgtttggaca aaacatgtat taccactacc taggaagatc   1260
cgggtacact gtgcacgtgc agtgtaatgc atccaaattt caccaaggtg cactcggggt   1320
gtttgcgatt cctgagtatt gtctggcggg tgacagtgac aagcaaaggt acactagtta   1380
tgcaaatgcg aatccaggtg aaagaggggg aaaattttac tcccaattca acaaggataa   1440
cgcagtaaca tccccaaaaa gagagttctg cccagtggat tatctcctgg gatgtggggt   1500
gttactggga aatgcctttg tatacccaca tcaaatcatt aatctgagga ccaacaacag   1560
cgcaactatt gtcctaccat atgtgaatgc tttggccatt gattcaatgg ttaaacacaa   1620
caactggggc attgccattc tgcccttatc accgctggat tttgctcaag attcatcagt   1680
tgaaattcca attactgtga caattgcccc aatgtgtagc gagttcaacg gccttcgcaa   1740
cgtgactgca cctaaatttc aaggactacc agtgttgaac actcctggta gtaaccagta   1800
cctgacgtca gacaaccacc aatcaccatg cgcaatccca gaatttgatg tcactccgcc   1860
tattgatatc ccaggtgagg ttaaaaacat gatggagctc gccgagatag acaccatgat   1920
tcctctcaat ttggagagca ccaagagaaa cacaatggac atgtacagag ttactctgag   1980
cgacagtgcc gatctatcgc aaccaatttt gtgcttgtca ctatccccag catttgatcc   2040
gcgcttgtca cacaccatgc ttggggaagt actgaactat tatactcatt gggccgggtc   2100
cttgaaattt accttcctgt tctgtggttc aatgatggct acggggaaaa tcctagtggc   2160
ctatgcacca ccaggtgcac aacccccac cagccgtaag gaggctatgt tgggcacaca   2220
tgtcatttgg gatcttggcc tgcaatcatc ttgtactatg gtggtgccgt ggattagtaa   2280
tgtgacatac agacagacta cacaagatag tttcactgag ggcggatata tcagcatgtt   2340
ctaccaaaca agaattgtgg tgccactgtc cacccctaag agtatgagca tgctggggtt   2400
tgtgtcagcc tgtaatgatt tcagtgtgcg attgctgcga gacaccactc acatttcaca   2460
atctgcgctt ccacagggta ttgaagattt gatttctgaa gttgcacagg gcgccctaac   2520
tttgtcactc ccgaagcaac aggatagctt acctgatact aaggccagtg gcccggcgca   2580
ttccaaggag gtacctgcac tcactgcagt cgagactgga gccaccaatc ctctggcacc   2640
atccgacaca gttcaaacgc gccacgtagt ccaacgacgc agcaggtcag agtccacaat   2700
agaatcattc ttcgcacgcg gggcgtgcgt cgctattatt gaggtggaca atgaacaacc   2760
aaccacccgg gcacagaaac tatttgccat gtggcgcatt acatacaaag atacagtgca   2820
gttgcgccgt aagttggagt ttttcacata ctctcgtttt gacatggaat tcaccttcgt   2880
ggtaaccgcc aacttcacca acgctaataa tgggcatgca ctcaaccagg tgtaccagat   2940
aatgtacatc cccccagggg cacccacacc aaagtcatgg gacgactaca cttggcaaac   3000
atcttccaac ccgtccatat tttacaccta tggggctgcc ccggcgcgaa tctcagtgcc   3060
atacgtgggg ttagccaatg cttactcgca cttttacgac ggcttcgcca aggtgccatt   3120
gaagacagat gccaatgacc agattggtga ttccttgtac agcgccatga cagttgatga   3180
ctttggtgta ttggcagttc gtgttgtcaa tgatcacaac cccactaaag taacctccaa   3240
agtccgcatt tacatgaaac ccaaacacgt acgtgtctgg tgccctagac cgccgcgcgc   3300
ggtaccttat tatggaccag ggtggacta taggaacaac ttggacccct tatctgagaa   3360
aggtttgacc acatatggct ttgggcatca gaataaagct gtgtacactg ctggttacaa   3420
```

```
gatctgcaac taccatctcg ccactaagga ggatttacaa aatgctgtaa gcatcatgtg   3480
gaatagagac ctcttggttg ttgaatcaaa agctcaaggt accgactcaa tagcaaggtg   3540
caattgcaat gcaggggtgt actattgtga gtccagaagg aaatactacc ctgtgtcgtt   3600
tgtgggaccc accttccaat acatggaggc taatgactac tacccagcta gataccaatc   3660
ccacatgtta atcgggcacg gctttgcctc accaggtgac tgtggtggta tccttaggtg   3720
tcaacatggc gtcatcggaa tcgtgacagc tggtggagag ggattagtcg cattctctga   3780
cataagggac ttgtatgctt acgaggaaga ggccatggag cagggcattt caaactatat   3840
tgagtcactc ggtgctgcgt tcggtagtgg gttcactcag caaatagggg ataagatatc   3900
agaactaacc agcatggtga ccagcacgat tacagagaag ctacttaaaa acctaatcaa   3960
aattatttca tctctggtga ttatcactag aaattacgaa gataccacca cagtgctcgc   4020
cactctagct cttcttgggt gtgatgtttc accgtggcaa tggctgaaga agaaagcatg   4080
tgacactttg gagattccct atgttattag acagggtgat agttggttga aaaaatttac   4140
tgaggcgtgc aacgcagcta aggggttgga atgggtgtcc aacaaaatct caaaatttat   4200
tgactggttg agagaaagaa tcatcccaca agccagggac aagcttgagt ttgtaaccaa   4260
attgaaacag ttggaaatgc tagagaatca gatatccaca atacaccaat cttgtccaag   4320
tcaggaacac caggaaattt tgttcaacaa tgtacgctgg ttgtccattc aatccaagag   4380
attcgctcca ttgtacgcac ttgaggccaa gagaatacaa aagttggaac acaccattaa   4440
taattacata cagttcaaga gcaaacaccg tattgagcca gtatgtttgt tagtgcatgg   4500
gagcccaggt acaggaaaat cagttgcgac taacctaatt gctagagcca tagctgagaa   4560
agagaacacc tccacctact cgctaccacc ggacccgtct cactttgatg gatacaaaca   4620
acaaggtgtg gttatcatgg acgacctaaa ccaaaacccg gatggggcag atatgaagct   4680
cttttgtcaa atggtgtcca ctgtggagtt tatcccacct atggcctcgc tggaagagaa   4740
aggcattctg ttcacatcca actatgtttt agcctccacc aactccagtc gcatcacacc   4800
acctacagta gcccacagtg acgctctggc caggaggttc gctttcgata tggatattca   4860
agtgatgggc gagtactcca gagatggtaa actcaacatg gcaatggcta ctgagacgtg   4920
caaggactgc caccaaccag caaacttcaa aagatgctgt cctttagtgt gtggtaaggc   4980
aattcagtta atggacaaat cttccagagt taggtacagt gttgaccaga ttactacaat   5040
gattatcaac gagagaaaca gaagatctaa cattggcaat tgcatggagg ctttgttcca   5100
aggaccactc cagtacaaag acctgaaaat tgacatcaag acgaggcccc cccctgaatg   5160
catcaatgat ctgcttcaag cagttgactc ccaggaagtg agggattatt gtgaaaagaa   5220
aggatggatc gtcaacatca ctagccaagt tcaaacagag agaaacatta accgagcaat   5280
gaccattttg caggcagtga caactttcgc cgcagtggct ggtgtcgtgt acgtcatgta   5340
caagttattc gctggacacc agggagcata cactggtctg ccaaacaaaa gacccaatgt   5400
gcccaccatt agagcagcaa aagtgcaagg gcctgggttt gactatgcag tggctatggc   5460
taaaagaaac attgttacag caactactag caaaggggag ttcacaatgc taggagtcca   5520
cgacaacgtg gccattttac caactcatgc ctcacctggt gagagtattg taattgatgg   5580
caaagaggtt gaaatcctag acgctaaagc cctcgaagat caggcaggca ctaatctgga   5640
aatcaccata ataaccctca aaagaaatga aaagttcaga gatatcagac aacacatacc   5700
cactcaaatc accgagacga atgatggagt tctgattgtg aacactagta agtaccccaa   5760
```

-continued catgtatgtt cctgtcggtg ctgtgactga gcagggatac ctaaatctcg gtgggcgcca 5820
gactgctcgt attctaatgt acaactttcc aaccagagct ggtcagtgtg gtggagtcat 5880
cacatgcact gggaaagtca tcgggatgca cgttggtggg aatggttcac atgggtttgc 5940
agcggccctg aagcggtcat acttcactca gagccaaggt gaaatccagt ggatgagacc 6000
atcaaaggag gcagggtatc caattataaa cgccccaacc aagaccaagc tcgagcccag 6060
tgctttccac tatgtgtttg aaggagtaaa ggaaccagca gtcctcacaa agaatgatcc 6120
cagactcaaa acagactttg aagaagcaat cttctctaag tatgtaggga acaagatcac 6180
tgaggtggat gagtacatga aagaggcagt ggaccattat gctggacaac ttatgtcgct 6240
ggatatcagc acagagcaaa tgtgtctaga agacgccatg tatggtactg atggtctgga 6300
ggcgctagat ctgtctacca gtgccgggta cccctacgtg gcaatgggga agaagaagag 6360
agatatccta aacaagcaaa ccagagacac caaagaaatg caaagacttt tggacgctta 6420
cggaatcaac ctaccattag tgacatatgt caaggacgag ctgaggtcca aaacaaaagt 6480
ggaacaggga aaatccagac tgattgaagc ttccagtcta aatgactcag tggccatgag 6540
aatggcattt ggaaaccttt atgcagcatt ccacaggaat ccaggggtcg tcactggtag 6600
tgcagttgga tgcgatccag acctattctg gagcaagatc ccagtgttga tggaagaaaa 6660
gctatttgcc tttgattaca caggatacga cgcatcactt agcccagctt ggtttgaggc 6720
actcaagatg gtgttagaga aaattggttt tggagataga gtggattaca tagactacct 6780
taaccattca caccacttgt acaaaaacaa gatatattgt gttaagggcg gcatgccatc 6840
tggctgctcc ggcacttcaa tttttaattc aatgattaac aatttgatca ttaggacgct 6900
tttactgaaa acctacaagg gcatagattt ggaccactta aaaatgattg cctatggtga 6960
cgatgtaata gcttcctatc cccatgaggt tgacgctagt ctcctagccc aatcaggaaa 7020
agactatgga ctaaccatga ctccggcaga taaatctgcc acttttgaga cagtcacatg 7080
ggagaatgta actttcttga aaagattctt cagagcagat gagaaatacc ccttcctcat 7140
acatccagta atgccaatga aggaaattca tgaatcaatc agatggacaa aagatcctcg 7200
gaatacgcag gaccatgtac gctccttgtg tctattggct tggcacaacg gggaagaaga 7260
atacaacaaa tttttagcta aaattaggag tgtgccaatc ggaagagctt tgttgctccc 7320
agagtactca acattgtacc gccgttggct tgactcattt tagtaaccct acctcagtcg 7380
aattggattg ggtcatactg ttgtaggggt aaatttttct ttaattcgga ggaaaaaaaa 7440
aaaaaaaaaa aa 7452

<210> SEQ ID NO 9
<211> LENGTH: 7462
<212> TYPE: DNA
<213> ORGANISM: Poliovirus

<400> SEQUENCE: 9
ttaaaacagc tctggggttg cacccacccc agaggcccac gtggcggcta gtactccggt 60
attgcggtac ccttgtacgc ctgttttata ctcccttccc gtaacttaga cgcacaaaac 120
caagttcaat agaagggggt acaaaccagt accaccacga acaagcactt ctgtttcccc 180
ggtgatgttg tatagactgc ttgcgtggtt gaaagcgacg gatccgttat ccgcttatgt 240
acttcgagaa gcccagtacc acctcggaat cttcgatgcg ttgcgctcag cactcaaccc 300
cagagtgtag cttaggctga tgagtctgga catccctcac cggtgacggt ggtccaggct 360
gcgttggcgg cctacctatg gctaacgcca tgggacgcta gttgtgaaca aggtgtgaag 420

```
agcctattga gctacataag aatcctccgg cccctgaatg cggctaatcc caacctcggg    480
gcaggtggtc acaaaccagt gattggcctg tcgtaacgcg caagtccgtg gcggaaccga    540
ctactttggg tgtccgtgtt tcctttttatt ttattgtggc tgcttatggt gacaatcaca   600
gattgttatc ataaagcgaa ttggattggc catccggtga aagtgagatt cattatctat    660
ctgtttgctg gattcgctcc attgagtgtg tttactctaa gtacaatttc aacagttatt    720
tcaatcagac aattgtatca taatgggtgc tcaggtttca tcacagaaag tgggcgcaca    780
tgaaaactca aatagagcgt atggtggttc taccattaat tacaccacca ttaattatta    840
tagagattca gctagtaacg cggcttcgaa acaggacttc tctcaagacc cttccaagtt    900
caccgagccc atcaaggatg tcctgataaa aacatcccca atgctaaact cgccaaacat    960
agaggcttgc gggtatagcg atagagtact gcaattaaca ctgggaaact ccactataac   1020
cacacaggag gcggctaatt cagtagtcgc ttatgggcgt tggcctgaat atctgaggga   1080
cagcgaagcc aatccagtgg accagccgac agaaccagac gtcgctgcat gcaggtttta   1140
tacgctagac accgtgtctt ggacgaaaga gtcgcgaggg tggtggtgga agttgcctga   1200
tgcactgcgg gacatgggac tctttggcca aaatatgtac taccactacc taggtaggtc   1260
cgggtacacc gtgcatgtac agtgtaacgc ctccaaattc caccaggggg cactaggggt   1320
attcgccgta ccagagatgt gtctggccgg ggatagcaac accactacca tgcacaccag   1380
ctatcaaaat gccaatcctg gcgagaaagg aggcactttc acgggtacgt tcactcctga   1440
cgacaaccag acatcacctg cccgtaggtt ctgcccggtg gattacctct ttggaaatgg   1500
cacgttattg gggaatgcct ttgtgttccc gcaccagata ataaacctac ggaccaacaa   1560
ctgtgctaca ctggtactcc cttacgtgaa ctccctctcg atagatagta tggtaaagca   1620
caataattgg ggaattgcaa tattaccatt ggccccatta aattttgcta gtgagtcctc   1680
cccagagatt ccaatcacct tgaccatagc ccctatgtgc tgtgagttca atggattaag   1740
aaacattacc ctgccacgct tacagggcct gccggtcatg aacacccctg gtagcaatca   1800
atatcttact gcagacaact tccagtcacc gtgtgcgctg cctgaatttg atgtgacccc   1860
acctattgac atacccggtg aagttaagaa catgatggaa ttggcagaaa tcgacaccat   1920
gattcccttt gacttaagtg caaaaaaaaa gaacaccatg gaaatgtata gggttcggtt   1980
aagtgacaaa ccacatacag acgatcccat actctgcctg tcactctctc cagcttcaga   2040
tcctaggttg tcacatacta tgcttggaga aatcctaaat tactacacac actgggcagg   2100
atccctgaag ttcacgtttc tgttctgtgg atccatgatg gcaactggca aactgttggt   2160
gtcatacgcg cctcctggag ccgacccacc aaagaagcgt aaggaggcga tgttgggaac   2220
acatgtgatc tgggacatag gactgcagtc ctcatgtact atggtagtgc catggattag   2280
caacaccacg tatcggcaaa ccatagatga tagtttcacc gaaggcggat acatcagcgt   2340
cttctaccaa accagaatag tcgtccctct ttcgacaccc agagagatgg acatccttgg   2400
ttttgtgtca gcgtgtaatg acttcagcgt gcgcttgatg cgagatacca cacatataga   2460
gcaaaaagcg ctagcacagg ggttaggtca gatgcttgaa agcatgattg acaacacagt   2520
ccgtgaaacg gtgggggcgg caacgtctag agacgctctc ccaaacactg aagccagtgg   2580
accagcacac tccaaggaaa ttccggcact caccgcagtg gaaactgggg ccacaaatcc   2640
actagtccct tctgatacag tgcaaaccag acatgttgta caacataggt caaggtcaga   2700
gtctagcata gagtctttct tcgcgcgggg tgcatgcgtg gccattataa ccgtggataa   2760
```

-continued

```
ctcagcttcc accaagaata aggataagct atttacagtg tggaagatca cttataaaga   2820
tactgtccag ttacggagga aattggagtt cttcacctat tctagatttg atatggaatt   2880
tacctttgtg gttactgcaa atttcactga gactaacaat gggcatgcct taaatcaagt   2940
gtaccaaatt atgtacgtac caccaggcgc tccagtgccc gagaaatggg acgactacac   3000
atggcaaacc tcatcaaatc catcaatctt ttacacctac ggaacagctc cagcccggat   3060
ctcggtaccg tatgttggta tttcgaacgc ctattcacac ttttacgacg gtttttccaa   3120
agtaccactg aaggaccagt cggcagcact aggtgactcc ctctatggtg cagcatctct   3180
aaatgacttc ggtattttgg ctgttagagt agtcaatgat cacaacccga ccaaggtcac   3240
ctccaaaatc agagtgtatc taaaacccaa acacatcaga gtctggtgcc cgcgtccacc   3300
gagggcagtg gcgtactacg gccctggagt ggattacaag gatggtacgc ttacacccct   3360
ctccaccaag gatctgacca catatggatt cggacaccaa aacaaagcgg tgtacactgc   3420
aggttacaaa atttgcaact accatttggc cactcaggaa gatttgcaaa acgcagtgaa   3480
cgtcatgtgg aatagagacc tcttagtcac agaatcaaga gcccagggca ccgattcaat   3540
cgcaaggtgc aattgcaacg caggggtgta ctactgcgag tctagaagga aatactaccc   3600
agtatccttc gttggcccaa cgttccagta catggaggct aataactatt acccagctag   3660
gtaccagtcc catatgctca ttggccatgg attcgcatct ccaggggatt gtggtggcat   3720
actcagatgt caccacgggg tgatagggat cattactgct ggtggagaag ggttggttgc   3780
atttacagac attagagact tgtatgccta cgaagaagaa gccatggaac aaggcatcac   3840
caattacata gagtcacttg ggccgcatt tggaagtgga tttactcagc agattggaga   3900
caaaataaca gagttgacta atatggtgac cagtaccatc actgaaaagc tacttaagaa   3960
cttgatcaag atcatatcct cactagttat tataactagg aattatgaag acaccacaac   4020
agtgctcgct accctggccc ttcttgggtg tgatgcttca ccatggcagt ggcttagaaa   4080
gaaagcatgc gatgttctgg agataccta tgtcaccaag caaggtgaca gttggttgaa   4140
gaagtttact gaagcatgca acgcagctaa gggactggag tgggtgtcaa acaaaatctc   4200
aaaattcatt gattggctca aggagaaaat tatcccacaa gctagagata agttggaatt   4260
tgtaacaaaa cttagacaac tagaaatgct ggaaaaccaa atctcaacta tacaccaatc   4320
atgccctagt caggaacacc aggaaattct attcaataat gtcagatggt tatccatcca   4380
gtctaagagg tttgcccctc tttacgcagt ggaagccaaa agaatacaga aactagagca   4440
taccattaac aactacatac agttcaagag caaacaccgt attgaaccag tatgtttgct   4500
agtacatggc agccccggaa caggtaaatc tgtagcaacc aacctgattg ctagagccat   4560
agctgaaaga gaaaacacgt ccacgtactc gctacccccg gatccatcac acttcgacgg   4620
atacaaacaa cagggagtgg tgattatgga cgacctgaat caaaacccag atggtgcgga   4680
catgaagctg ttctgtcaga tggtatcaac agtggagttt ataccaccca tggcatccct   4740
ggaggagaaa ggaatcctgt ttacttcaaa ttacgttcta gcatccacga actcaagcag   4800
aatttccccc cccactgtgg cacacagtga tgcattagcc aggcgctttg cgttcgacat   4860
ggacattcag gtcatgaatg agtattctag agatgggaaa ttgaacatgg ccatggctac   4920
tgaaatgtgt aagaactgtc accaaccagc aaactttaag agatgctgtc ctttagtgtg   4980
tggtaaggca attcaattaa tggacaaatc ttccagagtt agatacagta ttgaccagat   5040
cactacaatg attatcaatg agagaaacag aagatccaac attggcaatt gtatggaggc   5100
tttgttccaa ggaccactcc agtataaaga cttgaagatt gacatcaaga cgagtccccc   5160
```

```
tcctgaatgt atcaatgact tgctccaagc agttgactcc caggaggtga gagattactg   5220
tgagaagaag ggttggatag tcaacatcac cagccaggtt caaacagaaa ggaacatcaa   5280
cagggcaatg acaattctac aagcggtgac aaccttcgcc gcagtggctg gagttgtcta   5340
tgtcatgtat aaactgtttg ctggacacca gggagcatac actggtttac caaacaaaaa   5400
acccaacgtg cccaccatta ggacagcaaa ggtacaaggg ccagggttcg attacgcagt   5460
ggctatggct aaaagaaaca ttgttacagc aactactagc aagggagagt tcactatgtt   5520
aggagtccac gacaacgtgg ctattttacc aacccacgct tcacctggtg aaagcattgt   5580
gatcgatggc aaagaagtgg agatcttgga tgccaaagcg ctcgaagatc aagcaggaac   5640
caatcttgaa atcactataa tcactctaaa gagaaatgaa aagttcagag acattagacc   5700
acatatacct actcaaatca ctgagacaaa tgatggagtc ttgatcgtga acactagcaa   5760
gtaccccaat atgtatgttc ctgtcggtgc tgtgactgaa cagggatatc taaatctcgg   5820
tgggcgccaa actgctcgta ctctaatgta caactttcca accagagcag gacagtgtgg   5880
tggagtcatc acatgtactg ggaaagtcat cgggatgcat gttggtggga acggttcaca   5940
cgggtttgca gcggccctga agcgatcata cttcactcag agtcaaggtg aaatccagtg   6000
gatgagacct tcgaaggaag tgggatatcc aatcataaat gccccgtcca aaaccaagct   6060
tgaacccagt gctttccact atgtgtttga aggggtgaag gaaccagcag tcctcactaa   6120
aaacgatccc aggcttaaga caaactttga ggaggcaatt ttctccaagt acgtgggtaa   6180
caaaattact gaagtggatg agcacatgaa agaggcagta gaccactatg ctggccagct   6240
catgtcacta gacatcaaca cagaacaaat gtgcttggag gatgccatgt atggcactga   6300
tggtctagaa gcacttgatt tgtccaccag tgctggctac ccttatgtag caatgggaaa   6360
gaagaagaga gatatcttga acaaacaaac cagagacact aaggaaatgc aaaaactgct   6420
cgacacatat ggaatcaacc tcccactggt gacttatgta aaggatgaac ttagatccaa   6480
aacaaaggtt gagcagggga aatccagatt aattgaagct tctagtttga atgactcagt   6540
ggcaatgaga atggcttttg ggaacctata tgctgctttt cacaaaaacc caggagtgat   6600
aacaggttca gcagtagggt gcgatccaga tttgttttgg agcaaaattc cggtattgat   6660
ggaagagaag ctgtttgcct ttgactacac agggtatgat gcatctctca gccctgcttg   6720
gttcgaggca ctaaagatgg tgcttgagaa aatcggattc ggagacagag ttgactacat   6780
cgactaccta aaccactcac accacctgta caagaataaa acatactgtg tcaagggcgg   6840
tatgccatct ggttgctcag gcacttcaat ttttaactca atgattaaca acttgattat   6900
caggacactc ttactgaaaa cctacaaggg catagattta gaccacctaa aaatgattgc   6960
ctatggtgat gatgtaattg cttcctaccc ccatgaagtt gacgctagtc tcctagccca   7020
atcaggaaaa gactatggac taactatgac tccagctgac aaatcagcta tatttgaaac   7080
agtcacatgg gagaatgtaa cattcttgaa gagattcttc agggcagacg agaaataccc   7140
atttcttatt catccagtaa tgccaatgaa ggaaattcat gaatcaatta gatggacaaa   7200
agatcctagg aacactcagg atcacgttcg ctctctgtgc ctattagctt ggcacaatgg   7260
cgaagaagaa tataacaaat tcctagctaa aatcaggagt gtgccaattg gaagagcttt   7320
attgctccca gagtactcaa cattgtaccg ccgttggctt gactcatttt agtaacccta   7380
cctcagtcga attggattgg gtcatactgc tgtaggggta aatttttctt taattcggag   7440
gaaaaaaaaa aaaaaaaaaa aa                                            7462
```

<210> SEQ ID NO 10
<211> LENGTH: 7468
<212> TYPE: DNA
<213> ORGANISM: Poliovirus

<400> SEQUENCE: 10

```
ttaaaacagc tctggggttg tacccacccc agaggcccac gtggcggcta gcactccggt     60
attacggtac ccttgtgcgc ctgttttata ctcccctccc gcaacttaga agcacgaaac    120
caagttcaat agaagggggt acaaaccagt accactacga acaagcactt ctgtttcccc    180
ggtgacattg catagactgc tcacgcggtt gaaagtgatc gatccgttac ccgcttgtgt    240
acttcgaaaa gcctagtatc gccttggaat cttcgacgcg ttgcgctcag cacccgaccc    300
cggggtgtag cttaggctga tgagtctgga cattcctcac cggtgacggt ggtccaggct    360
gcgttggcgg cctacctatg gctaacgcca taggacgtta gatgtgaaca aggtgtgaag    420
agcctattga gctacataag agtcctccgg cccctgaatg cggctaatcc taaccacgga    480
acaggcggtc gcgaaccagt gactggcttg tcgtaacgcg caagtctgtg gcggaaccga    540
ctactttggg tgtccgtgtt tcctgttatt tttatcatgg ctgcttatgg tgacaatcag    600
agattgttat cataaagcga attggattgg ccatccggtg agtgttgtgt caggtataca    660
actgtttgtt ggaaccactg tgttagcttt acttctcatt taaccaatta atcaaaaaca    720
atacgaggat aaaacaacaa tactacaatg ggcgcccaag tttcatcaca gaaagttgga    780
gcccacgaaa attcaaacag agcctatggc gggtccacca tcaattacac tacaatcaat    840
tactataggg actctgcaag caatgcagca agcaagcaag attttgcaca agatccgtcc    900
aagttcaccg aacccattaa ggacgtcctt attaagaccg ctcccatgct aaactcccca    960
aacattgagg cgtgtggtta tagtgacagg gtaatgcagc taactctggg caattcaacg   1020
atcaccaccc aagaagcggc caattctgtt gttgcctacg gtagatggcc tgaatacatc   1080
agagataccg aggcaaatcc tgtagaccaa ccaaccgagc ccgatgtagc cgcgtgcagg   1140
ttctacacat tagataccgt cacttggcgc aaggagtcca gagggtggtg gtggaaacta   1200
ccagacgctt taaaagacat ggggttattt ggtcaaaaca tgttttatca ctatcttggg   1260
agggctggct acacagtgca cgtacagtgc aatgcttcaa agtttcatca aggagctcta   1320
ggggtgtttg cagttccaga aatgtgttta gctggtgata gcacaactca catgttcaca   1380
aagtacgaga atgcgaatcc aggcgaaaaa ggaggtgaat tcaaagggag tttcaccctt   1440
gataccaacg ccactaaccc tgcacggaac ttctgcccag ttgattacct cttcgggagt   1500
ggagtgctgg tagggaatgc atttgtttat ccacatcaaa taataaacct gcgcactaac   1560
aactgtgcta cgctagtatt gccctatgta aactcactct caatagatag catgacaaag   1620
cacaacaact gggggatcgc tatcctcccc ctggcgccac tagactttgc cactgaatct   1680
tccactgaga tacccattac actgaccatt gctcccatgt gctgcgaatt caatggttta   1740
cgcaacatca ctgtgccaag aacccaagga ttaccagtcc tgaacactcc agggagtaac   1800
cagtacctga ccgcagacaa ttaccagtct ccgtgtgcga tacctgagtt tgatgtcact   1860
ccacccatag acataccagg ggaggtgcgc aacatgatgg aattggcgga aatagacacc   1920
atgatacccc tcaacttgac aagtcaacgc aagaacacaa tggacatgta tagagtcgag   1980
ttgagcgaca cggctcactc tgacacgccg atcttgtgtc tctcgttgtc cccgcttca    2040
gaccccagat tggcacacac tatgttgggt gagatattaa attactacac acactgggca   2100
gggtccttga aatttacctt tctcttttgc ggctcaatga tggccaccgg aaagttattg   2160
```

gtttcttacg caccacccgg agcagaggcc cccaagagtc gcaaagaagc aatgcttggg 2220
acacatgtga tatgggacat tgggttgcag tcttcatgca ctatggtggt accttggatc 2280
agtaatacca catacagaca aaccatcaac gatagtttca cagaaggtgg ctacattagc 2340
atgttctatc aaactagggt tgttgtcccg ttgtccacac ccagaaagat ggacatcctg 2400
ggttttgtgt cagcttgcaa tgacttcagt gtgcgcttac tgcgagatac aacacacatt 2460
agtcaagagg ctatgccaca aggaattggt gacatgattg agggggccgt tgaagggatt 2520
actaaaaatg cattggttcc cccgacttcc accaatagcc tgcctgacac aaagccgagc 2580
ggtccagccc actccaagga gatacctgca ttgacagccg tggagacagg ggctaccaat 2640
ccgttggtgc cttcggacac cgtgcaaacg cgccatgtca tccagagacg aacgcgatca 2700
gagtccacgg ttgagtcatt ctttgcaaga ggggcttgcg tggctatcat tgaggtggac 2760
aatgatgcac cgacaaagcg cgccagcaga ttgttttcgg tttggaaaat aacttacaaa 2820
gatactgttc aactgagacg caaactggaa tttttcacat attcgagatt tgacatggag 2880
ttcacttttg tggtcacctc aaactacatt gatgcaaata acggacatgc attgaaccaa 2940
gtttatcaga taatgtatat accacccgga gcacctatcc ctggtaaatg gaatgactat 3000
acgtggcaga cgtcctctaa cccgtcggtg ttttacacct atggggcgcc cccagcaaga 3060
atatcagtgc cctacgtggg aattgctaat gcgtattccc acttttatga tgggtttgca 3120
aaagtaccac tagcgggtca agcctcaact gaaggcgatt cgttgtacgg tgctgcctca 3180
ctgaatgatt ttggatcact ggctgttcgc gtggtaaatg atcacaaccc cacgcggctc 3240
acctccaaga tcagagtgta catgaagcca aagcatgtca gagtctggtg cccacgacct 3300
ccacgagcag tcccatactt cggaccaggt gttgattata aagatgggct caccccacta 3360
ccagaaaagg gattaacgac ttatggattt ggacaccaaa acaaagctgt gtacacagct 3420
ggctacaaaa tttgcaatta ccacctagct acacaagaag acttgcaaaa tgccgtgagt 3480
gtcatgtgga acagagacct cttagtggct gaatcaaggg cccttggcac cgactcgatc 3540
gcaaggtgca gctgtaacac gggtgtgtac tactgtgaat ccaggagaaa atattatcca 3600
gtttctttca ttgggcccac cttccaatac atggaagcca atgaatatta cccggctaga 3660
tatcaatcac acatgcttat tggtcatggg tttgcatcac cgggtgattg tggtggcata 3720
cttagatgtc aacacggggt gataggaata atcactgctg gtggggaagg cttggttgca 3780
ttttcagaca ttagagacct gtatgcttat gaggaggaag ctatggagca gggcatttcc 3840
aactatattg agtcacttgg tgctgcattt ggtagtggat tcactcaaca aattggtgat 3900
aaagtttccg agctaaccag catggtaact agcaccatta cagagaagtt gcttaaaaac 3960
ttaatcaaaa ttatctcatc acttgtgatc attaccagga attatgagga cactaccaca 4020
gtgcttgcca ccctcgccct ccttgggtgc gacatctcac cgtggcagtg gctaaagaag 4080
aaggcatgtg acatcctgga aattccatac gccatcaaac aaggagatag ttggttgaag 4140
aaattcactg aggcatgtaa tgctgcaaag ggactggagt gggtgtccaa taagatatcc 4200
aaattcatta gttggttgca ggataaaatc atcccacaag cgagagacaa attagagttt 4260
gtcactaaac taaagcaatt agaaatgctt gaaaatcaga tttccaccat acaccaatct 4320
tgtccaagtc aagaacatca ggagatctta ttcaacaatg tgcggtggct atctatccag 4380
tccaagaggt ttgcaccact atatgcacat gaagctaaaa ggattcaaaa gctggagcat 4440
accataaata attacgtaca gttcaagagc aagcaccgta ttgagccagt atgtttgtta 4500

-continued gtacatggca gtccagggac aggaaaatca gttgcaacca atctaattgc tagagcaata 4560
gccgagaaag agaacacctc cacatactca ctgccacctg atccgtctca ctttgatggc 4620
tacaagcaac agggtgtggt tattatggat gacctaaacc aaaatccaga cggagcagac 4680
atgaaacttt tttgtcaaat ggtgtccact gtggagttta ttccaccgat ggcctcgcta 4740
gaagagaaag gcattttgtt cacatctaat tacgttttag cctccaccaa ctccagtcgg 4800
atcacaccac ccacggtggc tcacagtgat gcgctggcca ggagattcgc atttgacgtg 4860
gacatacaag tcatgagcga gtactccaga gacggaaagc tcaacatggc aatggctact 4920
gaaatgtgca aaaactgtca tcaaccagca aacttcaaaa gatgttgtcc tttagtgtgt 4980
ggcaaggcaa ttcagttaat ggataaatct tccagggtta gatacagcat tgatcagatc 5040
actacaatga ttgttaatga gagaaacaga agatcaaaca ttggtaattg catggaagct 5100
ctattccagg gaccactgca gtataaagat ctaaaaatag atgttaagac cagtcccccct 5160
ccggagtgta tcaacgattt gctccaggca gttgattccc aggaagtgag agattactgt 5220
gaaaagaaag gctggattgt taacattacc agtcaggttc aaacagagag gaacatcaac 5280
cgggcgatga ctatcctaca agcagtaact actttcgctg cagtagccgg tgtcgtgtac 5340
gttatgtaca agctgttcgc tgggcaccag ggtgcataca ctggtttgcc aaataaacga 5400
cccaatgtac ccactatcag gacagcaaaa gtgcaaggcc ctgggtttga ttacgcagtg 5460
gccatggcta aaagaaacat tgttacagca accaccagca aaggggagtt tacgatgttg 5520
ggagtctatg ataatgtggc catcttgcca acccacgcct cacctggtga aagcattgcg 5580
atcgacggta aagaggtgga aattcttgac gccaaagccc ttgaagatca ggcaggaact 5640
aatcttgaaa ttaccataat tacactaaag aggaacgaga agttcagaga tatcaggcca 5700
cacattccca cccaaatcac cgaaacaaat gatggagttt tgatcgtgaa cactagtaag 5760
taccccaaca tgtatgttcc cgttggtgct gtgaccgaac aggggtatct taatctcggt 5820
ggacgacaaa ccgctcgtac gctaatgtac aactttccaa ctagagcagg tcagtgtggt 5880
ggtgtcatca cgtgcactgg taaagtcatt gggatgcatg ttggtgggaa cggttcacat 5940
gggttcgcgg cggccctaaa gcggtcatac ttcactcaga ttcaaggtga gattcaatgg 6000
atgaaaccat caaaagaagt gggatacccg atcataaatg ctccgtccaa aaccaaactt 6060
gaacccagcg cttttcacta tgtgtttgaa ggggtgaagg aaccagcagt ccttaccaaa 6120
aatgatccca ggctcaggac agactttgaa gaagcaatat tctctaagta tgtaggcaac 6180
aagatcactg atgtggatga gtacatgaaa gaggcagtgg atcattacgc tggccaactc 6240
atgtctctag acatcaacac agaacaaatg tgcttggagg acgccatgta cggcaccgat 6300
ggcctggaag cacttgactt gaccactagt gctggatacc cttatgtagc aatgggaaag 6360
aaaaagagag acatcttgaa taagcagact agagacacca aggaaatgcg gagactctta 6420
gatacttatg gaattaactt accgcttgta acatatgtta aagatgaact aaggtcaaaa 6480
actaaggtgg agcagggaaa atccagattg attgaagcct ccagtttgaa tgattcagtg 6540
gccatgagaa tggcatttgg aaatctctat gcagcatttc acaaaaaccc aggagttgtc 6600
actggcagtg cagttggttg tgatccagat ctattttgga gcaagatccc agtgctaatg 6660
gaagagaagc tctttgcttt tgactacaca ggttatgatg catcactcag cccggcctgg 6720
tttgaggcac tcaaaatggt gctagagaaa atcggatttg gggacagggt ggattatatt 6780
gattacctca accattccca ccacctgtac aaaaacaaaa cttattgcgt aaaaggcggc 6840
atgccatctg gctgctcagg cacatcaatt tttaactcaa tgattaacaa cttaatcatt 6900

-continued

```
aggacactcc tactgaaaac ctacaagggc atagatttag atcacctaaa gatgattgcc   6960

tatggtgatg atgtaattgc ttcctacccc catgaggttg atgctagtct cctagcccaa   7020

tcaggaaaag actatggact aaccatgact ccagcagaca agtcagctac ctttgaaaca   7080

gtcacatggg agaatgtaac attcttgaaa agattcttta gagcggatga gaagtatccc   7140

ttcctcatac atccagtaat gccaatgaag gagattcatg aatcaattag atggacaaag   7200

gatcccagaa acacacagga tcacgtgcgc tcattgtgcc tattggcctg gcacaacggc   7260

gaagaagaat acaacaagtt cttagctaaa atcaggagtg tgccaattgg gagagcttta   7320

ttgctcccag agtactctac attgtaccgc cgttggctcg actcttttta gtaaccctac   7380

ctcagtcgaa ttggattggg tcatgctgtt gtaggggtaa atttttcttt aattcgggga   7440

aaaaaaaaaa aaaaaaaaaa aaaaaaaa                                      7468
```

COLD-ADAPTED-VIRAL-ATTENUATION (CAVA) AND NOVEL ATTENUATED POLIOVIRUS STRAINS

CROSS-REFERENCE TO RELATED APPLICATIONS

This application is a national phase entry under 35 U.S.C. § 371 of International Patent Application PCT/EP2015/063489, filed Jun. 16, 2015, designating the United States of America and published in English as International Patent Publication WO 2015/193324 A1 on Dec. 23, 2015, which claims the benefit under Article 8 of the Patent Cooperation Treaty to European Patent Application Serial No. 14176071.0, filed Jul. 8, 2014, and to U.S. Provisional Patent Application Ser. No. 62/013,379, filed Jun. 17, 2014.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

The application relates to the field of viral attenuation and the development of novel attenuated poliovirus strains for use as vaccines.

BACKGROUND

The Poliovirus (PV) belongs to the enterovirus genus within the Picornaviridae family. These small RNA viruses have a single-stranded positive-sense RNA genome and are non-enveloped. They are subdivided into three serotypes: PV1, PV2 and PV3. Infection with PV is usually asymptomatic; however, 1-2% of the cases result in paralytic poliomyelitis where viral-induced destruction of motor neurons causes paralysis, generally in limbs, termed Acute Flaccid Paralysis (AFP). Of these AFP cases, 5-10% are lethal as the virus spreads to regions of the brainstem resulting in respiratory arrest and, ultimately, death. (For reviews of PV and pathogenesis, see, for example, Minor 1999; Racaniello 2006; Pfeiffer 2010.)

Today, poliomyelitis is on the verge of eradication with only 406 and 359 cases worldwide in 2013 and 2014, respectively. There are two vaccines available that have enabled this successful battle against PV: the Inactivated Poliovirus Vaccine (IPV) (Salk 1953) and the Oral Poliovirus Vaccine (OPV) (Sabin 1956). IPV consists of three formalin-inactivated (killed) wild-type (neurovirulent) PV strains from each serotype (typically Mahoney, MEF-1 and Saukett for PV1, PV2 and PV3, respectively). OPV is made up of three live attenuated strains called Sabin 1, Sabin 2 and Sabin 3. The Sabin strains are named after Albert Sabin, who generated the strains through serial passage of three parental wild-type viruses through cell culture and even whole organisms (Sabin 1973). Due to the ease of administration and low costs of OPV (John 2009), it was heralded by the World Health Organization (WHO) and Global Polio Eradication Initiative (GPEI) as the vaccine of choice for the eradication program in 1988 (WHO 1988). However, the use of OPV is at odds with eradication and the end game strategy because the OPV vaccine strains display reversion of the attenuated phenotype to neurovirulent and transmissible polioviruses (Henderson, Witte et al. 1964). These Vaccine-Associated Paralytic Poliomyelitis (VAPP) cases occur with a frequency of one case per 500,000 vaccines (John 2004). Furthermore, circulating Vaccine-Derived Polioviruses (cVDPVs) result when the reverted vaccine viruses become transmissible within a susceptible population. As OPV is now recognized as a potential source of poliomyelitis through the VAPP and cVDPV phenomena, there has been a call for the use of OPV to be eliminated if complete eradication of poliomyelitis is to be achieved. In fact, over the last decade, regulatory authorities have recognized that OPV use must be ceased for eradication of poliomyelitis (WHO 2005). With IPV, the vaccine immunogens are formalin-inactivated, and, therefore, VAPP and cVDPV are not observed with the use of this vaccine. However, the 20-fold higher cost of this vaccine renders it unfavorable for use in low- and middle-income countries (Heinsbroek and Ruitenberg 2010; Zehrung 2010). To that end, the WHO and its many collaborators have initiated multiple projects for the development of strategies to make IPV safer and more economical (Zehrung 2010; Hawken and Troy 2012; Resik, Tejeda et al. 2013).

IPV is indeed a safer alternative to OPV with respect to VAPP and cVDPV; however, the wild-type viruses that make up the vaccine could pose a threat to the global population during the post-eradication era in the event of accidental escape of these viruses from a manufacturing facility. Furthermore, upon eradication, wild-type polioviruses will be subject to stringent bio-containment regulations, which may further increase the costs of goods of this already expensive vaccine (WHO 2006; Verdijk, Rots et al. 2011). In fact, the WHO already stipulates the destruction of any wild-type PV strains from laboratories across the globe. These actions will presumably be enforced more vigorously as eradication draws nearer (WHO 2009). Development of IPV vaccines based on attenuated strains is a safer vaccine manufacturing procedure and mitigates risks of potential disease outbreaks in the case of industrial accidents. To that end, the production of an IPV based on attenuated strains has been proposed as a strategy for the safe and economical production of IPV for the post-eradication era. Multiple attenuated strains have been proposed as a basis for a novel IPV vaccine, of which most research has been invested in making an IPV from the Sabin strains (Verdijk, Rots et al. 2011). Sabin-based IPV has recently undergone a successful Phase II clinical trial as a stand-alone vaccine (Liao, Li et al. 2012) and a Phase II and III trial in combination with diphtheria, tetanus and acellular pertussis (DTaP) (Okada, Miyazaki et al. 2013). Moreover, in Japan, a Sabin-based IPV has recently been licensed in combination with DTaP (Mahmood, Pelkowski et al. 2013). However, the capsids of the Sabin viruses differ significantly from the conventional IPV wild-type viruses, and, upon formalin inactivation, Sabin viruses display different antigenic properties required to raise neutralizing antibodies (and, therefore, protection) against PV infection. Indeed, it has been observed that the immune response to Sabin IPV is altered as compared to the one raised against conventional IPV; therefore, different dosing of the vaccine is necessary (Westdijk, Brugmans et al. 2011).

Several rationally engineered attenuated PV strains exist; however, their potential as IPV vaccine strains has, as of yet, not been fully explored. One set of such candidate attenuated strains is based on genetically stabilized Sabin strains as superior live vaccine strains as compared to the Sabin strains for a novel OPV development, as well as use for a basis of a novel IPV (e.g., Macadam et al. 2006; WO 2008/017870;

WO 2012/090000). These strains are capable of growth at physiological temperatures; however, they show significantly reduced infectivity at this temperature.

For the post-eradication era, there remains a need to develop an IPV based on safe, attenuated poliovirus strains, which do not revert to neurovirulent forms and which induce a similar immune response as conventional IPV based on wild-type strains.

BRIEF SUMMARY

This disclosure provides a novel method for developing recombinant attenuated poliovirus strains, as well as resulting novel recombinant attenuated poliovirus strains that can be used as a basis for an IPV. The attenuated backbone can be re-engineered to contain the wild-type capsids of strains used in current IPV vaccines, resulting in a wild-type antigenicity profile after inactivation while maintaining the attenuated phenotype during virus production and scale-up to produce a vaccine. The recombinant attenuated polioviruses are genetically stable under production conditions. Furthermore, due to their inability to replicate at 37° C., it is highly unlikely that they can revert to a neurovirulent form upon accidental ingestion, in the event of (un)intentional escape from a manufacturing facility. The recombinant attenuated poliovirus strains of this disclosure can be formalin-inactivated for use in an IPV vaccine.

The disclosure is directed to the general and preferred embodiments defined, respectively, by the independent and dependent claims appended hereto, which, for the sake of brevity, are incorporated by reference herein. Other preferred embodiments, features, and advantages of the various aspects of the disclosure will become apparent from the detailed description below, taken in conjunction with the appended figures.

In one embodiment, this disclosure provides a recombinant poliovirus strain that can be propagated in cell culture at 30° C. and that cannot be substantially propagated in cell culture at 37° C., comprising a capsid from a Mahoney, MEF-1, or Saukett strain.

In another embodiment, this disclosure provides a recombinant attenuated temperature-sensitive poliovirus type 1 strain that can be propagated in cell culture at 30° C. and cannot be substantially propagated in cell culture at 37° C.

In another embodiment, this disclosure provides a recombinant attenuated temperature-sensitive poliovirus type 2 strain that can be propagated in cell culture at 30° C. and cannot be substantially propagated in cell culture at 37° C.

In another embodiment, this disclosure provides a recombinant attenuated temperature-sensitive poliovirus type 3 strain that can be propagated in cell culture at 30° C. and cannot be substantially propagated in cell culture at 37° C.

In another embodiment, this disclosure provides a composition comprising a poliovirus strain and a pharmaceutically acceptable carrier or excipient, wherein the poliovirus strain is a recombinant attenuated temperature-sensitive poliovirus strain that can be propagated in cell culture at 30° C. and cannot be substantially propagated in cell culture at 37° C., and wherein the poliovirus strain can optionally comprise a capsid from a Mahoney, MEF-1, or Saukett strain.

In another embodiment, this disclosure provides a composition comprising first, second and third recombinant poliovirus strains, wherein each of the first, second and third recombinant poliovirus strains can be propagated in cell culture at 30° C. and cannot be substantially propagated in cell culture at 37° C., and wherein the first, second and third recombinant poliovirus strains respectively comprise a capsid from a Mahoney, an MEF-1, and a Saukett strain.

In another embodiment, this disclosure provides a composition comprising first, second and third recombinant poliovirus strains, further comprising a pharmaceutically acceptable carrier or excipient, wherein the first, second and third recombinant poliovirus strains can be propagated in cell culture at 30° C. and cannot be substantially propagated in cell culture at 37° C., and wherein the first, second and third recombinant poliovirus strains respectively comprise a capsid from a Mahoney, an MEF-1, and a Saukett strain.

In another embodiment, this disclosure provides an IPV composition, wherein the poliovirus in the composition is inactivated, and wherein prior to being inactivated, the poliovirus is a recombinant poliovirus strain that can be propagated in cell culture at 30° C. and that cannot be substantially propagated in cell culture at 37° C., and wherein the first, second and third recombinant poliovirus strains respectively comprise a capsid from a Mahoney, an MEF-1, and a Saukett strain.

In another embodiment, this disclosure provides an IPV composition, wherein the IPV composition comprises inactivated first, second and third recombinant poliovirus strains, wherein prior to being inactivated, each of the first, second and third recombinant poliovirus strains can be propagated in cell culture at 30° C. and cannot be substantially propagated in cell culture at 37° C., and wherein the first, second and third recombinant poliovirus strains respectively comprise a capsid from a Mahoney, an MEF-1, and a Saukett strain.

In another embodiment, this disclosure provides a combination vaccine composition comprising an IPV composition described supra, and one or more antigens from other pathogens, such as diphtheria, tetanus, pertussis, *Haemophilus influenzae* type b (Hib), Hepatitis B virus (HBV), etc.

In another embodiment, this disclosure provides a method for vaccinating against poliovirus infection and/or poliomyelitis, the method comprising administering to a subject a composition comprising an IPV composition described supra or a combination vaccine composition comprising an IPV as described supra.

In another embodiment, this disclosure provides a nucleic acid molecule comprising a sequence that codes for the genome or the complement of the genome of a poliovirus, wherein the poliovirus is a recombinant attenuated temperature-sensitive poliovirus that can be propagated in cell culture at 30° C. and cannot be substantially propagated in cell culture at 37° C., and wherein the recombinant attenuated temperature-sensitive poliovirus comprises a capsid from a Mahoney, MEF-1, or Saukett strain.

In another embodiment, this disclosure provides a method for preparing a preparation comprising a poliovirus, wherein the poliovirus is a recombinant attenuated temperature-sensitive poliovirus that can be propagated in cell culture at 30° C. and cannot be substantially propagated in cell culture at 37° C., and wherein the poliovirus can optionally comprise a capsid from a Mahoney, MEF-1, or Saukett strain, the method comprising:

a) infecting a cell in a cell culture with the poliovirus;
b) culturing the cells in the cell culture (at a temperature that is permissive for replication of the poliovirus, e.g., between about 20° C. and about 33° C.) to propagate the poliovirus; and
c) isolating the poliovirus strain from the cells or from the cell culture to obtain the preparation comprising the poliovirus.

In another embodiment, this disclosure provides a method for preparing a preparation comprising an inactivated poliovirus, wherein prior to being inactivated, the poliovirus is a recombinant attenuated temperature-sensitive poliovirus strain that can be propagated in cell culture at 30° C. and cannot be substantially propagated in cell culture at 37° C., and wherein the poliovirus can optionally comprise a capsid selected from a Mahoney, MEF-1, or Saukett strain, the method comprising:

a) infecting a cell in a cell culture with the poliovirus;
b) culturing the cells in the cell culture (at a temperature that is permissive for replication of the poliovirus, e.g., between about 20° C. and about 33° C.) to propagate the poliovirus;
c) isolating the poliovirus strain from the cells or from the cell culture to obtain the preparation comprising the poliovirus; and
d) inactivating the poliovirus.

In another embodiment, this disclosure provides a method for preparing an IPV comprising an inactivated poliovirus in a formulation suitable as a pharmaceutical composition, wherein prior to being inactivated, the poliovirus is a recombinant attenuated temperature-sensitive poliovirus strain that can be propagated in cell culture at 30° C. and cannot be substantially propagated in cell culture at 37° C., and wherein the poliovirus can optionally comprise a capsid selected from a Mahoney, MEF-1, or Saukett strain, the method comprising:

a) infecting a cell in a cell culture with the poliovirus;
b) culturing the cells in the cell culture (at a temperature that is permissive for replication of the poliovirus, e.g., between about 20° C. and about 33° C.) to propagate the poliovirus;
c) isolating the poliovirus strain from the cells or from the cell culture to obtain the preparation comprising the poliovirus;
d) inactivating the poliovirus; and
e) formulating the inactivated poliovirus into a pharmaceutical composition.

In another embodiment, this disclosure provides a method for obtaining a recombinant attenuated poliovirus strain that can be propagated in cell culture at 30° C. and that cannot be substantially propagated in cell culture at 37° C., the method comprising the steps of:

a) passaging a parental (or starting) poliovirus strain at ≤30° C. for sufficient passages to produce a virus with impaired growth at 37° C. (e.g., for at least 5, 10, 15, 20, 25, 30 or 35 passages);
b) isolating two or more different temperature-sensitive clones from the viral population that display impaired growth at 37° C.;
c) sequencing the genomes of the temperature-sensitive clones;
d) identifying mutations in the sequences of the genomes of temperature-sensitive clones by comparing the sequences of the temperature-sensitive clones to the sequence of the parental poliovirus strain;
e) synthesizing the recombinant attenuated poliovirus strain by combining mutations from two or more different temperature-sensitive clones into the genome of a (e.g., the parental or another) poliovirus strain; and
f) rescuing the recombinant attenuated poliovirus strain that can be propagated in cell culture at 30° C. and that cannot be substantially propagated in cell culture at 37° C.

In another embodiment, this disclosure provides a method for obtaining a recombinant attenuated poliovirus strain that can be propagated in cell culture at 30° C. and that cannot be substantially propagated in cell culture at 37° C., wherein the recombinant attenuated poliovirus strain can optionally comprise a capsid selected from a different poliovirus strain, the method comprising the steps of:

a) passaging a parental poliovirus strain at ≤30° C. for sufficient passages to produce a virus with impaired growth at 37° C.;
b) isolating two or more temperature-sensitive clones from the viral population that display impaired growth at 37° C.;
c) sequencing the genomes of the temperature-sensitive clones;
d) identifying mutations in the sequences of the genomes of temperature-sensitive clones by comparing the sequences of the temperature-sensitive clones to the sequence of the parental poliovirus strain;
e) synthesizing the recombinant attenuated poliovirus strain by combining mutations from the two or more different temperature-sensitive clones into the genome of a (e.g., the parental or another) poliovirus strain;
f) rescuing the recombinant attenuated poliovirus strain that can be propagated in cell culture at 30° C. and that cannot be substantially propagated in cell culture at 37° C.; and
g) optionally replacing the sequence coding for the capsid from the rescued recombinant attenuated poliovirus strain with a sequence coding for a capsid from a different poliovirus strain.

In certain embodiments, the sequence coding for the capsid from the rescued attenuated poliovirus strain is replaced with a sequence coding for a capsid from a Mahoney, MEF-1, or Saukett strain.

In certain embodiments, the sequence coding for the capsid from the rescued attenuated poliovirus strain is replaced with a sequence coding for a capsid from a Sabin type 1, Sabin type 2 or Sabin type 3 strain.

In another embodiment, this disclosure provides a method for obtaining a recombinant attenuated poliovirus strain that can be propagated in cell culture at 30° C. and that cannot be substantially propagated in cell culture at 37° C., wherein the recombinant attenuated poliovirus strain can optionally comprise a capsid selected from a Mahoney, MEF-1, or Saukett strain, the method comprising the steps of:

a) passaging a parental poliovirus strain at ≤30° C. for sufficient passages to produce a virus with impaired growth at 37° C.;
b) isolating two or more temperature-sensitive clones from the viral population that display impaired growth at 37° C.;
c) sequencing the genomes of the temperature-sensitive clones;
d) identifying mutations in the sequences of the genomes of temperature-sensitive clones by comparing the sequences of the temperature-sensitive clones to the sequence of the parental poliovirus strain;
e) synthesizing the recombinant attenuated poliovirus strain by combining mutations from the two or more different temperature-sensitive clones into the genome of a (e.g., the parental or another) poliovirus strain;
f) rescuing the recombinant attenuated poliovirus strain that can be propagated in cell culture at 30° C. and that cannot be substantially propagated in cell culture at 37° C.; and g) replacing the sequence coding for the capsid from the rescued recombinant attenuated poliovirus strain with a sequence coding for a capsid from a Mahoney, MEF-1, or Saukett strain.

In another embodiment, this disclosure provides a recombinant attenuated poliovirus strain obtainable by the methods described supra.

BRIEF DESCRIPTION OF THE DRAWINGS

FIG. 1: Schematic representation for a method of attenuating a poliovirus strain by Cold-Adapted-Viral-Attenuation (CAVA) to produce a recombinant attenuated poliovirus strain (CAVA-$PV_{Backbone}$). A representative line graph shows growth at 37° C. for a parental or starting poliovirus strain and three different temperature-sensitive clones. The parental virus is shown as filled circles and the three temperature-sensitive clones are shown as empty diamonds, empty circles, and empty squares.

FIG. 4A illustrates growth at 30° C.; FIG. 4B represents growth at 37° C.; and FIG. 4C shows growth at 39.5° C. Brunenders parental PV is shown as filled triangles and CAVA-$PV_{Backbone}$ is shown as open circles.

FIG. 5A shows growth at 30° C.; FIG. 5B illustrates growth at 37° C.; and FIG. 5C represents growth at 39.5° C. Brunenders parental PV is shown as filled triangles and CAVA-$PV_{Backbone}$ is shown as open circles.

FIG. 6A represents growth at 30° C.; FIG. 6B shows growth at 37° C.; and FIG. 6C illustrates growth at 39.5° C. Brunenders parental PV is shown as filled triangles and CAVA-$PV_{Backbone}$ is shown as open circles.

Mahoney at 37° C., (Panel C) CAVA-$PV_{Mahoney}$ at 37° C., and (Panel D) CAVA-$PV_{Mahoney}$ at 30° C.

Figure 19:
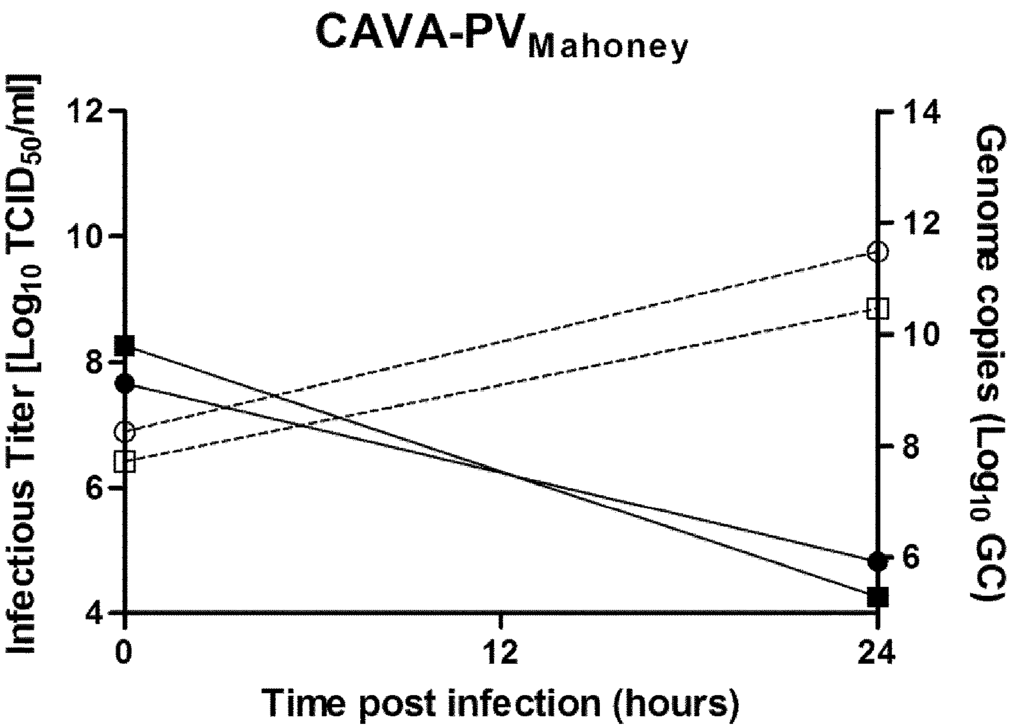

FIG. 19: CAVA-$PV_{Mahoney}$ infection over time in viral RNA levels as measured by qPCR expressed as genome copies ($Log_{10}$ GC on Right Y-axis, circles) and infectious units as measured by titration ($Log_{10}$ $TCID_{50}$/ml on Left-Y axis, squares) during infection at (open square and circle) 30° C. and (filled square and circle) 37° C.

Figure 20:
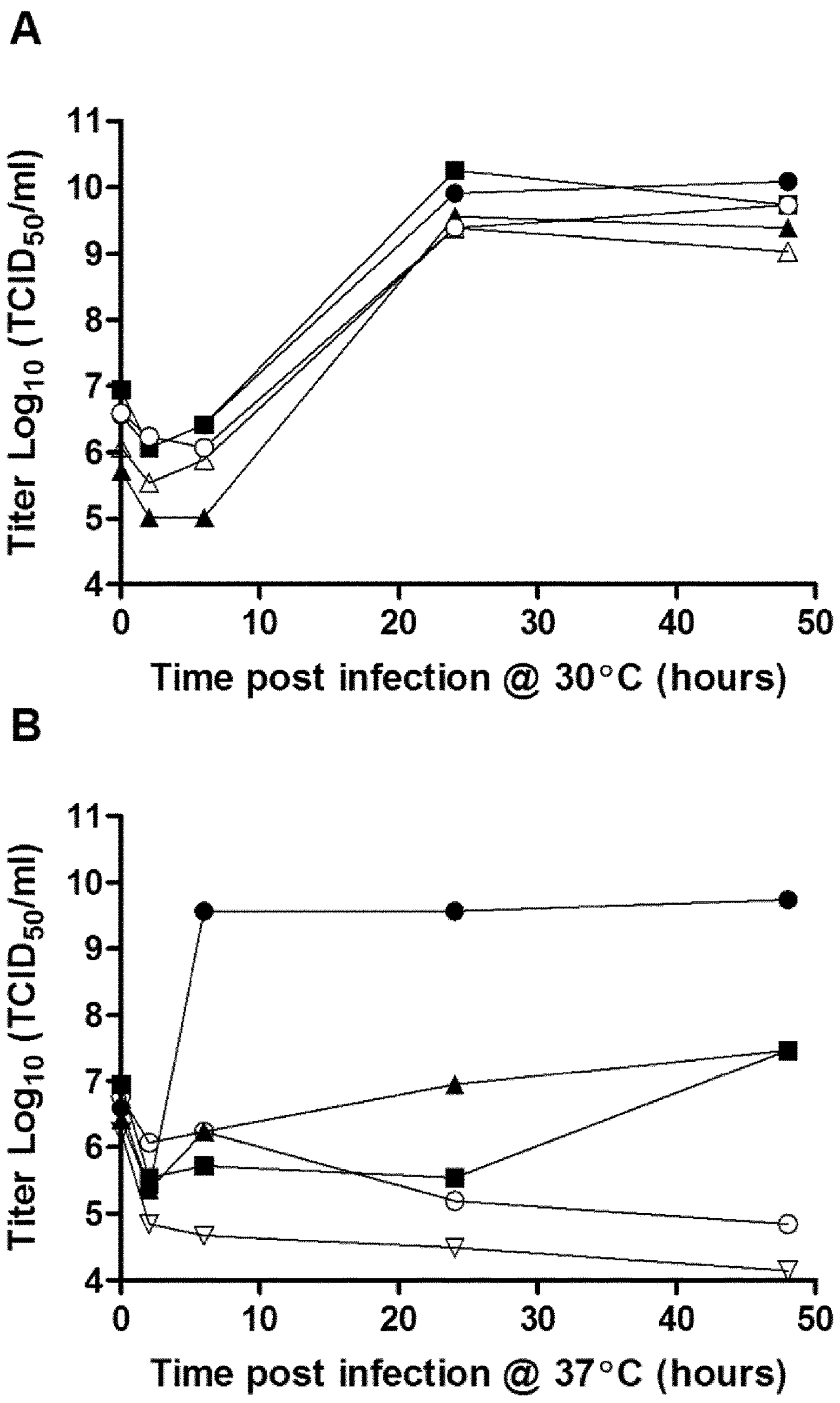

FIG. 20: Replication kinetics of parental Brunenders, CAVA-$PV_{Backbone}$ of Example 1, CAVA-$PV_{Mahoney}$ of Example 6 and two intermediate viruses with either the seven CAVA mutations in the 5'UTR or the 17 CAVA mutations in the Non-Structural proteins. Panel A shows growth at 30° C. and Panel B shows growth at 37° C. Data for Brunenders parental strain are shown as filled circles, data for the intermediate virus with seven CAVA mutations in the 5'UTR are shown as filled triangles, data for the intermediate virus with 17 CAVA mutations in the Non-Structural proteins are shown as filled squares, data for CAVA-$PV_{Backbone}$ of Example 1 are shown as open circles, and data for CAVA-$PV_{Mahoney}$ are shown as open triangles.

DETAILED DESCRIPTION

In this disclosure, a novel method of Cold-Adapted-Viral-Attenuation (CAVA) was used to produce recombinant attenuated poliovirus strains, Cold-Adapted-Viral-Attenuation Poliovirus (CAVA-PV). A CAVA-PV grows to high titers at low temperature (30° C.), but does not grow substantially at physiological temperature (37° C.). Due to the inability to replicate substantially at 37° C., CAVA-PV strains encounter a non-permissive temperature when inside a mammalian host, thus conferring an attenuated phenotype suitable for use as the basis for an IPV vaccine. The CAVA-PV genomic backbone is suitable for re-engineering to contain sequences coding for different virus capsids (e.g., the three wild-type capsids used in conventional IPV), thus conferring the antigenic, and, therefore, presumably the same immunogenic, profile of the conventional vaccine while maintaining the attenuated phenotype of CAVA-PV. Furthermore, formalin-inactivated recombinant attenuated poliovirus strains of this disclosure can be used as an IPV providing a similar immune response compared to marketed conventional IPV vaccines, while the risks of VAPP and cVDPV are eliminated.

As defined herein, "does not grow substantially," "inability to replicate substantially," "no substantial replication," and "cannot be substantially propagated" means that the increase in the number of infectious units of the virus compared to the theoretical input/inoculum (based on calculated MOI) is not more than 10%, or preferably not more than 5%, or more preferably not more than 1%, or even more preferably there is no measurable increase in the number of infectious units for the virus. The assay to measure/titrate viral infectious units ($TCID_{50}$ assay) has a limit of detection of 1.7 $Log_{10}$ $TCID_{50}$/ml. In certain embodiments, "does not grow substantially," "inability to replicate substantially," "no substantial replication," and "cannot be substantially propagated" is defined as no measurable increase in viral RNA (genome copies) as compared to the theoretical input/inoculum (calculated genome copies) as measured by quantitative Reverse Transcription PCR (RT-qPCR). In certain embodiments, "does not grow substantially," "inability to replicate substantially," "no substantial replication," and "cannot be substantially propagated" is defined as the lack of visual signs of infection (cytopathic effect) as observed by light microscopy or the lack of visual signs of infection (dead or apoptotic cells with virus-induced membrane vesicles or virus lattices) by Electron Microscopy (EM).

As defined herein, "recombinant" means that the nucleic acid molecule coding for the poliovirus has undergone a molecular biological manipulation combining genetic constituents from two or more different sources, e.g., different clones, different strains, or different organisms. The recombinant attenuated polioviruses of this disclosure can be generated by molecular DNA cloning or can be chemically synthesized (de novo DNA synthesis), by techniques that are well known and common practice for those skilled in the art. This could even be done by providing the desired recombinant sequence information to a contract manufacturer (e.g., GenScript®, GeneArt®, and BaseClear), which can then produce these molecules according to routine techniques. Any standard manual on DNA technology provides detailed protocols that can be used to produce the recombinant PV strains of this disclosure. Brief, exemplary instructions for the construction of such recombinant viruses are provided below in the Examples.

As defined herein, "attenuated" means that the virulence of the poliovirus has been reduced such that the poliovirus is less pathogenic compared to a parental or starting virus but it is still viable. For instance, an attenuated poliovirus of the disclosure is significantly less neurovirulent compared to wild-type strains and, therefore, has significantly decreased, if any, capability for causing paralysis. In particular, a preferred attenuated virus strain of this disclosure would be safe for use as a vaccine strain, not only when administered in an inactivated form, as intended, but even in the case of accidental infection and/or escape from a manufacturing facility. In certain preferred embodiments, an attenuated virus of this disclosure has a $(P)LD_{50}$ of greater than $1\times10^7$ $TCID_{50}$ when administered by intra cerebral (i.c.) administration in CD155 transgenic mice.

As used herein, the phrase "nucleotide," "nucleic acid" or "nucleic acid molecule" refers to DNA and RNA, as well as any of the known base analogs of DNA and RNA or chimeras formed therefrom. Thus, a "nucleotide," "nucleic acid" or a "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single-stranded form or a double-stranded helix. Double-stranded DNA-DNA, DNA-RNA and RNA-RNA helices are possible. The term "nucleic acid molecule" and, in particular, "DNA or RNA molecule," refers only to the primary and secondary structure of the molecule, and does not limit it to any particular tertiary forms. Thus, the term includes double-stranded DNA found in linear or circular DNA molecules (e.g., restriction fragments or plasmids), as well as single-stranded positive-sense RNA molecules of the poliovirus genome and fragments thereof. In discussing the structure of particular double-stranded DNA molecules or single-stranded RNA molecules, sequences may be described herein according to the normal convention of giving the sequence in the 5' to 3' direction along the single-stranded positive-sense RNA molecules of the poliovirus genome or the non-transcribed strand of DNA (i.e., the strand having a sequence homologous to the mRNA).

The Brunenders poliovirus strain was used as a parental strain for the production of CAVA-$PV_{Backbone}$. The Brunenders strain is of serotype 1 and was originally derived from a clinical isolate called the Brunhilde strain. Passaging the Brunhilde strain through twelve serial passages in tissue culture of human origin by Dr. John Enders in 1956 resulted in the Brunenders strain. This strain has been shown to be partially attenuated (Enders 1952; Sanders, Liu et al. 2015). A representative sequence of the Brunenders strain is provided as SEQ ID NO:1. This Brunenders strain was used as the parental strain for this disclosure but some natural variation is common in a virus population.

It is also shown herein that a CAVA-PV strain can also be prepared using MEF-1 (a type 2 PV that is wild-type and neurovirulent) or Sabin 3 (an attenuated type 3 PV) as parental strains, showing the general applicability of the disclosure to create CAVA-PV strains that have the phenotype of significant growth at 30° C. and no substantial growth at 37° C. A representative sequence of the MEF-1 strain is provided as SEQ ID NO:5 and Sabin 3 as SEQ ID NO:8. It will be clear to the skilled person that the mutations inducing the temperature-sensitive phenotype are not serotype-specific and, therefore, other poliovirus strains, such as, for example, Mahoney or Saukett strains, can also be used as the parental strains for creating further CAVA-PV strains with the phenotype of the disclosure, according to the teachings provided herein.

As defined herein, a "parental strain" or "starting strain" can be a wild-type strain circulating in or isolated from nature, a known standard laboratory strain, or any other poliovirus strain that has not already been subjected to the CAVA method of this disclosure. Non-limiting examples of parental strains are Brunenders, MEF-1, Mahoney, Saukett, Sabin 1, Sabin 2 or Sabin 3 strains. Representative examples of sequences are provided for these strains herein as follows: Brunenders (SEQ ID NO:1), MEF-1 (SEQ ID NO:5), Mahoney (SEQ ID NO:6), Saukett (SEQ ID NO:7), Sabin 3 (SEQ ID NO:8), Sabin 1 (SEQ ID NO:9) and Sabin 2 (SEQ ID NO:10).

The disclosure also provides a method for obtaining a recombinant attenuated poliovirus strain that can be propagated in cell culture at 30° C. and that cannot be substantially propagated in cell culture at 37° C., comprising the steps of: a) passaging a (parental) poliovirus strain at a temperature of ≤32° C. for sufficient passages to produce a virus with impaired growth at 37° C.; b) isolating two or more (e.g., two, three, four, five, or more) different temperature-sensitive clones that display impaired growth at 37° C.; c) sequencing the genomes of the temperature-sensitive clones, d) identifying mutations in the sequences of the genomes of temperature-sensitive clones by comparing the sequences of the temperature-sensitive clones to the sequence of the parental poliovirus strain; e) synthesizing the recombinant attenuated poliovirus strain by combining mutations from two or more different temperature-sensitive clones into the genome of the parental poliovirus strain or into the genome of another poliovirus strain; and f) rescuing the recombinant attenuated poliovirus strain that can be propagated in cell culture at 30° C. and that cannot be substantially propagated in cell culture at 37° C. The passaging in step a) is preferably performed by infecting at a low multiplicity of infection (MOI), e.g., at an MOI between 0.0001 and 1, e.g., between 0.001 and 0.1, e.g., at about 0.01. The temperature for passaging in step a) is 32° C. or less, e.g., between about 20° C. and 31° C., e.g., between about 24° C. and 30° C., e.g., at about 30° C. Any cell line that is permissive to poliovirus growth at this temperature can be used, e.g., Vero, PER.C6®, and HEK293, etc. The skilled person will appreciate that the number of passages that is required is not critical and can be conveniently determined by screening for a phenotype of impaired growth at 37° C. in clones of a dissected viral population, as mutations that would contribute to a cold-adapted phenotype can accumulate at any passage. After a limited number of passages, such a phenotype may already be observed, and if not, further passaging may increase the chance of finding clones with this phenotype. Hence, in certain embodiments, the number of passages in step a) can be at least 5, at least 10, at least 15, at least 20, at least 25, at least 30, or more. As used herein, "impaired growth" at 37° C. is defined as at least 10-fold, e.g., 100- to 1000-fold, reduction in maximum titer compared to wild-type virus. In addition, clones with impaired growth also may display slower growth, i.e., longer infection time required to reach the maximum titer, as compared to a wild-type or parental virus. In certain embodiments, growth kinetics of the temperature-sensitive clones at lower temperature (e.g., 30° C.) may be faster as compared to the starting (parental) strain. In one embodiment, to develop a CAVA-PV, the Brunenders parental strain was serially passaged on PER.C6® cells more than 30 times at low temperature (≤30° C.) and at low MOI (e.g., 0.01). The resulting virus population was dissected to identify temperature-sensitive viral clones in the population with impaired growth at physiological temperatures (37° C.) and wild-type growth at low temperature (30° C.). Three temperature-sensitive clones (which showed impaired growth at 37° C. as well as faster growth kinetics at 30° C. compared to the parental Brunenders strain) were found by screening of approximately 1000 clones in the viral population at 37° C.

The three temperature-sensitive clones were sequenced and a total of 31 mutations were found across the three different clones. Each clone had 18 nucleotide mutations of which some were shared among the different clones and some were unique per clone. These mutations were identified in three of the four different regions of the PV genome, including the 5'UTR (untranslated region), the capsid, and the non-structural proteins. No mutations were identified in 3'UTR. The 5'UTR contains a cloverleaf structure that is necessary for linkage of the genome to the VpG protein (2B) to form an infectious virion and encapsidation of the RNA into the capsid. The remainder of the 5'UTR is the IRES (Internal Ribosomal Entry Site), which is essential for translation of the viral RNA. As the region does not encode any proteins (untranslated), the element performs its function by directly binding its interacting RNA/protein counterparts; therefore, the secondary structure of this domain is important for its function. The capsid region encodes the outer surface of the viral particle and can be subdivided into four proteins, which make up this exterior of the virion, known as the capsid. These four proteins are termed VP1, VP2, VP3 and VP4. The non-structural proteins are subdivided into proteins 2A, 2B, 2C, 3A, 3B, 3C, and 3D. The proteins are required for viral replication, polyprotein processing, translation and interactions with host cell components for successful infection. For example, the 2A protease shuts off host cell protein translation via cleavage of eIF4G (Skern and Liebig 1994). The 3'UTR is also an untranslated region required for initiation of complementary strand synthesis. As with the 5'UTR, the structure of the element enables its function.

The 31 mutations identified across the three clones included seven mutations in the IRES, seven mutations in the capsid, and 17 mutations in the non-structural proteins. A first CAVA-$PV_{Backbone}$ was developed by combining all 31 mutations in the Brunenders wild-type background (and thus the first developed CAVA-PV is a Type 1 poliovirus). See Example 1, Table 1, for the 31 mutations that were combined to produce this CAVA-$PV_{Backbone}$. Also see FIG. 1 for a schematic overview of the CAVA method and how the CAVA-$PV_{Backbone}$ was generated.

The combination of the 31 mutations in one virus genome had a synergistic effect. The CAVA-$PV_{Backbone}$ exhibited an accumulative temperature sensitivity compared to the three individual clones, by showing no substantial replication at 37° C. in sPER.C6 cells. On the contrary, in the same cells, at 30° C., CAVA-$PV_{Backbone}$ showed similar growth kinetics, or even faster growth, compared to the Brunenders parental strain and other PV1 strains (Example 2, FIGS. 2 and 3). The growth characteristics for CAVA-$PV_{Backbone}$ were subsequently tested in various other mammalian cell lines and the inability of CAVA-$PV_{Backbone}$ to replicate at physiological temperature of 37° C. was confirmed in all the mammalian cell types that were tested (Example 3, FIGS. 4A-9).

The synthetic combination of mutations found in the clones is deemed essential for obtaining the CAVA-PV phenotype (i.e., similar growth at 30° C. as compared to the parental Brunenders strain and inability to replicate at 37° C.). Selection of a virus with a complete loss of replication at 37° C. was not possible by serial passage of Brunenders and MEF-1 for more than 30 passages at low temperature. In fact, only two to three out of approximately 1000 screened clones obtained during passage of Brunenders and MEF-1 showed impairment of growth at 37° C. (FIG. 1), while increased growth at 30° C. as compared to the parental strain was observed in clones after passage of Brunenders and MEF-1. Therefore, the passaging conditions used here offered a selective advantage for improved growth at 30° C. but did not favor selection of viruses with impaired replication at 37° C. Only upon synthetic combination of the mutations found in three individual clones into the Brunenders genome was the CAVA phenotype observed. Interestingly, the CAVA-PV strains did not display better growth as compared to the parental strain at 30° C. (FIG. 3), which was observed with the clones. Therefore, natural combination of these CAVA mutations during passage at 30° C. (which are necessary for the CAVA phenotype) would be disadvantageous compared to the starting clones and are, therefore, unlikely to occur spontaneously. This accentuates the prerequisite for synthetic combination of observed mutations to achieve the CAVA phenotype.

Thus, in certain particular embodiments, this disclosure provides a recombinant attenuated poliovirus strain that can be propagated in cell culture at 30° C. and that cannot be substantially propagated in cell culture at 37° C., wherein the genome of the recombinant attenuated poliovirus strain comprises mutations at at least 15, 16, 17, 18, 19, 20, 21, 22, 23, 24, 25, 26, 27, 28, 29, 30 or 31 of the following positions as compared to the genome of a Brunenders strain (SEQ ID NO:1): 133 (A), 142 (U), 146 (G), 163 (A), 579 (G), 597 (C), and 609 (G) in the 5'UTR; 805 (A), 1787 (C), 1905 (U), 2756 (U), 3236 (C), 3323 (C), and 3376 (A) in the capsid; and 3476 (C), 3486 (G), 3852 (A), 4120 (U), 4253 (C), 4301 (U), 4428 (A), 4563 (A), 4811 (A), 5436 (G), 5705 (A), 6059 (C), 6210 (A), 6488 (C), 6848 (G), 7079 (U), and 7102 (U) in the non-structural proteins (the nucleotide in the parental strain is indicated between brackets after its position, and thus this is mutated into a different nucleotide in this embodiment). In certain particular embodiments thereof, the genome of the recombinant attenuated poliovirus strain comprises at least 15, 16, 17, 18, 19, 20, 21, 22, 23, 24, 25, 26, 27, 28, 29, 30 or 31 of the following mutations compared to the genome of a Brunenders strain (SEQ ID NO:1): 133 (A to G), 142 (U to C), 146 (G to A), 163 (A to G), 579 (G to A), 597 (C to U), and 609 (G to A) in the 5'UTR; 805 (A to C), 1787 (C to U), 1905 (U to C), 2756 (U to C), 3236 (C to U), 3323 (C to U), and 3376 (A to G) in the capsid; and 3476 (C to U), 3486 (G to A), 3852 (A to U), 4120 (U to C), 4253 (C to U), 4301 (U to C), 4428 (A to G), 4563 (A to U), 4811 (A to G), 5436 (G to A), 5705 (A to G), 6059 (C to U), 6210 (A to G), 6488 (C to U), 6848 (G to A), 7079 (U to C), and 7102 (U to C) in the non-structural proteins.

In addition, in a transgenic CD155 mouse model (Koike, Taya et al. 1991) used to evaluate poliovirus neurovirulence in vivo, the CAVA-PV was shown to be highly attenuated (Example 4, Table 2). In fact, not one mouse infected with the highest possible dose of the CAVA-PV showed any paralysis or any other signs of disease. This is not the case for Sabin 1, a known attenuated PV strain that was also included in the test. In decreasing order of virulence, the strains tested in the neurovirulence mouse model were Mahoney, Brunhilde, Saukett, Brunenders, Sabin 1-3 and CAVA-PVs. It was determined that CAVA-PVs are at least 100 times more attenuated than Brunenders, which is a partially attenuated strain, and at least as attenuated as the Sabin strains, which are well-known attenuated strains that are widely used in many countries for oral vaccination against poliomyelitis.

Furthermore, by re-engineering a CAVA-PV backbone to contain capsids from different poliovirus strains, CAVA-PV is suitable for use as an attenuated vaccine strain for development of IPV with an antigenic profile of the currently used wild-type IPV vaccines but with an attenuated CAVA-PV phenotype. For example, a CAVA-PV is suitable for use as an attenuated backbone for production of attenuated polioviruses containing the capsids of virulent wild-type PV strains (types 1, 2 and 3, e.g., the type 1 strain Mahoney, type 2 strain MEF-1, and type 3 strain Saukett). This can, for instance, be done by replacing the capsid sequence from a CAVA-PV strain with a desired capsid sequence using routine molecular biology technology (see, e.g., WO 2012/090000 for examples of re-engineering the capsids of attenuated PV strain backbones to those of wild-type strains; however, in the referenced case, the resulting strains are still capable of substantial replication at 37° C., in contrast to the CAVA-PV strains of the instant disclosure). Thus, a CAVA-PV can be used to produce recombinant attenuated polioviruses for IPV. Preferably, a CAVA-PV is engineered to contain the same capsid sequences as the wild-type IPV strains that have been used to successfully immunize the global population since 1952. This will circumvent an altered antigenic (and, therefore, presumed immunogenic) profile from other attenuated strains for IPV, as has been observed for the Sabin strains, upon formalin inactivation. In particularly preferred embodiments therefor, a CAVA-PV is used as the backbone, and the sequence coding for the capsid is exchanged for the sequence coding for the capsid from a Mahoney, MEF-1, or Saukett strain. This results in recombinant poliovirus strains that can be propagated in cell culture at 30° C. and that cannot be substantially propagated in cell culture at 37° C., comprising a capsid from a Mahoney, a MEF-1 or a Saukett strain, respectively. In alternative preferred embodiments, mutations that cause the CAVA-PV phenotype (e.g., at least 10, 11, 12, 13 or 14 of the mutations shown in Table 4 for the Brunenders background strain) are engineered into the corresponding positions of parental Mahoney, MEF-1 or Saukett strains, which will result in, respectively, Mahoney, MEF-1 or Saukett strains (which thus have the original capsids of such strains) that can be propagated in cell culture at 30° C. and that cannot be substantially propagated in cell culture at 37° C. This disclosure also provides such methods and poliovirus strains obtainable thereby. Such strains can also be used to swap capsids, e.g., a MEF-1 strain that has already been mutated to contain the mutations leading to the CAVA-PV phenotype (growth at 30° C., no substantial growth at 37° C., FIG. 11) can be used as a basis to swap the MEF-1 capsid for a Mahoney or Saukett capsid by further genetic engineering.

As described in Example 6 below, the sequences coding for the capsids from Mahoney, MEF-1 and Saukett were placed into the background of the CAVA-PV genome by replacing the sequence coding for the CAVA-PV capsid, which corresponds to the capsid of the parental Brunenders strain (nucleotides 747 to 3389 of SEQ ID NO:1). The resulting vaccine strains are CAVA-$PV_{Mahoney}$, CAVA-$PV_{MEF\text{-}1}$ and CAVA-$PV_{Saukett}$, which contain the Mahoney, MEF-1 and Saukett capsids, respectively. As described in Example 7, the growth kinetics of CAVA-$PV_{Mahoney}$, CAVA-$PV_{MEF\text{-}1}$ and CAVA-$PV_{Saukett}$ in the suspension PER.C6® (sPER.C6) cells, a suitable production cell line, were all compared to the growth of the Brunenders parental strain. The CAVA-$PV_{Mahoney}$, CAVA-$PV_{MEF\text{-}1}$ and CAVA-$PV_{Saukett}$ strains all showed growth kinetics that were similar to that of the parental Brunenders strain at 30° C. On the contrary, at 37° C., the CAVA-$PV_{Mahoney}$, CAVA-$PV_{MEF\text{-}1}$ and CAVA-$PV_{Saukett}$ strains showed no substantial replication. These same growth kinetics were observed for the first CAVA-$PV_{Backbone}$ without capsid exchange, demonstrating that the temperature sensitivity of the viruses lies within the mutations outside of the capsid region.

Thus, in certain embodiments, this disclosure provides a recombinant attenuated poliovirus strain that can be propagated in cell culture at 30° C. and that cannot be substantially propagated in cell culture at 37° C., wherein the genome of the recombinant attenuated poliovirus strain comprises mutations at at least 15, 16, 17, 18, 19, 20, 21, 22, 23 or 24 of the following positions as compared to the genome of a Brunenders strain (SEQ ID NO:1): 133 (A), 142 (U), 146 (G), 163 (A), 579 (G), 597 (C), and 609 (G) in the 5'UTR; and 3476 (C), 3486 (G), 3852 (A), 4120 (U), 4253 (C), 4301 (U), 4428 (A), 4563 (A), 4811 (A), 5436 (G), 5705 (A), 6059 (C), 6210 (A), 6488 (C), 6848 (G), 7079 (U), and 7102 (U) in the non-structural proteins (the nucleotide in the parental strain is indicated between brackets after its position, and, thus, this is mutated into a different nucleotide in this embodiment). In certain particular embodiments thereof, the genome of the recombinant attenuated PV strain comprises at least 15, 16, 17, 18, 19, 20, 21, 22, 23 or 24 of the following mutations compared to the genome of a Brunenders strain (SEQ ID NO:1): 133 (A to G), 142 (U to C), 146 (G to A), 163 (A to G), 579 (G to A), 597 (C to U), and 609 (G to A) in the 5'UTR; and 3476 (C to U), 3486 (G to A), 3852 (A to U), 4120 (U to C), 4253 (C to U), 4301 (U to C), 4428 (A to G), 4563 (A to U), 4811 (A to G), 5436 (G to A), 5705 (A to G), 6059 (C to U), 6210 (A to G), 6488 (C to U), 6848 (G to A), 7079 (U to C), and 7102 (U to C) in the non-structural proteins. In certain embodiments, the capsid of such strains as compared to the Brunenders capsid has been replaced with a capsid from a Mahoney, MEF-1, or Saukett strain. Representative capsid amino acid sequences are provided here as Mahoney (SEQ ID NO:2), MEF-1 (SEQ ID NO:3), and Saukett (SEQ ID NO:4), and, of course, the skilled person is aware that some natural variation is common in a virus population.

It will also be apparent to those of skill in the art that the mutations identified here for CAVA-PV can be extrapolated to other poliovirus strains because there is a relatively high degree of homology between the genomes of many of the different types of PV strains. Thus, the positions corresponding to the mutations in CAVA-PV can be identified in different strains of poliovirus by aligning the genomic sequences of the different strains. In fact, an alignment has been made containing examples from all three poliovirus serotypes (Toyoda, Kohara et al. 1984). In this way, the attenuated phenotype of CAVA-PV can be transferred to other strains to produce an attenuated CAVA-PV phenotype in new and different backbones. For example, it was determined that of the 31 mutations in CAVA-PV, 11 are unique in CAVA-PV and the parental Brunenders nucleotide at those positions are conserved in all other PV strains used for the alignment (e.g., nucleotide 142 is a C (cytidine) in CAVA-PV, but the nucleotide at that position is a U (uridine) in the Brunenders parental strain and the Brunhilde, Mahoney, Sabin 1, Sabin 2, Sabin 3, MEF-1, and Saukett strains). Furthermore, there are six other mutations in CAVA-PV for which the parental Brunenders nucleotide at those positions are conserved in all of the PV1 strains used for the alignment (Brunenders, Brunhilde, Mahoney and Sabin 1). There is also one mutation that is common in CAVA-PV and Sabin 1, but the nucleotide at that position is conserved in all other strains. In addition, there are six mutations in CAVA-PV at positions that are not conserved in the other strains used for the alignment.

Based on the analysis of all of the CAVA-PV mutations, 14 mutations were identified that would likely provide a strong contribution to the temperature-sensitive (and, therefore, attenuated) phenotype of CAVA-PV. The 14 mutations are shown in Table 4 (see also Example 10 below). The mutations were selected based on the following criteria: a) conservation among other PV strains; b) experimental evidence based on reversion in the clones after passage at 37° C.; c) novel mutations in clones compared to preceding intermediate passage populations that were still capable of growing at 37° C.; and d) mutations that cause amino acid changes in essential RNA structures (i.e., the IRES). The 14 mutations were engineered into different poliovirus background strains. Thus, a CAVA-PV of this disclosure may comprise the 14 mutations in Table 4. A CAVA-PV of this disclosure may also comprise the 14 mutations in Table 4 and, optionally, one more of the other 17 mutations in the first identified CAVA-$PV_{Backbone}$. A CAVA-PV of the disclosure may also comprise the 14 mutations in Table 4 and, optionally, other mutations in the genome compared to a wild-type strain. A CAVA-PV of this disclosure may also comprise the 14 mutations in Table 4 and, optionally, may also comprise a capsid from a Mahoney MEF-1, or Saukett strain. It will also be clear that it is possible for the skilled person, using the teachings herein, to make further CAVA-PV strains that have only a subset of the 14 mutations of Table 4 (e.g., 8, 9, 10, 11, 12 or 13 of these, either in the Brunenders background strain or on corresponding positions in other PV background strains) and test such strains for the CAVA-PV phenotype and, in such way, potentially obtain additional CAVA-PV strains.

Thus, in certain embodiments, this disclosure provides a recombinant attenuated poliovirus strain that can be propagated in cell culture at 30° C. and that cannot be substantially propagated in cell culture at 37° C., wherein the genome of the recombinant attenuated poliovirus strain comprises mutations at at least 10, 11, 12, 13 or 14 of the following positions as compared to the genome of a Brunenders strain (SEQ ID NO:1): 133 (A), 142 (U), 163 (A), 597 (C), and 609 (G) in the 5'UTR; and 3486 (G), 3852 (A), 4120 (U), 4428 (A), 4563 (A), 5436 (G), 6210 (A), 6848 (G), and 7102 (U) in the non-structural proteins (the nucleotide in the parental strain is indicated between brackets after its position and, thus, this is mutated into a different nucleotide in this embodiment). In certain particular embodiments thereof, the genome of the recombinant attenuated PV strain comprises at least 10, 11, 12, 13 or 14 of the following mutations as compared to the genome of a Brunenders strain (SEQ ID NO:1): 133 (A to G), 142 (U to C), 163 (A to G), 597 (C to U), and 609 (G to A) in the 5'UTR; and 3486 (G to A), 3852 (A to U), 4120 (U to C), 4428 (A to G), 4563 (A to U), 5436 (G to A), 6210 (A to G), 6848 (G to A), and 7102 (U to C) in the non-structural proteins. In certain preferred embodiments, the capsid of such strains has been replaced with a capsid from a Mahoney, MEF-1, or Saukett strain.

The recombinant attenuated poliovirus strain of this disclosure may also be derived from a poliovirus strain other than the Brunenders strain (e.g., Brunhilde, Mahoney, Sabin 1, Sabin 2, Sabin 3, MEF-1, or Saukett strain, or strains derived from any of these, or other strains) by transferring the mutations from CAVA-PV to the homologous nucleotides in the genome of the other poliovirus strain. Furthermore, the recombinant attenuated poliovirus strain of this disclosure may be derived from a poliovirus strain other than the Brunenders strain and optionally comprise a capsid from a different poliovirus strain. As PV strains show some variation in their genome lengths, the exact nucleotide position of a mutation can vary upon alignment of the various PV sequences. Therefore, the CAVA mutations differ slightly in nucleotide number when extrapolated from the Brundeners background to the MEF-1 strain or other poliovirus strains, according to how the sequences align. The corresponding nucleotide positions of CAVA mutations for the Mahoney (PV1), MEF-1 (PV2), Saukett (PV3), Sabin 1 (PV1), Sabin 2 (PV2) and Sabin 3 (PV3) strains, as compared to the numbering for the Brunenders strain, are provided herein (Table 4).

Thus, as a further non-limiting example in certain embodiments, this disclosure provides a recombinant attenuated poliovirus strain that can be propagated in cell culture at 30° C. and that cannot be substantially propagated in cell culture at 37° C., wherein the genome of the recombinant attenuated poliovirus strain comprises mutations at at least 10, 11, 12, 13 or 14 of the following positions as compared to the genome of a MEF-1 strain (SEQ ID NO:5): 134 (A), 143 (U), 164 (A), 598 (C), and 610 (G) in the 5'UTR; and 3481 (A), 3847 (A), 4115 (U), 4423 (A), 4558 (A), 5431 (G), 6205 (A), 6843 (G), and 7097 (U) in the non-structural proteins (the nucleotide in the parental MEF-1 strain is indicated between brackets after its position and, thus, this is mutated into a different nucleotide in this embodiment). In certain particular embodiments thereof, the genome of the recombinant attenuated poliovirus strain comprises at least 10, 11, 12, 13 or 14 of the following mutations as compared to the genome of a MEF-1 strain (SEQ ID NO:5): 134 (A to G), 143 (U to C), 164 (A to G), 598 (C to U), and 610 (G to A) in the 5'UTR; and 3481 (A to A), 3847 (A to U), 4115 (U to C), 4423 (A to G), 4558 (A to U), 5431 (G to A), 6205 (A to G), 6843 (G to A), and 7097 (U to C) in the non-structural proteins. In certain embodiments, the capsid of such strains can be replaced with a capsid from a Mahoney, or from a Saukett strain.

In further non-limiting examples in certain embodiments, this disclosure provides a recombinant attenuated poliovirus strain that can be propagated in cell culture at 30° C. and that cannot be substantially propagated in cell culture at 37° C., wherein the genome of the recombinant attenuated poliovirus strain comprises mutations at at least 10, 11, 12, 13 or 14 of the following positions as compared to the genome of a Mahoney strain (SEQ ID NO:6): 131 (A), 140 (U), 161 (A), 593 (C), and 605 (G) in the 5'UTR; and 3482 (G), 3848 (A), 4116 (U), 4424 (A), 4559 (A), 5432 (G), 6206 (A), 6844 (G), and 7098 (U) in the non-structural proteins (the nucleotide in the parental Mahoney strain is indicated between brackets after its position and, thus, this is mutated into a different nucleotide in this embodiment). In certain particular embodiments thereof, the genome of the recombinant attenuated poliovirus strain comprises at least 10, 11, 12, 13 or 14 of the following mutations as compared to the genome of a Mahoney strain (SEQ ID NO:6): 131 (A to G), 140 (U to C), 161 (A to G), 593 (C to U), and 605 (G to A) in the 5'UTR; and 3482 (G to A), 3848 (A to U), 4116 (U to C), 4424 (A to G), 4559 (A to U), 5432 (G to A), 6206 (A to G), 6844 (G to A), and 7098 (U to C) in the non-structural proteins. In certain embodiments, the capsid of such strains can be replaced with a capsid from a MEF-1, or from a Saukett strain.

In yet further non-limiting embodiments, the disclosure provides a recombinant attenuated poliovirus strain that can be propagated in cell culture at 30° C. and that cannot be substantially propagated in cell culture at 37° C., wherein the genome of the recombinant attenuated poliovirus strain comprises mutations at at least 10, 11, 12, 13 or 14 of the following positions as compared to the genome of a Saukett strain (SEQ ID NO:7): 133 (A), 142 (U), 163 (A), 596 (C), and 608 (G) in the 5'UTR; and 3472 (A), 3839 (A), 4107 (U), 4415 (A), 4550 (A), 5423 (G), 6197 (A), 6835 (G), and 7089 (U) in the non-structural proteins (the nucleotide in a parental Saukett strain is indicated between brackets after its position and, thus, this is mutated into a different nucleotide in this embodiment). In certain particular embodiments thereof, the genome of the recombinant attenuated poliovirus strain comprises at least 10, 11, 12, 13 or 14 of the following mutations as compared to the genome of a Saukett strain (SEQ ID NO:7): 133 (A to G), 142 (U to C), 163 (A to G), 596 (C to U), and 608 (G to A) in the 5'UTR; and 3472 (A to A), 3839 (A to U), 4107 (U to C), 4415 (A to G), 4550 (A to U), 5423 (G to A), 6197 (A to G), 6835 (G to A), and 7089 (U to C) in the non-structural proteins. In certain embodiments, the capsid of such strains can be replaced with a capsid from a MEF-1, or from a Mahoney strain.

In yet further non-limiting embodiments, the disclosure provides a recombinant attenuated poliovirus strain that can be propagated in cell culture at 30° C. and that cannot be substantially propagated in cell culture at 37° C., wherein the genome of the recombinant attenuated poliovirus strain comprises mutations at at least 10, 11, 12, 13 or 14 of the following positions as compared to the genome of a Sabin 3 strain (SEQ ID NO:8): 133 (A), 142 (U), 163 (G), 596 (C), and 608 (G) in the 5'UTR; and 3473 (A), 3839 (A), 4107 (U), 4415 (A), 4550 (A), 5423 (G), 6197 (A), 6835 (G), and 7089 (U) in the non-structural proteins (the nucleotide in a parental Sabin 3 strain is indicated between brackets after its position and, thus, this is mutated into a different nucleotide in this embodiment). In certain particular embodiments thereof, the genome of the recombinant attenuated poliovirus strain comprises at least 10, 11, 12, 13 or 14 of the following mutations as compared to the genome of a Sabin 3 strain (SEQ ID NO:8): 133 (A to G), 142 (U to C), 163 (G to G), 596 (C to U), and 608 (G to A) in the 5'UTR; and 3473 (A to A), 3839 (A to U), 4107 (U to C), 4415 (A to G), 4550 (A to U), 5423 (G to A), 6197 (A to G), 6835 (G to A), and 7089 (U to C) in the non-structural proteins. In certain embodiments, the capsid of such strains can be replaced with a capsid from a Mahoney, MEF-1, or from a Saukett strain.

In further non-limiting examples in certain embodiments, this disclosure provides a recombinant attenuated poliovirus strain that can be propagated in cell culture at 30° C. and that cannot be substantially propagated in cell culture at 37° C., wherein the genome of the recombinant attenuated poliovirus strain comprises mutations at at least 10, 11, 12, 13 or 14 of the following positions as compared to the genome of a Sabin 1 strain (SEQ ID NO:9): 131 (A), 140 (U), 161 (A), 593 (C), and 605 (G) in the 5'UTR; and 3482 (G), 3848 (A), 4116 (C), 4424 (A), 4559 (A), 5432 (G), 6206 (A), 6844 (G), and 7098 (U) in the non-structural proteins (the nucleotide in the parental Sabin 1 strain is indicated between brackets after its position, and thus this is mutated into a different nucleotide in this embodiment). In certain particular embodiments thereof, the genome of the recombinant attenuated poliovirus strain comprises at least 10, 11, 12, 13 or 14 of the following mutations as compared to the genome of a Sabin 1 strain (SEQ ID NO:9): 131 (A to G), 140 (U to C), 161 (A to G), 593 (C to U), and 605 (G to A) in the 5'UTR; and 3482 (G to A), 3848 (A to U), 4116 (C to C), 4424 (A to G), 4559 (A to U), 5432 (G to A), 6206 (A to G), 6844 (G to A), and 7098 (U to C) in the non-structural proteins. In certain embodiments, the capsid of such strains can be replaced with a capsid from a Mahoney, MEF-1, or from a Saukett strain.

In further non-limiting examples in certain embodiments, this disclosure provides a recombinant attenuated poliovirus strain that can be propagated in cell culture at 30° C. and that cannot be substantially propagated in cell culture at 37° C., wherein the genome of the recombinant attenuated poliovirus strain comprises mutations at at least 10, 11, 12, 13 or 14 of the following positions as compared to the genome of a Sabin 2 strain (SEQ ID NO:10): 131 (A), 140 (U), 161 (A), 594 (C), and 606 (G) in the 5'UTR; and 3481 (G), 3847 (A), 4115 (U), 4423 (A), 4558 (A), 5431 (G), 6205 (A), 6844 (G), and 7098 (U) in the non-structural proteins (the nucleotide in the parental Sabin 2 strain is indicated between brackets after its position, and thus this is mutated into a different nucleotide in this embodiment). In certain particular embodiments thereof, the genome of the recombinant attenuated poliovirus strain comprises at least 10, 11, 12, 13 or 14 of the following mutations as compared to the genome of a Sabin 2 strain (SEQ ID NO:10): 131 (A to G), 140 (U to C), 161 (A to G), 594 (C to U), and 606 (G to A) in the 5'UTR; and 3481 (G to A), 3847 (A to U), 4115 (U to C), 4424 (A to G), 4559 (A to U), 5432 (G to A), 6206 (A to G), 6844 (G to A), and 7098 (U to C) in the non-structural proteins. In certain embodiments, the capsid of such strains can be replaced with a capsid from a Mahoney, MEF-1, or from a Saukett strain.

The disclosure also provides a recombinant attenuated poliovirus strain that can be propagated in cell culture at 30° C. and that cannot be substantially propagated in cell culture at 37° C., wherein the genome of the recombinant attenuated poliovirus strain comprises the following nucleotides at at least 10, 11, 12, 13 or 14 of the following positions as compared to the genome of a parent poliovirus strain (wherein the parent poliovirus strain is, for instance, a Brunenders/MEF-1/Mahoney/Saukett/Sabin 3/Sabin 2/Sabin 1 strain, respectively, with respective genome sequences as in, for instance, SEQ ID NOS:1 and 5-10): G at position 133/134/131/133/133/131/131, C at position 142/143/140/142/142/140/140, G at position 163/164/161/163/163/161/161, U at position 597/598/593/596/596/593/594, and A at position 609/610/605/608/608/605/606 in the 5'UTR; and A at position 3486/3481/3482/3473/3473/3482/3481, U at position 3852/3847/3848/3839/3839/3848/3847, C at position 4120/4115/4116/410741407/4116/4115, G at position 4428/4423/4424/4415/4415/4424/4423, U at position 4563/4558/4559/4550/4550/4559/4558, A at position 5436/5431/5432/5423/5423/5423/5431, G at position 6210/6205/6206/6197/5197/6206/6205, A at position 6848/6843/6844/6835/6835/6844/6843, and C at position 7102/7097/7098/7089/7089/7098/7097 in the non-structural proteins, or in corresponding positions in other PV parent strains based on alignment with the sequences for these four strains. In certain embodiments, the capsid of such strains comprises a capsid sequence from a Mahoney, from a MEF-1, or from a Saukett strain.

The disclosure thus also provides further methods for generating CAVA-PV strains, by introducing mutations (e.g., via routine genetic engineering, or via de novo synthesis of complete poliovirus genomes) in a wild-type poliovirus genome (e.g., from Brunenders, Mahoney, MEF-1, Saukett, or other PV strains), such that the genome comprises at least 10, 11, 12, 13 or 14 of the following nucleotides at the following positions: G at position 133, C at position 142, G at position 163, U at position 597, and A at position 609 in the 5'UTR; and A at position 3486, U at position 3852, C at position 4120, G at position 4428, U at position 4563, A at position 5436, G at position 6210, A at position 6848, and C at position 7102 in the non-structural proteins with reference to a Brunenders strain (SEQ ID NO:1), or corresponding positions in other PV strains, for instance, as provided in Table 4.

The recombinant attenuated CAVA-PV strains of the disclosure typically are also genetically stable under envisioned production conditions and due to their inability to replicate at physiological conditions of 37° C., they are highly unlikely to revert to a neurovirulent form upon accidental infection and/or escape from a manufacturing facility. Serial passage of CAVA-PV strains at 37° C. always leads to inability to quantify virus after the first passage, indicating inability to revert at this temperature, even after more than ten blind passages, to regain ability for replication at 37° C. This gives CAVA-PV an advantage over other attenuated strains that are capable of replication at physiological temperature. Thus, CAVA-PV provides for development of IPV vaccines with safer vaccine manufacturing procedures with potentially lower bio-containment thresholds because of the mitigated risk of potential disease outbreaks in the case of industrial accidents. In this way, the inherent safety of CAVA-PV as the basis of IPV may help to control costs of IPV manufacture, as well as may allow manufacturing in countries where manufacturing with wild-type PV is restricted or poses a high risk. In addition, the CAVA-PV strains can be grown in suspension cultures of PER.C6® cells at high densities, which provides high yields and, therefore, the use of this production cell line can also contribute to significantly lower costs of IPV production compared to other cell lines. See, for example, U.S. Pat. No. 8,546,123 and Sanders, Edo-Matas et al. (2012).

CAVA-PV strains can be propagated by methods that are well known by those skilled in the art. For example, CAVA-PV can be propagated by culturing in a permissive cell line (e.g., PER.C6®, or Vero cells, HEK293 cells, HeLa, L20B, etc.), and at permissive temperatures (e.g., 20-33° C., 26-33° C., 28-32° C., or preferably at about 30° C.). Suitable culture media for such cell lines are widely known and available from various manufacturers. Preferably, serum-free culture media are used and, in certain embodiments, cells are cultured in suspension. Harvesting of the virus is typically performed when the maximum titer is reached; this is dependent on the MOI used and the incubation temperature. In general, an MOI of 1 will reach the maximum titer between 12-48 hours post-infection (hpi), e.g., 18-30 hpi, e.g., around 24 hpi at 30° C.

Methods for harvesting and purifying poliovirus or viral components, and production of vaccines therefrom are used in the art for decades, and thus are well known and have been amply described (see, for example, WO 2007/007344; U.S. Pat. No. 4,525,349; and van Wezel, van Steenis et al. 1978; Montagnon, Fanget et al. 1984, all incorporated by reference herein).

In general, each of the poliovirus strains is cultured in a separate process and, if, for instance, a trivalent vaccine containing three types of poliovirus is prepared, the (inactivated, for IPV) viruses are mixed and formulated for preparation of individual dosages. In certain embodiments, for example, a final vaccine per dose may, for instance, comprise different amounts of each CAVA-PV. In certain embodiments, this can be done with CAVA type 1 (CAVA-$PV_{Mahoney}$), type 2 (CAVA-$PV_{MEF\text{-}1}$) and type 3 (CAVA-$PV_{Saukett}$) strains. In certain embodiments, a final vaccine per dose (e.g., 0.5 ml) may, for instance, comprise 10-80, e.g., 40, D-antigen units (DU) of type 1, 2-20, e.g., 8, DU of type 2, and 8-64, e.g., 32, DU of type 3, as determined by comparison to reference preparations.

Inactivation of CAVA-PV can be done according to methods that are well known to those skilled in the art, for instance, with formalin or with β-propiolactone (BPL) (see, for example, Jiang, Pye et al. 1986). In certain embodiments, inactivation is performed with formalin, for example, by the following method: the purified viral suspension is filtered over a 0.22 μm membrane, heating to 37° C. with steady magnetic stirring for 24 hours, after which a formalin solution is added to achieve a concentration of 1 per 4,000. While keeping the viral suspension at 37° C., the magnetic stirring is continued for the first four days. On the sixth day, the viral suspension is filtered over a 0.22 micron membrane, and inactivation is continued under suspension at 37° C. until the twelfth day. The inactivated viral suspension is homogenized and may be stored, e.g., at 4° C. After this step, concentrated and/or final batches for administration may be prepared, for instance, by mixing the desired preparations.

In certain embodiments, the purified CAVA-PV or viral component is formulated into a pharmaceutical composition. This can be done according to a variety of methods and using a variety of buffers, all according to routine methods well known to the person skilled in the art after reviewing the instant disclosure. In general, it entails bringing the poliovirus particles in a pharmaceutically acceptable composition, comprising the poliovirus and at least a pharmaceutically acceptable excipient. Such a composition may be prepared under conditions known to the skilled person and, in certain embodiments, is suitable for administration to humans. In certain embodiments, the composition may comprise buffered culture medium, which may optionally be Medium M-199, which is used as formulation buffer for certain registered conventional IPVs. Further, phosphate-buffered saline may be used, and the final dosage formulations may comprise, for instance, 0.5% of 2-phenoxyethanol and a maximum of 0.02% of formaldehyde per dose as antimicrobial preservatives.

Pharmaceutically acceptable carriers or excipients and diluents are well known in the art and used extensively in a wide range of therapeutic products. Preferably, carriers are applied that work well in vaccines. In certain embodiments, the vaccines further comprise an adjuvant, e.g., alum. Adjuvants are known in the art to further increase the immune response to an applied antigenic determinant.

For administering to humans, the disclosure may employ pharmaceutical compositions comprising the CAVA-PV and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well known in the art.

The purified inactivated CAVA-PV or immunogenic parts thereof are preferably formulated and administered as a sterile solution. Sterile solutions may be prepared by, e.g., sterile filtration or by other methods known in the art. The solutions are then lyophilized or filled into pharmaceutical dosage containers. The pH of the solution generally is in the range of pH 3.0 to 9.5, e.g., pH 5.0 to 7.5. The poliovirus or immunogenic parts thereof typically are in a solution having a suitable pharmaceutically acceptable buffer, and the solution of poliovirus may also contain a salt. Optionally, stabilizing agent may be present, such as albumin. In certain embodiments, detergent is added. In certain embodiments, the vaccine may be formulated into an injectable preparation. These formulations contain effective amounts of poliovirus or immunogenic parts thereof, are either sterile liquid solutions, liquid suspensions or lyophilized versions and optionally contain stabilizers or excipients.

The CAVA-PV vaccine obtainable according to this disclosure can be monovalent, containing one type of poliovirus (type 1, 2 or 3), or bivalent (containing two types of poliovirus, e.g., types 1 and 2, 1 and 3, or 2 and 3), or trivalent (containing three types of poliovirus, e.g., types 1, 2 and 3).

Furthermore, in addition to being used as a stand-alone IPV, the CAVA-PV-based IPV obtainable according to methods of this disclosure can be combined with other vaccines in the regular manner, e.g., in the form of a combined vaccine that can optionally include further vaccine components, e.g., against one or more of diphtheria, tetanus, pertussis, Haemophilus influenzae type b (Hib), Hepatitis B virus (HBV), etc., like is commonly done for conventional IPV (see, e.g., "Vaccines," 5th edition, S. Plotkin, W. Orenstein, P. Offit, 2008, Section 2, for various components and combination vaccines; e.g., Chapter 25 describes IPV vaccines (Plotkin, pp. 605-630). Thus, the CAVA-PV vaccine obtainable according to this disclosure is suitable for use in the expanded program on immunization (EPI), and can be combined with the vaccines in that program. Similarly to conventional IPV, the CAVA-PV vaccine according to the disclosure can be given as a single dose, or preferably in prime-boost regimens wherein multiple doses of vaccine are administered with appropriate time intervals. For example, as recommended by the WHO for countries with high immunization coverage (>90%), the schedule could include a primary series of three doses, beginning at 2 months of age (e.g., at 2, 3 and 4 months). Additionally, if the primary series begins earlier (e.g., with a 6-, 10- and 14-week schedule), a booster dose could be administered after an interval of at least 6 months, i.e., a four-dose schedule. Furthermore, a CAVA-PV vaccine according to this disclosure could also be used in combination with OPV as has been suggested by WHO for use of conventional IPV. For example, WHO recommends that all countries currently using only OPV add at least one dose of IPV to the schedule. In polio-endemic countries and in countries at high risk for importation and subsequent spread, WHO also recommends an OPV dose at birth (also called "zero dose"), followed by the primary series of three OPV doses and at least one IPV dose. Ultimately, the optimal dosage regime can be determined according to standard medical practice and will generally follow the same schemes as those for the available IPVs.

It will also be apparent to those of skill in the art that the therapeutically effective amount of the CAVA-PV vaccine obtainable according to this disclosure will depend upon the administration schedule, the unit dose of recombinant polioviruses administered, whether the recombinant attenuated polioviruses is administered in combination with other therapeutic agents, and the status and health of the patient.

This disclosure also includes a kit for administering a composition comprising the CAVA-PV vaccine obtainable according to this disclosure and can be a pharmaceutically acceptable carrier. The kit comprises a recombinant attenuated poliovirus as disclosed herein. The kit can optionally further comprise a pharmaceutically acceptable carrier, an applicator, such as a syringe, and an instructional material for the use thereof. The instructions can provide any information that is useful for directing the administration of the recombinant attenuated poliovirus or for propagating the virus.

Various publications, which may include patents, published applications, technical articles and scholarly articles, are cited throughout the specification in parentheses, and full citations of each may be found at the end of the specification. Each of these cited publications is incorporated by reference herein, in its entirety.

Other embodiments, features, and advantages of the disclosure are further illustrated by reference to the following examples.

EXAMPLES

Without further description, it is believed that one of ordinary skill in the art can, using the preceding description and the following illustrative examples, make and utilize this disclosure and practice the claimed methods. The following working examples, therefore, specifically point out certain embodiments of this disclosure, and are not to be construed as limiting in any way the remainder of the disclosure.

Example 1

Method for Cold-Adapted-Viral-Attenuation (CAVA) and Production of a CAVA Poliovirus (CAVA-PV)

For this example, a Brunenders parental strain was serially passaged 34 times in PER.C6® cells at low temperature (≤30° C.) and at low MOI (0.01) in PERMEXCIS® medium (chemically defined serum-free medium, e.g., available from Lonza, cat. #BE02-039Q), supplemented with 4 mM L-Glutamine. The resulting virus population was dissected to identify temperature-sensitive viral clones in the population with impaired growth at physiological temperatures (37° C.) and wild-type growth at low temperature (30° C.). In screening of approximately 1000 clones, three clones (named G12P5, F9P4, and G11P3) were found that showed temperature sensitivity with impaired growth at 37° C. Impaired growth was defined as a 100- to 1000-fold reduction in maximum titer compared to parental virus. The three clones were still capable of replicating at physiological temperature, but to lower titers. Growth kinetics of the three clones at lower temperature (30° C.) were faster compared to the starting parental strain. The temperature-sensitive clones were sequenced and a total of 31 mutations were found across the three different clones. Each clone had 18 nucleotide mutations of which some were shared among the different clones and some were unique per each clone.

To generate a novel recombinant poliovirus strain, referred to here as Cold-Adapted-Viral-Attenuation Poliovirus (CAVA-PV), all 31 mutations identified in the three clones were combined into one genome using the parental Brunenders sequence as the backbone. The parental Brunenders sequence is provided here as SEQ ID NO:1. A CAVA-PV sequence was synthesized and the CAVA-$PV_{Backbone}$ was rescued. In brief, the sequence for the recombinant attenuated poliovirus CAVA-$PV_{Backbone}$ strain was generated synthetically in the form of a cDNA plasmid, wherein the viral genome sequence is directly downstream of a phage T7 promoter, which is necessary for production of viral RNA. For rescue, a cDNA plasmid containing the CAVA-$PV_{Backbone}$ genome sequence was used as a template for in vitro transcription mediated by the T7 polymerase to produce the viral RNA, which was subsequently used for transfection of cells and virus rescue. This rescue procedure is used frequently in the art (see, for example, van der Werf, Bradley et al. 1986). Table 1 shows the 31 mutations that were combined to produce a CAVA-$PV_{Backbone}$. FIG. 1 is a schematic overview of the CAVA method and how a first CAVA-PV was generated.

Example 2

Figure 2:
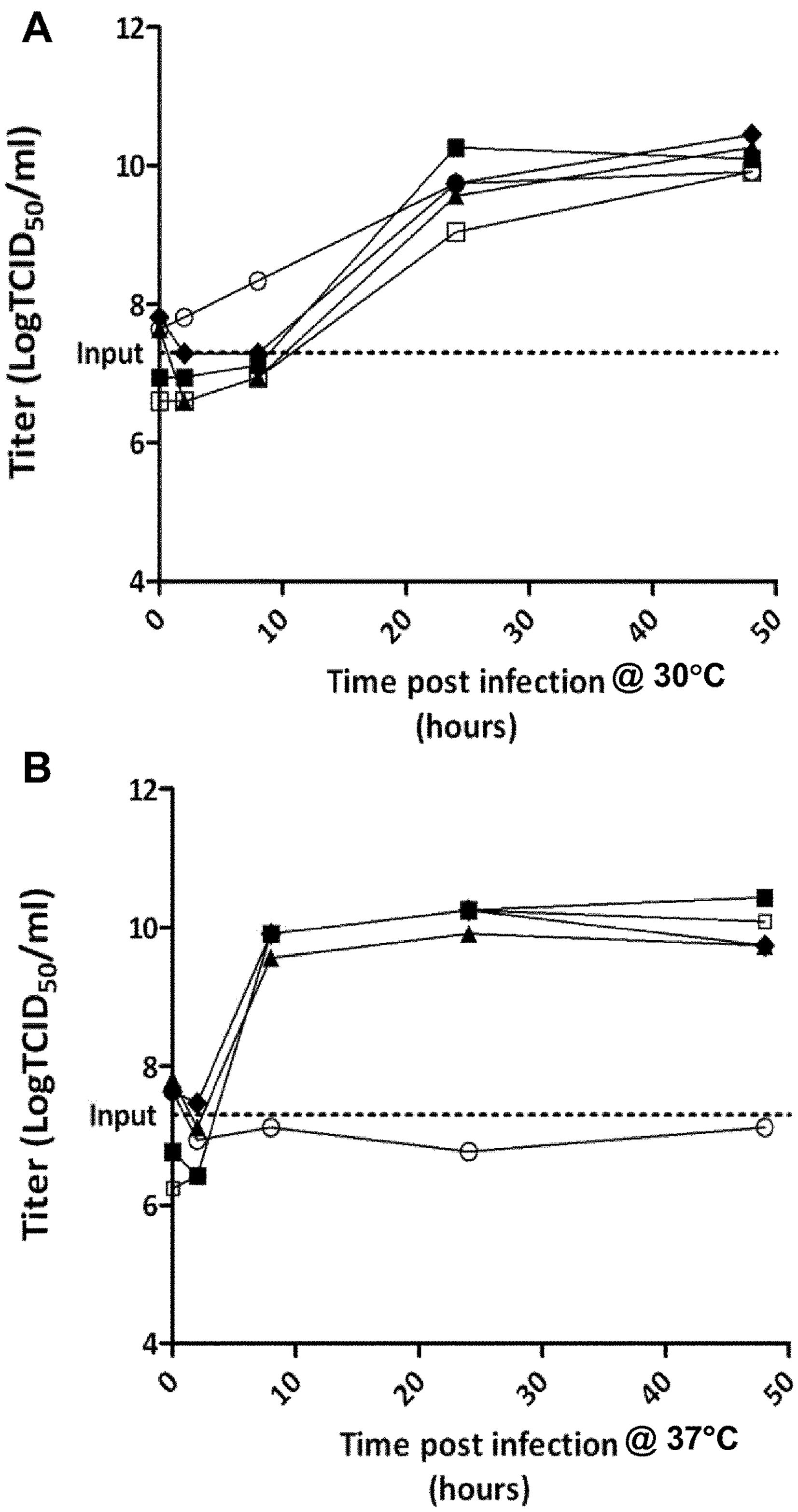
FIG. 2: Replication kinetics in suspension PER.C6® (sPER.C6) cells for a panel of four different Type 1 PV strains and a representative CAVA-$PV_{Backbone}$. Panel A shows growth at 30° C. and Panel B depicts growth at 37° C. Data for the CAVA-PV, Brunhilde, Mahoney, Brunenders, and Sabin 1 strains are shown as open circles, filled diamonds, empty squares, filled triangles, and filled squares, respectively.
Figure 3:
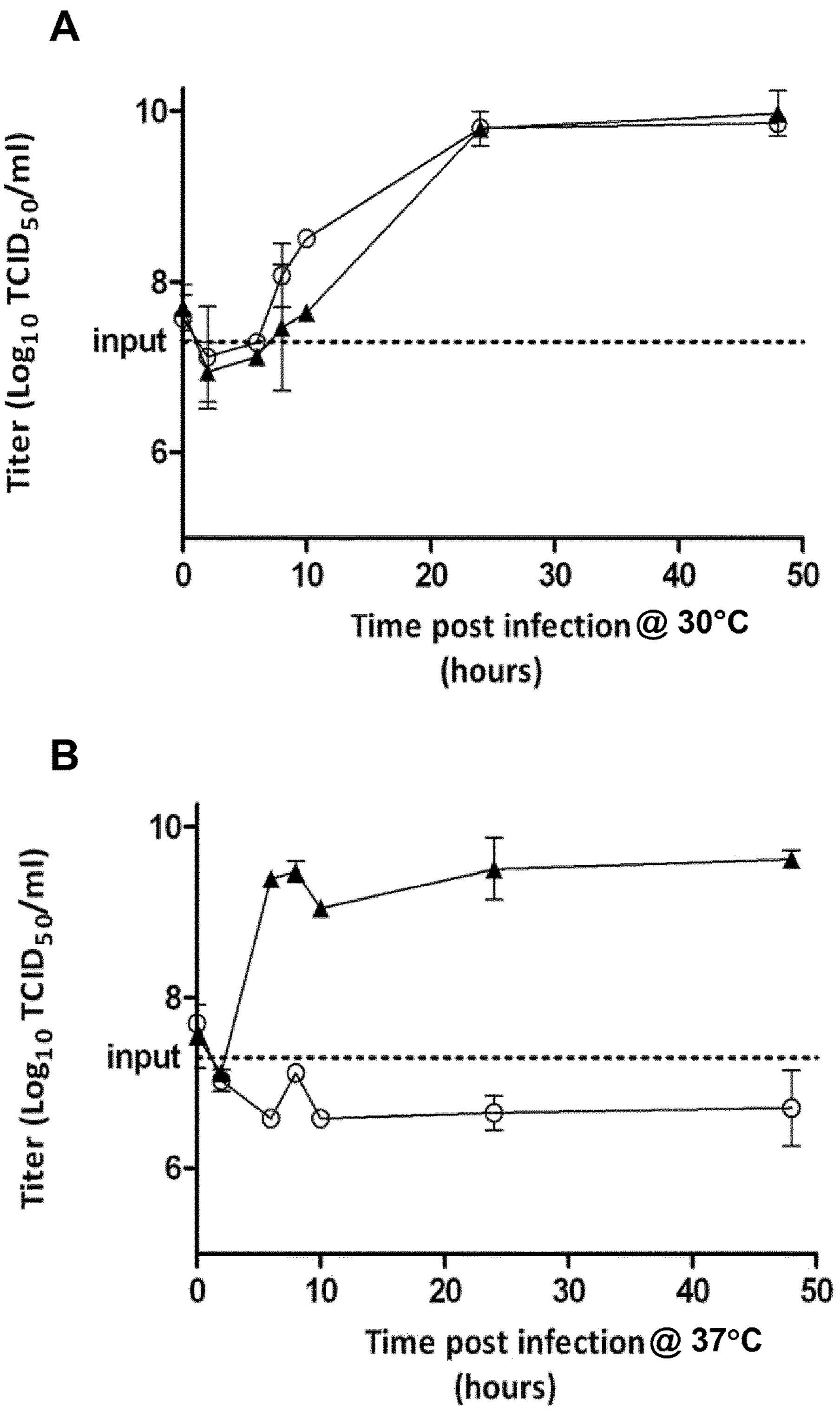
FIG. 3: Average replication kinetics in sPER.C6 cells for Brunenders parental PV and a representative CAVA-$PV_{Backbone}$. The error bars represent standard deviation from the mean (N=3). Panel A shows growth at 30° C. and Panel B shows growth at 37° C. Brunenders parental PV is shown as filled triangles and CAVA-$PV_{Backbone}$ is shown as open circles.
Figure 4A:
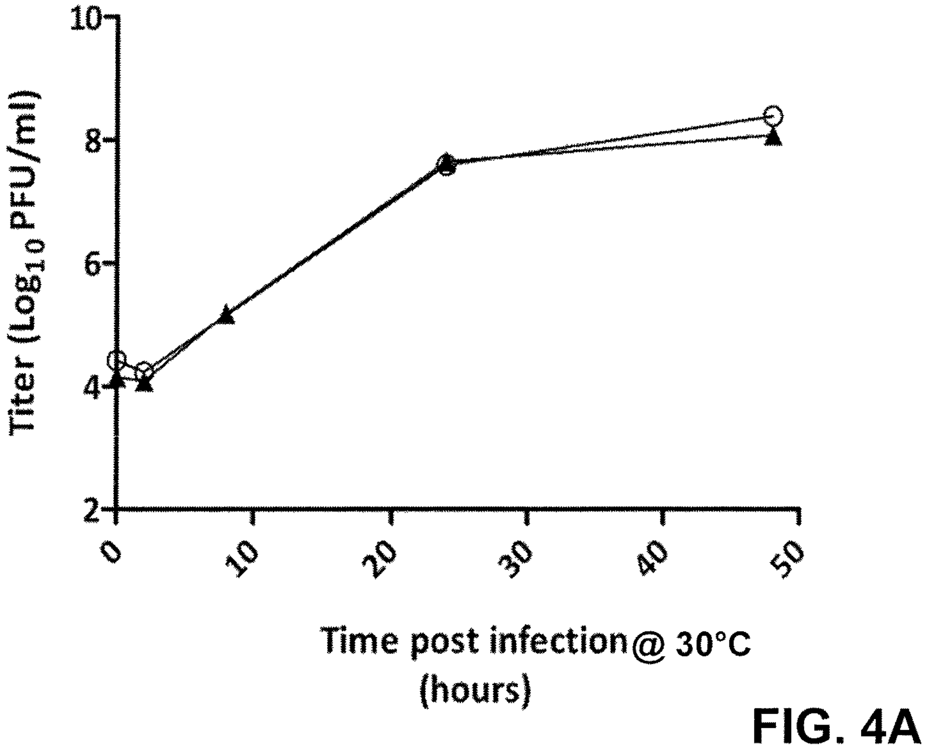
FIGS. 4A-4C: Replication kinetics in HEK293 cells for Brunenders parental PV and a representative CAVA-$PV_{Backbone}$.
Figure 4B:
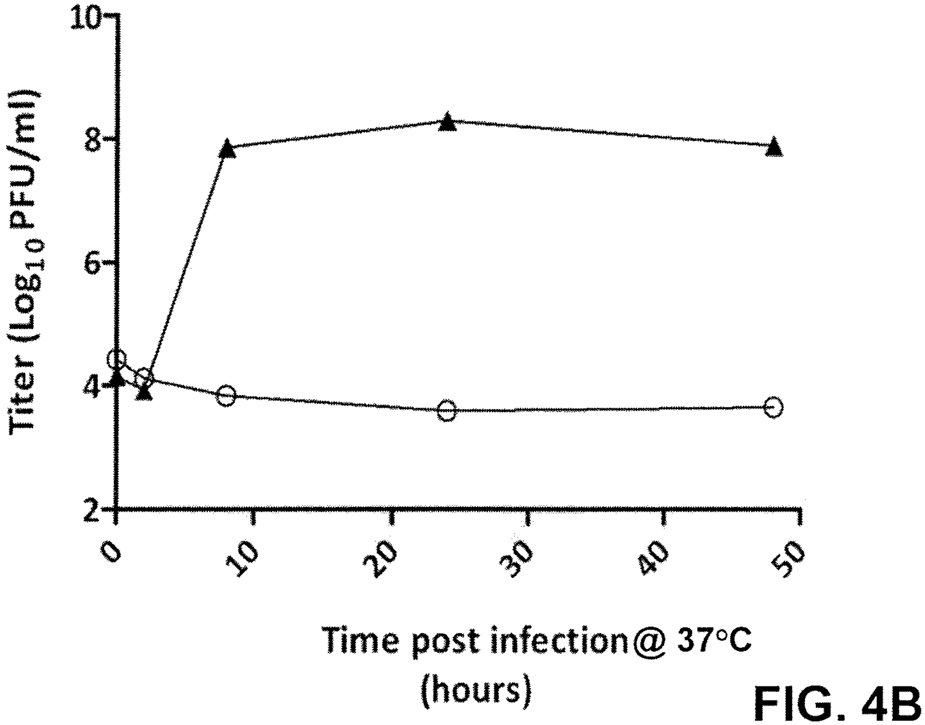
Figure 4C:
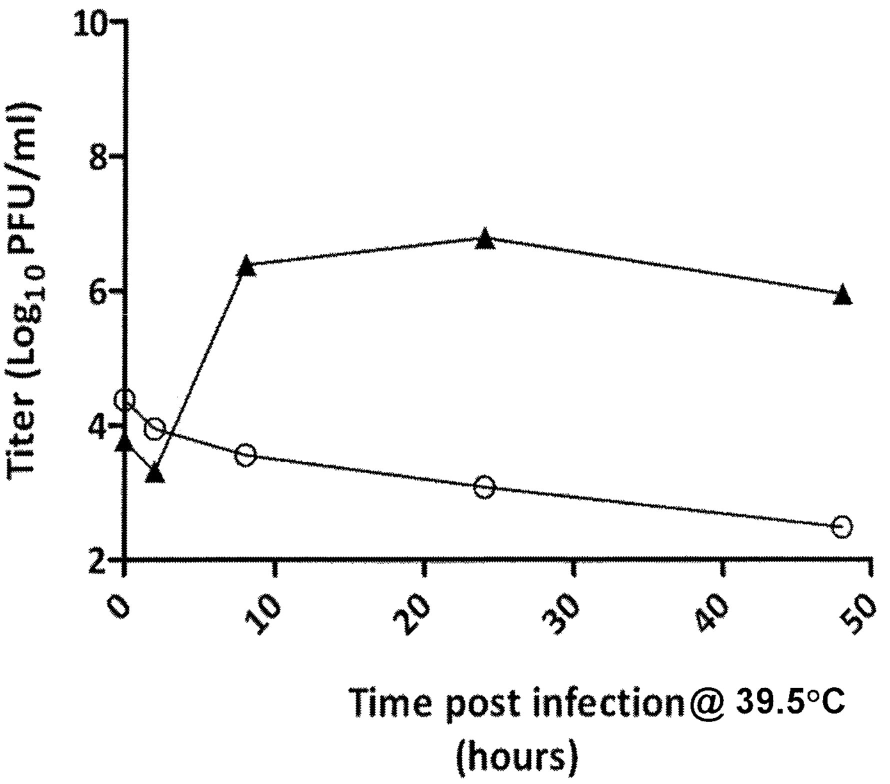
Figure 5A:
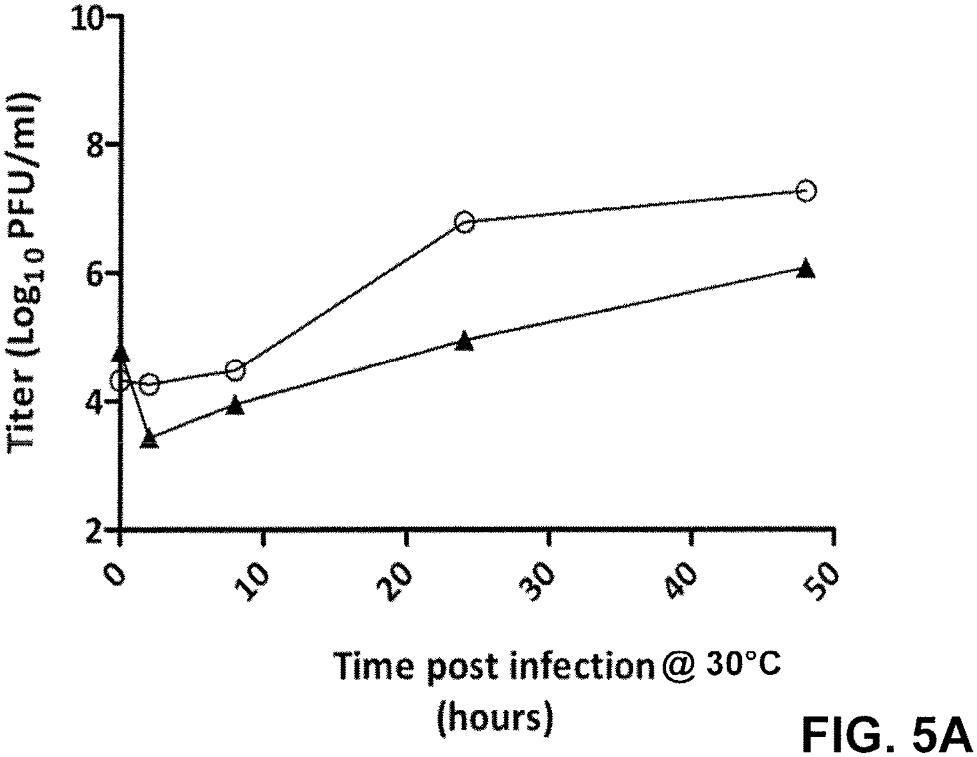
FIGS. 5A-5C: Replication kinetics in L20B cells for Brunenders parental PV and a representative CAVA-$PV_{Backbone}$.
Figure 5B:
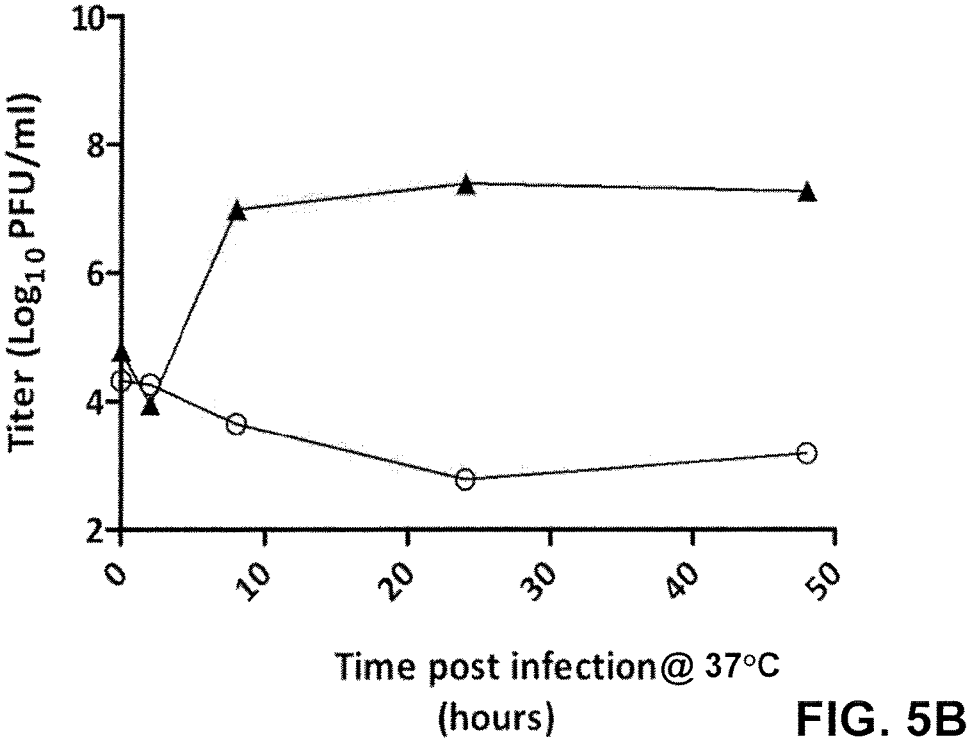
Figure 5C:
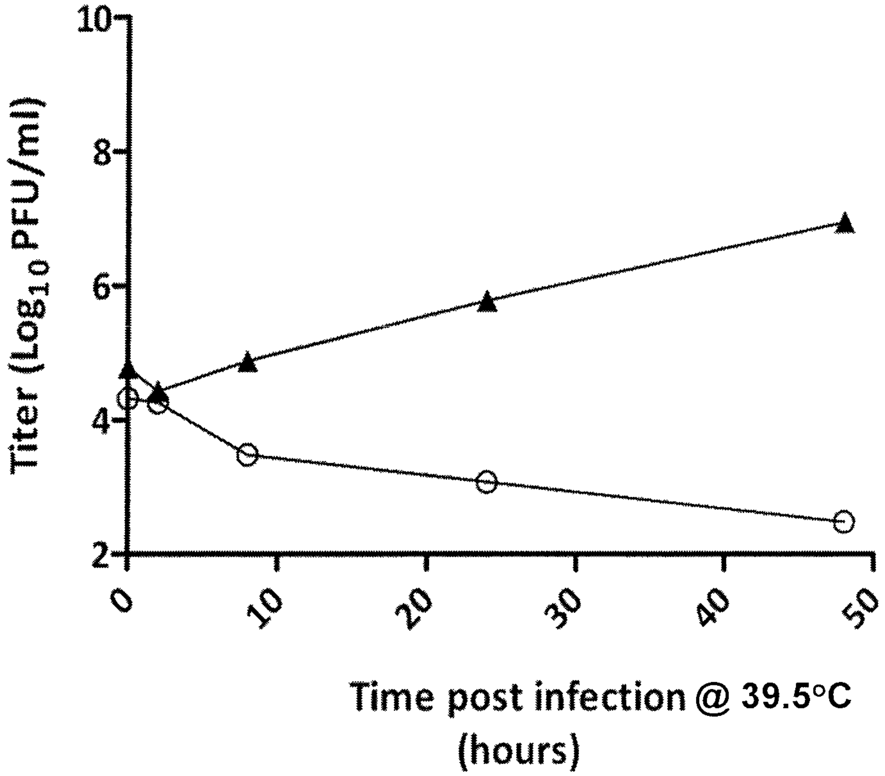
Figure 6A:
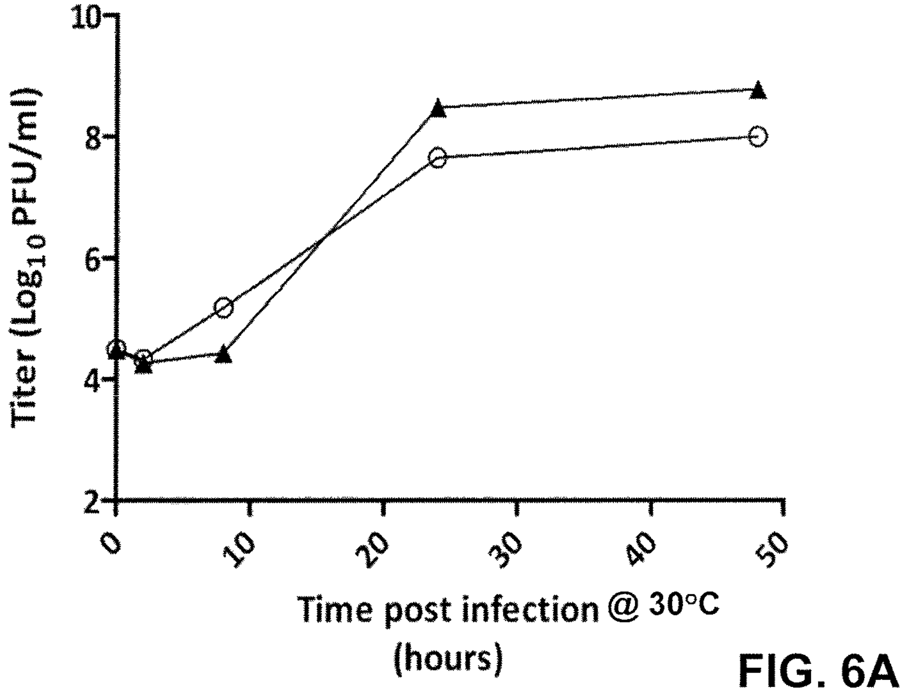
FIGS. 6A-6C: Replication kinetics in HeLa cells for Brunenders parental PV and a representative CAVA-$PV_{Backbone}$.
Figure 6B:
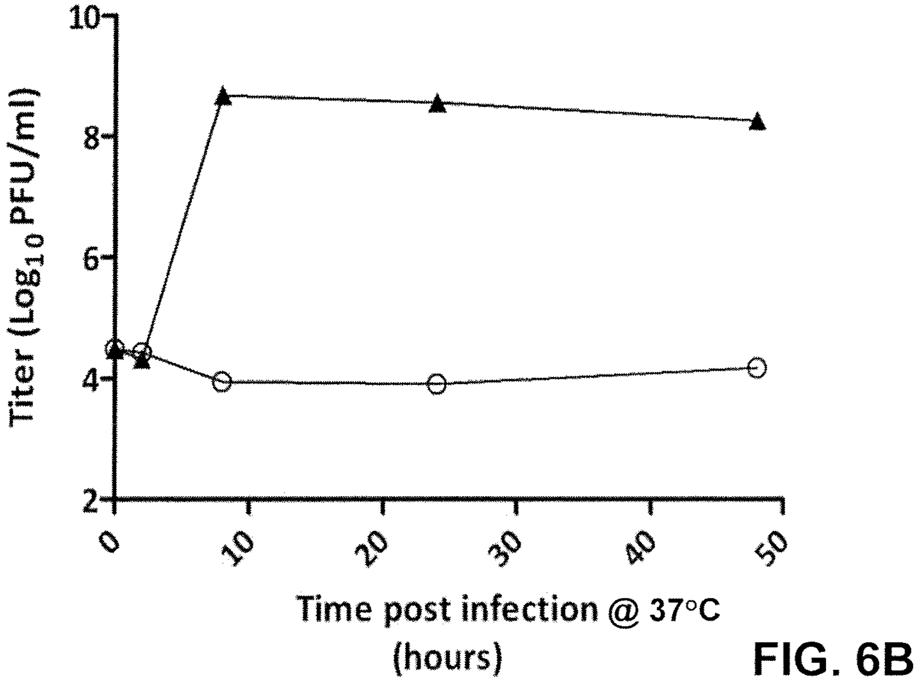
Figure 6C:
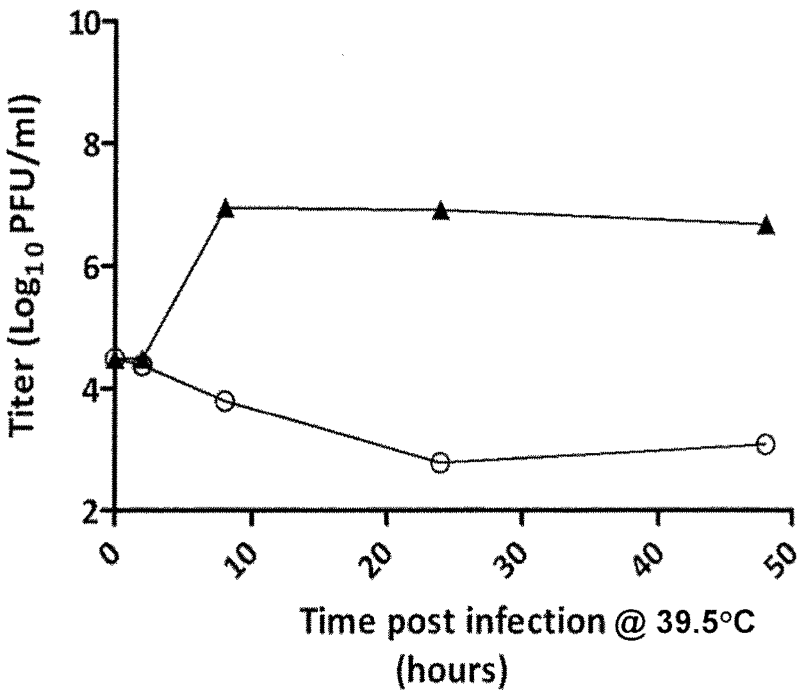

Growth Kinetics of CAVA-$PV_{Backbone}$ in sPER.C6 Cells Compared to Other Type 1 PV Strains Growth kinetics of CAVA-$PV_{Backbone}$ in the suspension PER.C6® (sPER.C6) cells, a production cell line, was compared to the growth of other Type 1 PV (PV1) strains at 30° C. and 37° C. The other PV1 strains were Brunhilde, Brunenders, Mahoney, and Sabin 1. Brunhilde is the parental strain of Brunenders, which is, in turn, the parental strain of CAVA-$PV_{Backbone}$. Mahoney is a wild-type, neurovirulent PV strain, which is typically used as the vaccine strain for the type 1 component of Salk's IPV. Sabin 1 is an attenuated strain used as the vaccine strain for the live attenuated oral poliovirus vaccine (OPV). The suspension PER.C6® cells at time of infection had a cell density of $10\times10^6$ cells/ml in PERMEXCIS® media supplemented with 4 mM L-Glutamine. Cells were infected with an MOI of 2, the infections were performed once (N=1). Viral harvests were titrated using a $TCID_{50}$ assay at 30° C. to give the infectious dose where 50% of the samples showed infection (CPE), which is the Tissue Culture Infectious Dose 50% ($TCID_{50}$) per ml. Line graphs for the replication kinetics in the sPER.C6 cells are shown in FIG. 2. CAVA-$PV_{Backbone}$ showed wild-type growth kinetics, or even faster growth, as compared to the other PV1 strains at 30° C. On the contrary, at 37° C., CAVA-$PV_{Backbone}$ surprisingly showed no significant replication indicating that there was a synergistic accumulative effect from combining the mutations from the three different temperature-sensitive clones. The other PV1 strains all replicated normally and showed similar growth behavior in sPER.C6 cells at 37° C.

The growth kinetics of CAVA-PV and Brunenders in sPER.C6 cells were further evaluated in three independent experiments and the average titer was plotted over time at 30° C. and 37° C. The average titer is plotted in FIG. 3, with error bars representing standard deviation from the mean. The growth curves show similar kinetics for both viruses at 30° C., but at 37° C., CAVA-$PV_{Backbone}$ does not replicate; only the input virus is measured during this assay. The parental Brunenders strain showed no impairment in growth at 37° C. The average maximum titer of CAVA-$PV_{Backbone}$ at 30° C. was 9.82 $Log_{10}$ $TCID_{50}$/ml, which is similar to titers attained with wild-type strains on sPER.C6 cells (Sanders, Edo-Matas et al. 2012).

Example 3

Growth Kinetics of CAVA-$PV_{Backbone}$ in Various Cell Lines in Comparison to Brunenders Starting Virus A successful infection is a complex interplay between virus and host cell, hence, temperature sensitivity may be influenced by host cell factors. Therefore, a panel of various mammalian cell lines was examined for viral growth to confirm the inability of CAVA-$PV_{Backbone}$ to replicate at physiological conditions.

FIGS. 4A-4C, 5A-5C and 6A-6C show the replication kinetics of CAVA-$PV_{Backbone}$, and Brunenders in HEK293, L20B and HeLa cells, respectively. For each cell line, $1\times10^6$ cells were infected at three different temperatures (30° C., 37° C. and 39.5° C.) with an MOI of 2 in DMEM medium+1% BCS. The viral titers were quantified by plaque assay on HelaR19 cells at 30° C., which results in the number of Plaque Forming Units (PFUs) in the viral harvest. The results confirm that CAVA-$PV_{Backbone}$ does not replicate at 37° C. or 39.5° C. in all three cell lines. At 30° C., however, the growth kinetics of CAVA-$PV_{Backbone}$ are similar to parental Brunenders PV strain. The Brunenders virus shows no impairment in replication in any of the cell lines at any of the temperatures, but titers are slightly lower at 39.5° C. compared to the lower temperatures.

Figure 7:
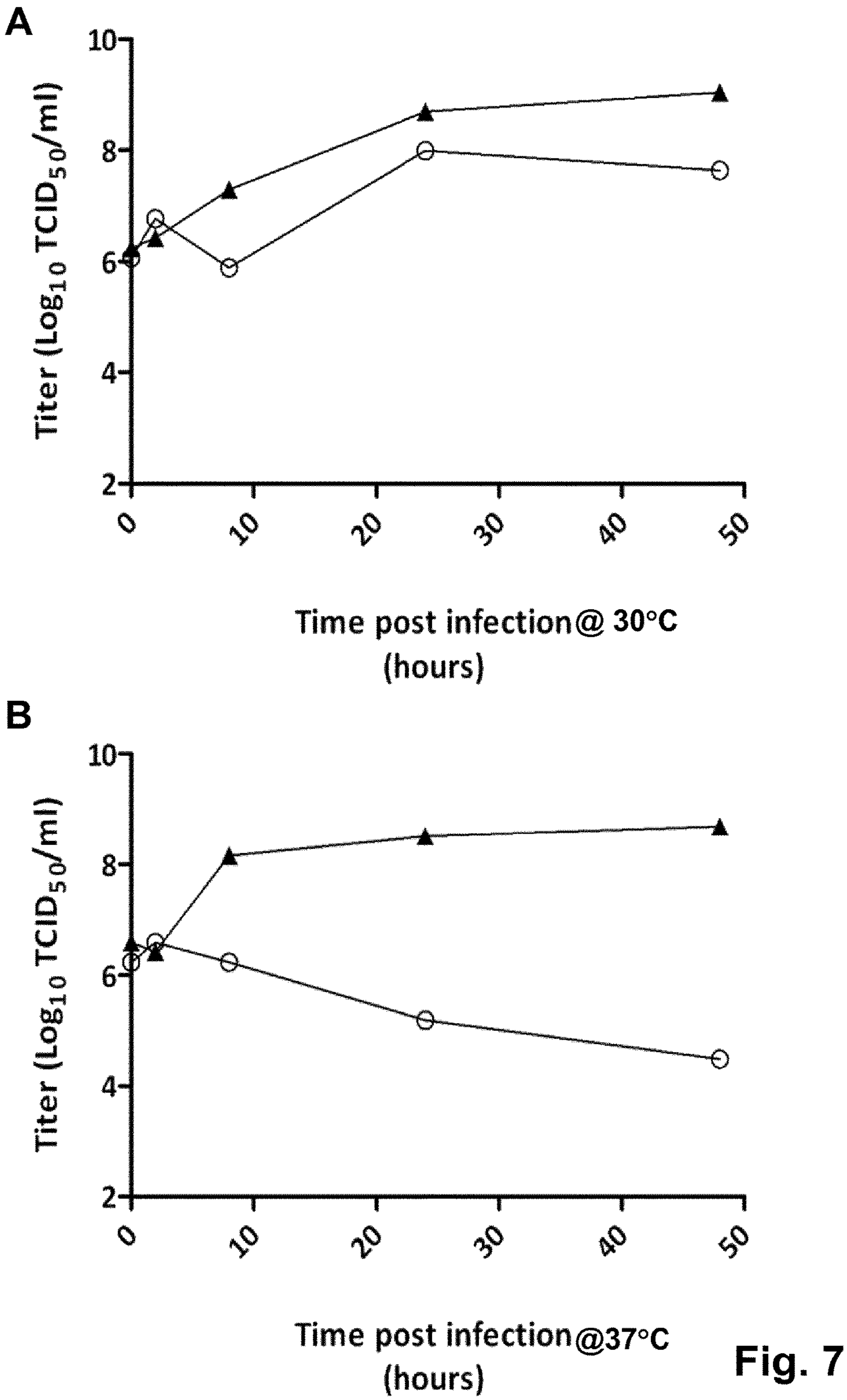
FIG. 7: Replication kinetics in Vero cells for Brunenders parental PV and a representative CAVA-$PV_{Backbone}$. Panel A shows growth at 30° C. and Panel B illustrates growth at 37° C. Brunenders parental PV is shown as filled triangles and CAVA-$PV_{Backbone}$ is shown as open circles.
Figure 8:
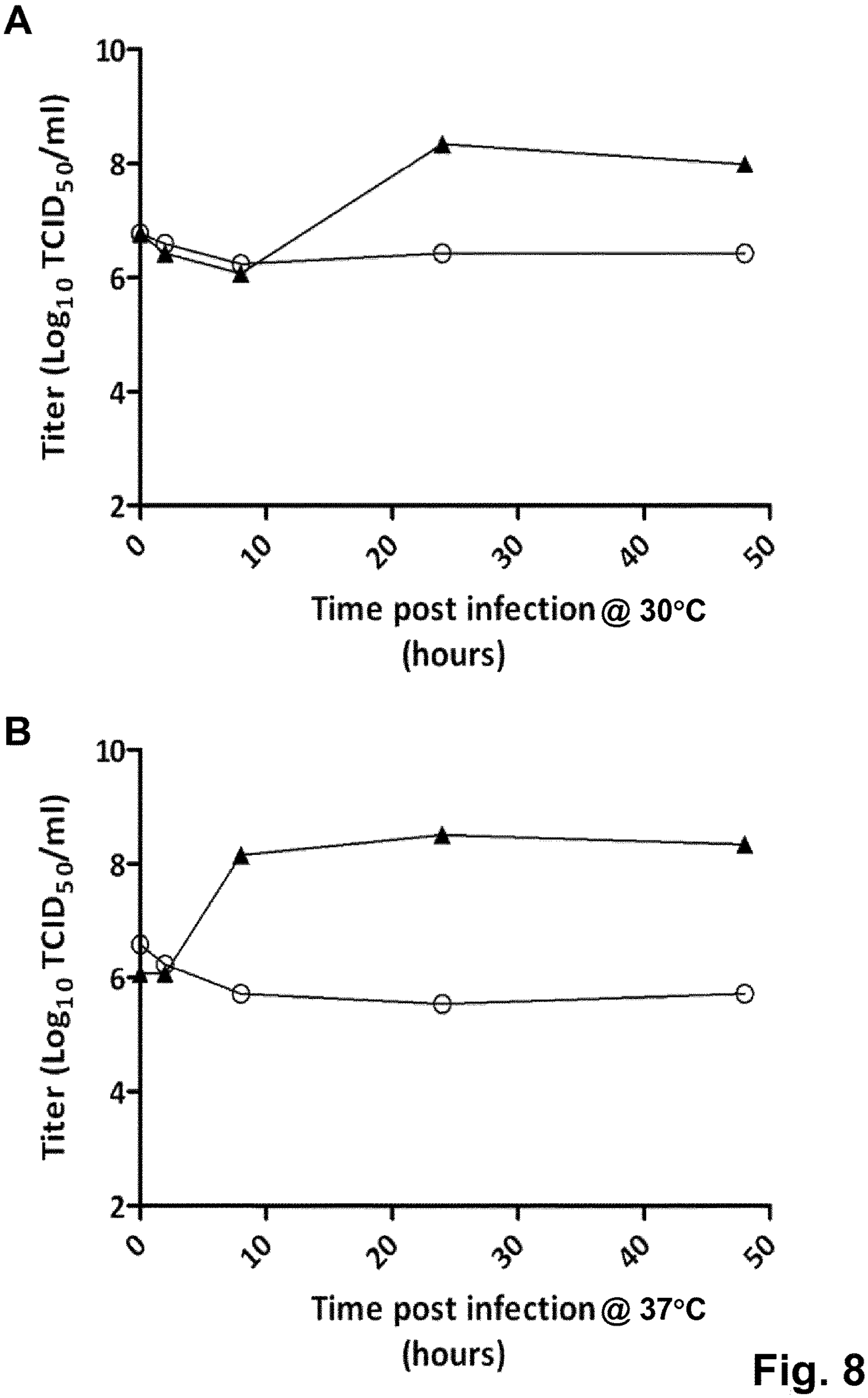
FIG. 8: Replication kinetics in SK-N-MC cells for Brunenders parental PV and a representative CAVA-$PV_{Backbone}$. Panel A depicts growth at 30° C. and Panel B shows growth at 37° C. Brunenders parental PV is shown as filled triangles and CAVA-$PV_{Backbone}$ is shown as open circles.
Figure 9:
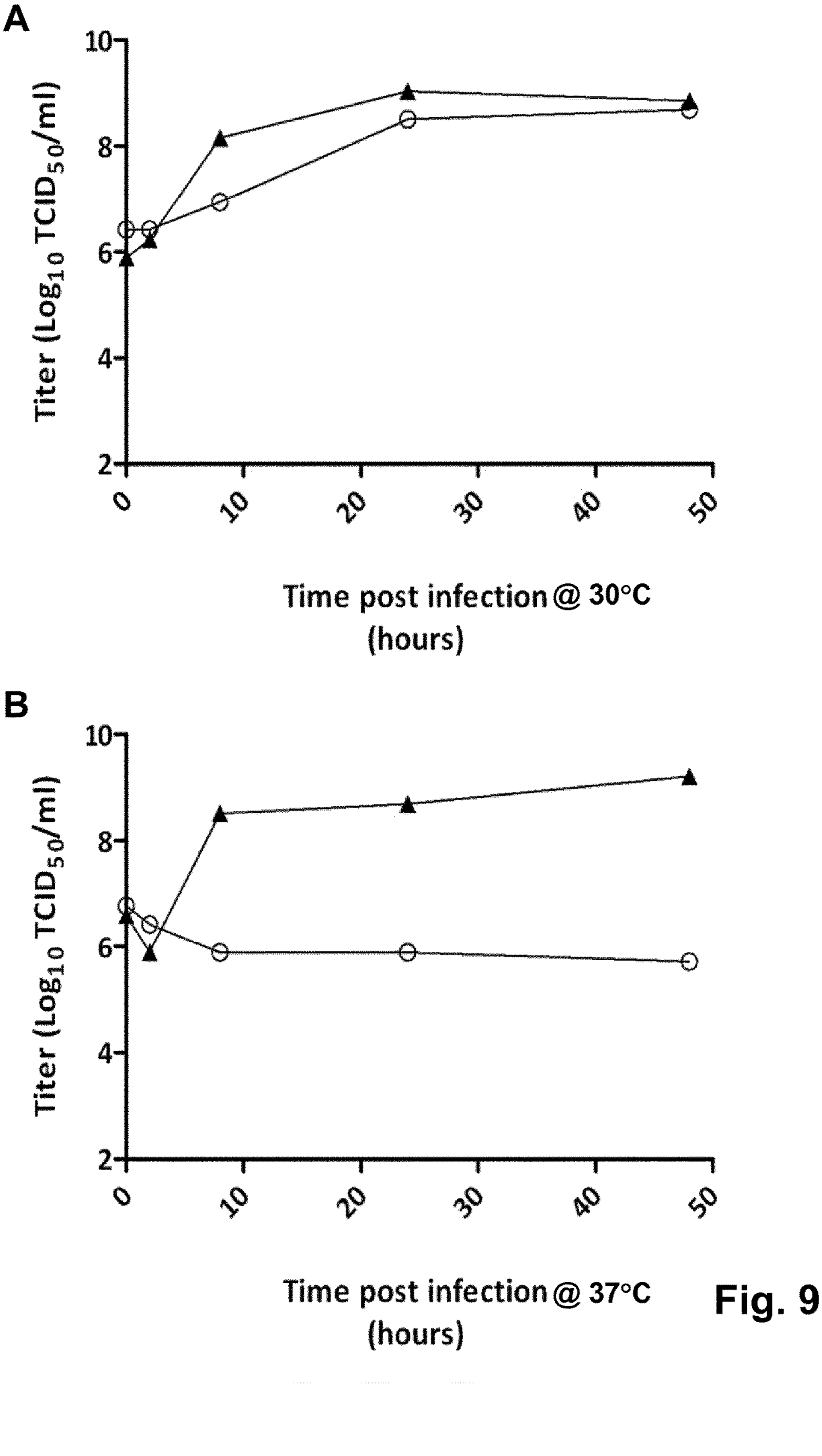
FIG. 9: Replication kinetics in adherent PER.C6® (adPER.C6) cells for Brunenders parental PV and a representative CAVA-$PV_{Backbone}$. Panel A shows growth at 30° C. and Panel B shows growth at 37° C. Brunenders parental PV is shown as filled triangles and CAVA-$PV_{Backbone}$ is shown as open circles.

FIGS. 7, 8 and 9 show the replication kinetics of CAVA-$PV_{Backbone}$ and Brunenders in Vero, SK-N-MC and adherent PER.C6® (adPER.C6) cells, respectively. These infections were performed at either 30° C. or 37° C. at an MOI of 2 in MEM medium +5% FBS (Vero and SK-N-MC cells) or DMEM+10% FBS+4.9 mM $MgCl_2$ (adPER.C6). Viral harvests were titrated using a $TCID_{50}$ assay at 30° C. The results for Vero and adPER.C6 concur with what has been observed previously: CAVA-$PV_{Backbone}$ only shows replication at 30° C., comparable to that of the Brunenders strain. Again, at 37° C., a lack of replication is observed.

For the SK-N-MC cell line (FIG. 8), CAVA-$PV_{Backbone}$ was unable to replicate at both temperatures. This cell line is a human neuronal cell line derived from a neuroepithelioma and has been used as an in vitro model for neurovirulence (Jahan, Wimmer et al. 2011). Although this is not a validated predictive in vitro assay for neuro-attenuation of a virus strain, the inhibited viral growth of CAVA-$PV_{Backbone}$ in this cell line at both 30° C. and 37° C. may indicate an inability to replicate in neuronal cell lines and predict neuro-attenuation.

Example 4

Neurovirulence Testing in CD155 Transgenic Mice

To determine whether the in vitro temperature-sensitive phenotype translates to neuro-attenuation, an in vivo transgenic CD155 mouse model was used (Koike, Taya et al. 1991). CD155 transgenic mice are genetically modified to express the poliovirus receptor (PVR or CD155), which results in susceptibility of the mice to PV infection. The CD155 mice were infected with CAVA-PVs and other selected PV strains. The mice were infected either intracerebrally (i.c.), intramuscularly (i.m.) or intraperitoneally (i.p.) with varying doses to determine the (Paralytic or) Lethal Dose 50 ((P)$LD_{50}$), which corresponds to the number of infectious units (expressed in $TCID_{50}$) needed to cause paralysis or death to 50% of the mice in a given test group. The lower the (P)$LD_{50}$, the more neurovirulent the virus. Table 2 shows the results for the in vivo neurovirulence test. For the CAVA-PVs (active CAVA-$PV_{Backbone}$, CAVA-$PV_{Mahoney}$, CAVA-$PV_{MEF\text{-}1}$ and CAVA-$PV_{Saukett}$) the maximum amount of virus administered to mice did not result in any signs of paralysis in any of the mice injected; therefore, the (P)$LD_{50}$ is given as more than (>) the maximum dose that could be administered. As an indication of neurovirulence, the (P)$LD_{50}$s of other PV viruses were also determined. Brunenders and Brunhilde are the parental strains of CAVA-PV while Mahoney, MEF-1, Saukett and the Sabin viruses are the vaccine strains of IPV and OPV, respectively. Mahoney is the most virulent virus, followed by Brunhilde, Saukett, Brunenders, MEF-1 and the Sabin strains. This concurs with the neurovirulence data in literature of these strains. The CAVA-PVs are less neurovirulent than any of the wild-type strains. CAVA-PVs are at least one million times more attenuated than Mahoney via the intracerebral administration route (the most sensitive route used here, to measure the ability of a virus to destroy neuronal cells and cause paralysis). CAVA-PVs are at least 100 times more attenuated than Brunenders, which is a partially attenuated strain. To ascertain whether the CAVA strains are more attenuated than Sabin, one would need to use a more sensitive model for determination of neurovirulence as this model is not sensitive enough to discriminate between Sabin and CAVA strains. However, the Sabin strains did induce paralysis in some of the mice administered with the highest dose, whereas the CAVA strains did not.

The (P)$LD_{50}$s of two known attenuated viruses (RIPO and Sabin 1) have been reported to be $>10^8$ and $5\times10^7$ PFU, respectively, in the same neurovirulence model (Bouchard, Lam et al. 1995; Jahan, Wimmer et al. 2011). However, these values were not determined in the same experiment, therefore, caution should be exerted when directly comparing these (P)$LD_{50}$s. The RIPO strain is an attenuated oncolytic poliovirus strain licensed for use in clinical trials to treat malignant glioma (Jahan, Wimmer et al. 2011). The CAVA-PV strains perform in a similar fashion as these attenuated strains. In fact, not one mouse infected with the highest possible doses of the CAVA-PV strains showed any signs of disease, while this is not necessarily the case for other attenuated viruses (e.g., Sabin 1, which is the type 1 component of OPV, a licensed live attenuated vaccine, administered to millions of children per year). Thus, in this neurovirulence model, CAVA-PV is shown to be highly attenuated.

Example 5

Genetic Stability of CAVA-PVs Under Production Conditions

Figure 10:
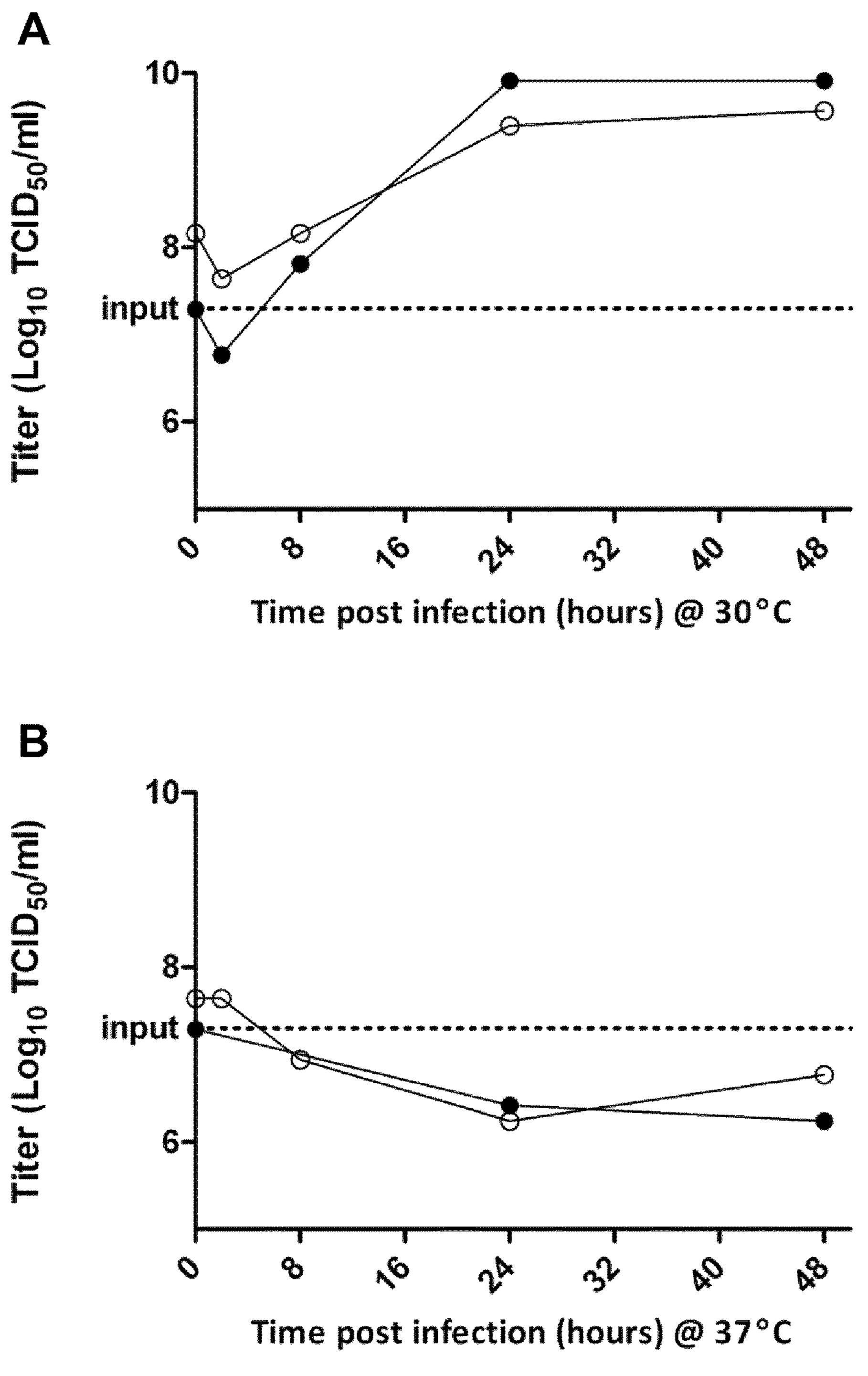
FIG. 10: Replication kinetics for CAVA-$PV_{Backbone}$ (closed circles) and after eight passages (open circles) under envisioned production conditions (Panel A) at 30° C.; and (Panel B) at 37° C., at small scale.

The CAVA-$PV_{Backbone}$ strain was passaged at small scale under envisioned production conditions (sPER.C6 cells with a cell density of $10\times10^6$ vc/ml in PERMEXCIS® medium, at an MOI of 1, at 30° C.) and harvested at 24 hpi. The passaging was done eight times, which represents five passages beyond a theoretical commercial manufacturing batch. After these passages, the entire genome was sequenced. None of the 31 mutations that were introduced to the virus reverted. The entire genome after passaging was identical to the starting stock except for one nucleotide that showed a mixed population at nucleotide 5206 in the 3A gene, causing an amino acid substitution. Due to the large error rate of the RNA polymerase of polioviruses, this mutation was assumed to be random and not inducing any reversion of the temperature-sensitive (and attenuated) phenotype. The temperature-sensitive phenotype was subsequently confirmed by performing replication kinetics and it was observed that the 8× passaged CAVA-PV showed similar growth curves as compared to the CAVA-PV starting stock at both 30° C. and 37° C. (FIG. 10). Thus, the temperature-sensitive phenotype of CAVA-$PV_{Backbone}$, an in vitro indication of neuroattenuation, is stable after multiple passages under production conditions. This would make CAVA-PV suitable for use in the manufacturing process for production of batches for commercial use.

Figure 11:
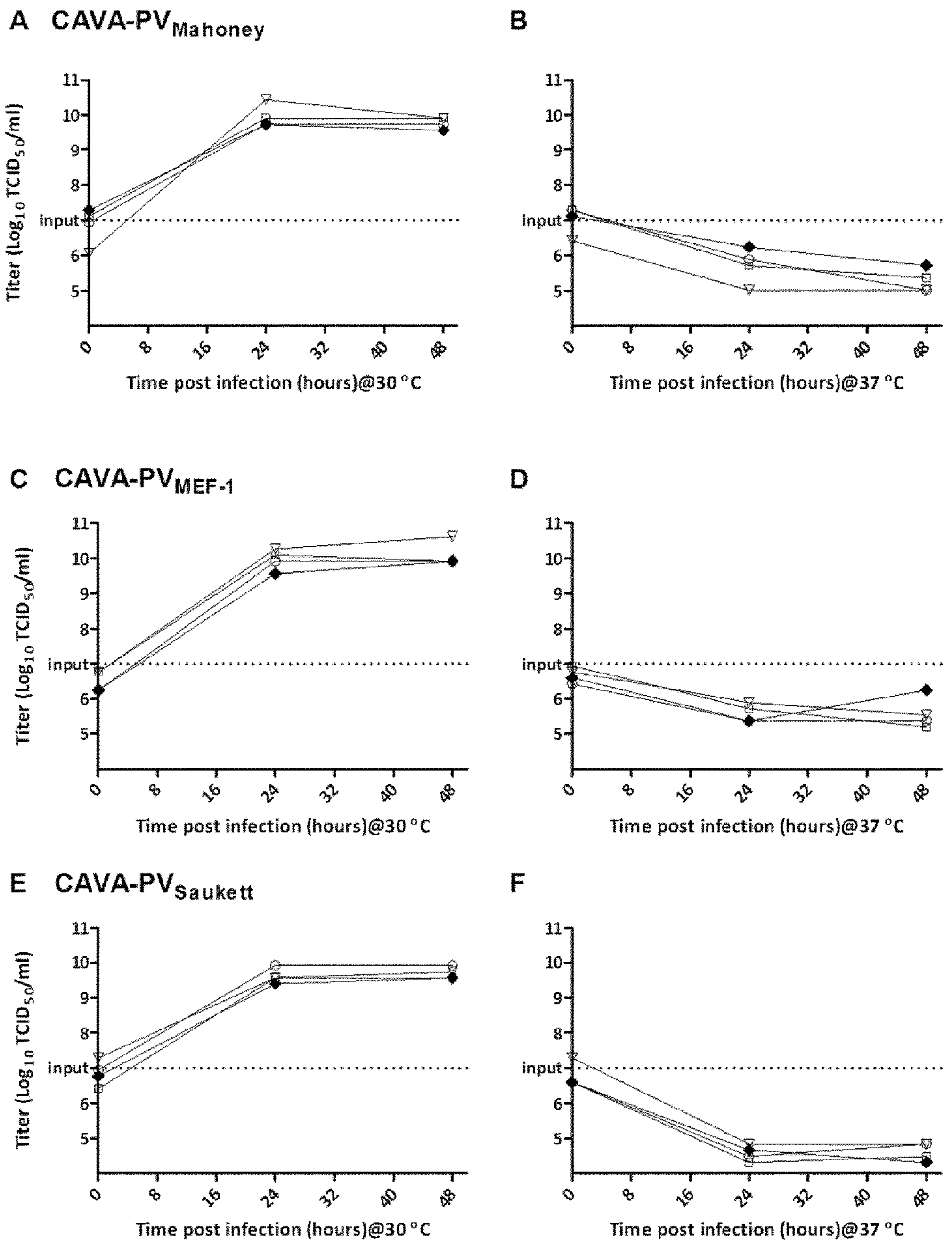
FIG. 11: Replication kinetics of CAVA-$PV_{Mahoney}$ (Panels A and B), CAVA-$PV_{MEF\text{-}1}$(Panels C and D), and CAVA-$PV_{Saukett}$ (Panels E and F), and after five passages on sPER.C6 (N=3) under envisioned production conditions at 30° C. (Panels A, C, and E); and at 37° C. (Panels B, D, and E), at small scale. Filled diamonds represent the growth of the starting stock viruses while empty squares, circles and triangles represent each of the three passaged viruses (N=1, 2 and 3, respectively).

The same genetic stability testing was performed using the envisioned vaccine strains, namely, CAVA-$PV_{Mahoney}$, CAVA-$PV_{MEF\text{-}1}$ and CAVA-$PV_{Saukett}$. Here, viruses were passaged three times (n=3) at small scale under envisioned production conditions (sPER.C6 cells with a cell density of $10\times10^6$ vc/ml in PERMEXCIS® medium, at an MOI of 1, at 30° C. and harvested at 24 hpi). The number of passages was five, which represents two passages beyond a theoretical commercial lot. FIG. 11 depicts the in vitro phenotype of all passaged viruses as compared to the starting stock. All viruses retained their temperature-sensitive phenotype, as well as their in vivo attenuation, where the (P)$LD_{50}$s were still $>10^8$ for the three serotypes after extended passage. Sequencing of the passaged viruses of FIG. 11 showed that only few mutations arose, and as described above, these mutations did not affect the attenuation in vivo and in vitro.

Example 6

Introduction of the Conventional IPV Antigenic Profile into CAVA-PV

Figure 12:
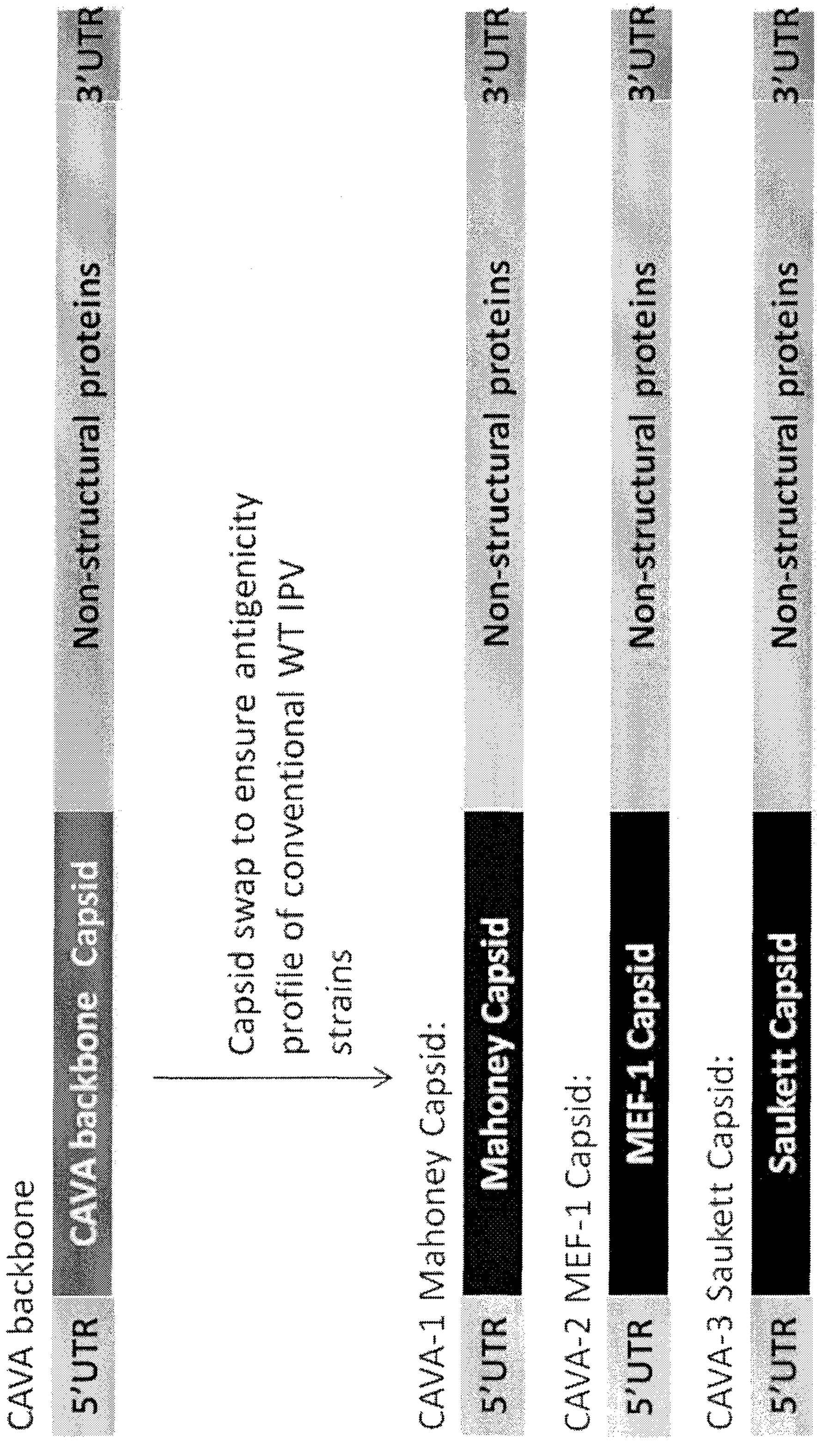
FIG. 12: Schematic overview of the different CAVA-PV vaccine strains after swapping the sequence coding for the capsid of the original CAVA-$PV_{Backbone}$ strain with the sequences coding for the capsids of the Mahoney, MEF-1, and Saukett strains. After the capsid swaps, the resulting vaccine strains are referred to as CAVA-$PV_{Mahoney}$, CAVA-$PV_{MEF\text{-}1}$ and CAVA-$PV_{Saukett}$, respectively.

To generate a CAVA-PV-based IPV that can display the same immune profile as the conventional IPV, the sequences coding for the capsids of some exemplary viruses were placed into the background of the CAVA-PV genome by replacing the sequence coding for the original CAVA-$PV_{Backbone}$ capsid. This capsid swap removes 7 of the 31 mutations deliberately engineered into CAVA-PV. The capsid swaps are first designed in silico and, consequently, DNA is generated by chemical synthesis of the novel genomes. Once the plasmid DNA was synthesized (outsourced to GENSCRIPT®) this was used to generate viral RNA via in vitro transcription and consequently rescue the different novel recombinant CAVA-PVs via transfection. The resulting vaccine strains were named CAVA-$PV_{Mahoney}$, CAVA-$PV_{MEF\text{-}1}$ and CAVA-$PV_{Saukett}$, which contain the Mahoney, MEF-1 and Saukett capsids, respectively. Representative capsid amino acid sequences are provided here for PV type 1 strain Mahoney (SEQ ID NO:2), PV type 2 strain MEF-1 (SEQ ID NO:3), and PV type 3 strain Saukett (SEQ ID NO:4). FIG. 12 shows a schematic overview of these different CAVA-PV vaccine strains.

Example 7

Figure 13:
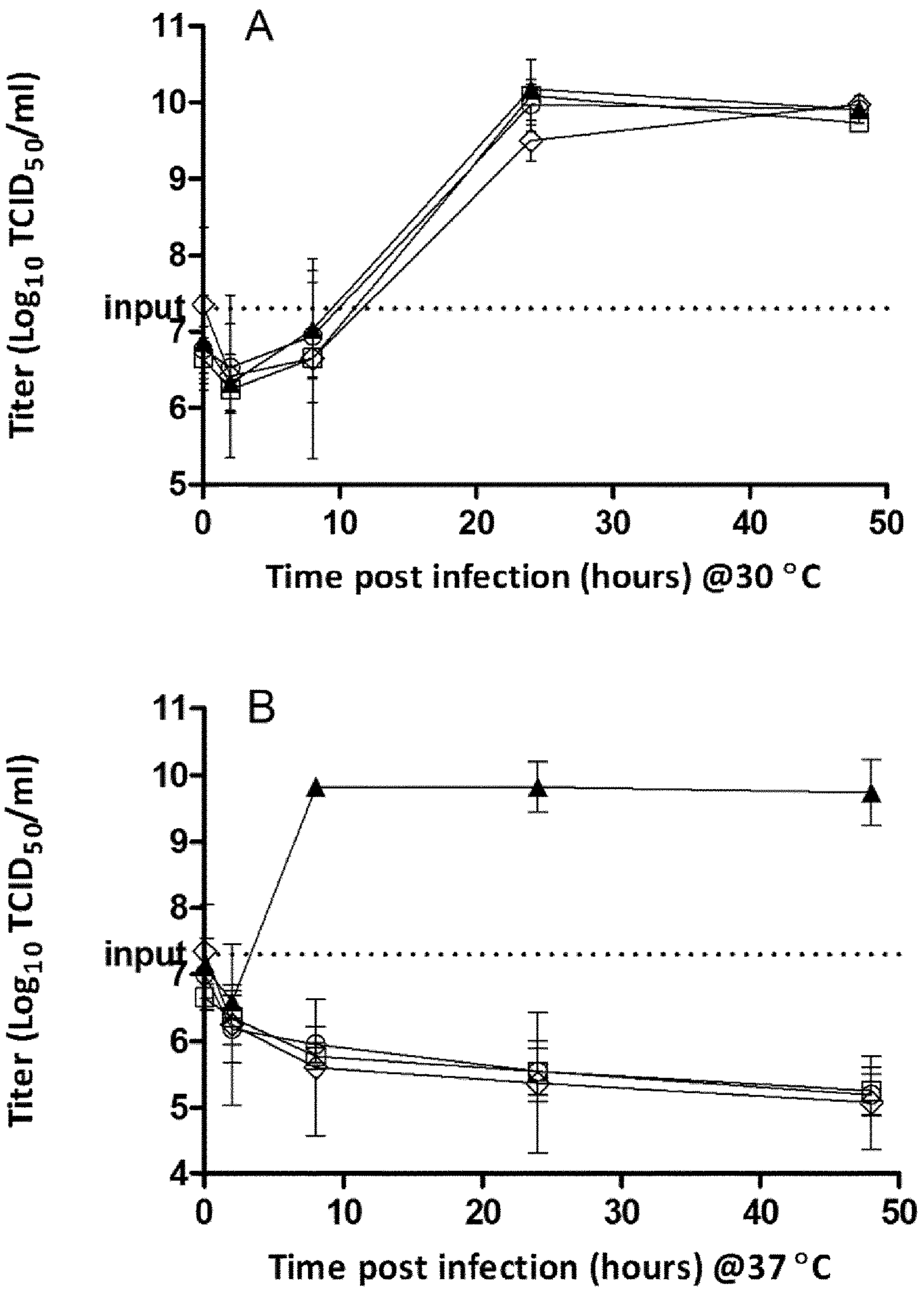
FIG. 13: Replication kinetics of CAVA-$PV_{Mahoney}$, CAVA-$PV_{MEF\text{-}1}$ and CAVA-$PV_{Saukett}$ and the parental Brunenders strain. Panel A shows growth at 30° C. and Panel B shows growth at 37° C. The error bars represent standard deviation from the mean (N=2 or 3). Brunenders parental PV is shown as filled triangles, CAVA-$PV_{Mahoney}$ shown as open circles, CAVA-$PV_{MEF\text{-}1}$ shown as open squares, and CAVA-$PV_{Saukett}$ shown as open diamonds.

Growth Kinetics of CAVA-$PV_{Mahoney}$, CAVA-$PV_{MEF\text{-}1}$ and CAVA-$PV_{Saukett}$ in sPER.C6 Cells Compared to the Parental Brunenders Strain Growth kinetics of CAVA-$PV_{Mahoney}$, CAVA-$PV_{MEF\text{-}1}$ and CAVA-$PV_{Saukett}$ in the suspension PER.C6® (sPER.C6) cells, a production cell line, was compared to the growth of PV1 Brunenders at 30° C. and 37° C. The suspension PER.C6® cells at time of infection had a cell density of $10\times10^6$ cells/ml in PERMEXCIS® media supplemented with 4 mM L-Glutamine. Cells were infected with an MOI of 1, the infections were performed twice for CAVA-$PV_{Saukett}$ and Brunenders (N=2) and three times for CAVA-$PV_{Mahoney}$ and CAVA-$PV_{MEF\text{-}1}$ (N=3). Viral harvests were titrated using a $TCID_{50}$ assay at 30° C. Line graphs for the replication kinetics in the sPER.C6 cells are shown in FIG. 13. The CAVA-PVs showed wild-type growth kinetics as compared to the parental Brunenders strains at 30° C., with error bars representing standard deviation from the mean. On the contrary, at 37° C., the CAVA-PVs showed no substantial replication, as was also observed for the CAVA-$PV_{Backbone}$, indicating that the temperature sensitivity of the viruses lies within the mutations outside of the capsid region. The Brunenders strain replicated normally and showed similar growth behavior in sPER.C6 cells at 37° C.

The average maximum titer of CAVA-$PV_{Mahoney}$, CAVA-$PV_{MEF\text{-}1}$ and CAVA-$PV_{Saukett}$ at 30° C. was 9.94, 9.91 and 9.74 $Log_{10}$ $TCID_{50}$/ml, respectively, which is similar to titers attained with wild-type strains on sPER.C6 cells (Sanders, Edo-Matas et al. 2012).

Example 8

In Vitro Antigenic Content of CAVA-$PV_{Mahoney}$, CAVA-$PV_{MEF\text{-}1}$ and CAVA-$PV_{Saukett}$ in sPER.C6 Cells Compared to the Conventional IPV Strains Mahoney, MEF-1 and Saukett IPV dosing is based on D-antigen Units (DU), which is quantified by an in vitro D-Antigen ELISA (Beale 1961), performed as described in the European Pharmacopeia monograph 0214. For wild-type IPV, one dose of the vaccine is to contain 40, 8 and 32 DUs for the inactivated Mahoney, MEF-1 and Saukett viruses, respectively, corresponding to a dose that will induce a protective immune response in vaccine recipients (Grassly 2014). The D-antigen content and, therefore, indirectly the immunogenic potency, of the active CAVA-$PV_{Mahoney}$, CAVA-$PV_{MEF\text{-}1}$ and CAVA-$PV_{Saukett}$ viruses was quantified by D-antigen ELISA assay and compared to the conventional IPV strains, Mahoney, MEF-1 and Saukett. Infections were done in PER.C6® cells in suspension with a cell density of $10\times10^6$ cells/ml at an MOI of 1. Infection temperature was 30° C. for the CAVA-PV strains and 35° C. for the wild-type strains, as this is the production temperature for conventional IPV.

Table 3 shows the D-antigen values obtained for the viruses, expressed per milliliter of infection harvest (DU/ml) and per infectious unit (DU/$TCID_{50}$). Since the D-antigenicity per milliliter (DU/ml) is dependent on the concentration of virus present in the sample (Titer or $TCID_{50}$/ml), the specific antigenic content per infectious unit of the CAVA-PV strains versus the wild-type strains were calculated. This corresponds to a fair comparison of the strains. The specific antigenic content was similar for the CAVA-PV strains versus their wild-type counterparts, indicating that a similar immunogenic profile between CAVA-PV and their wild-type counterparts may be expected. As the viruses contain the same capsid sequences, the antigenicity is expected to be similar; this is corroborated by the D-antigen results obtained.

Example 9

Figure 14:
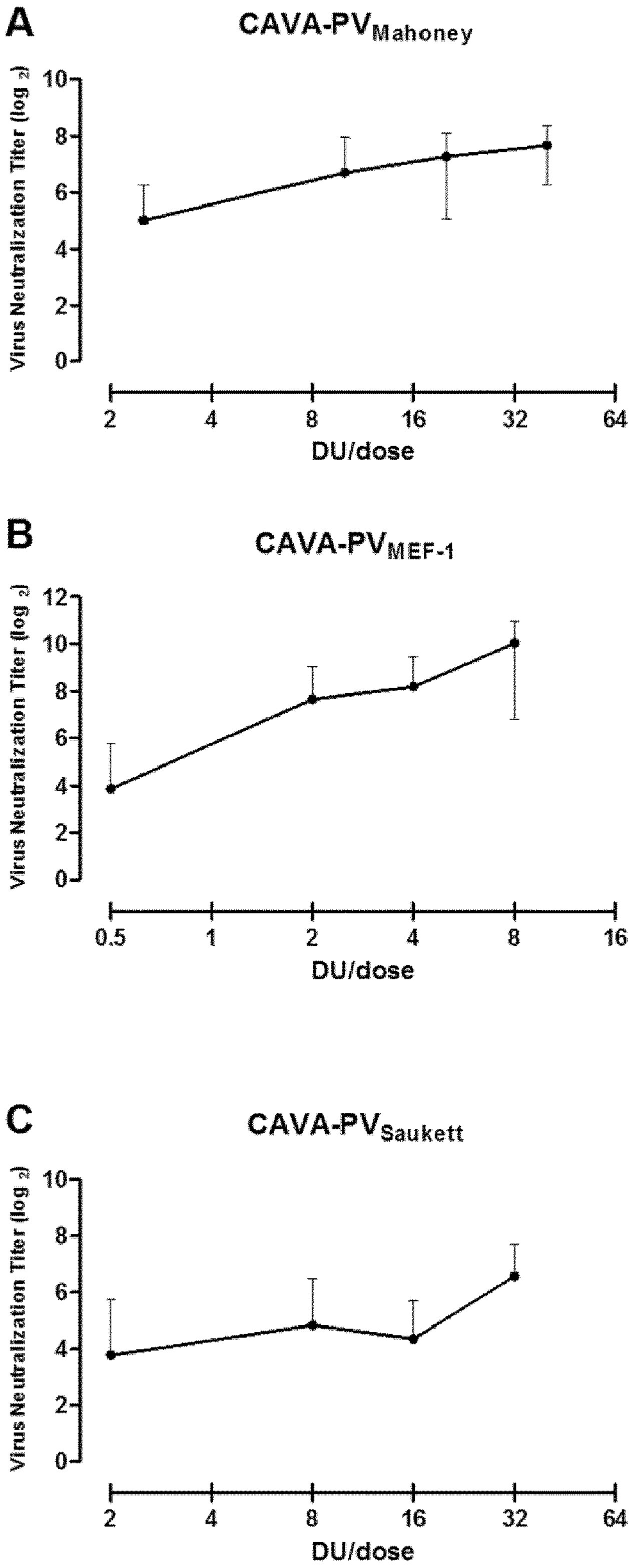
FIG. 14: Virus Neutralization Titers of rats immunized with inactivated CAVA-$PV_{Mahoney}$ (Panel A), CAVA-$PV_{MEF\text{-}1}$ (Panel B), or CAVA-$PV_{Saukett}$ (Panel C).

In Vivo Immunogenicity of Inactivated and Purified CAVA-PV$_{Mahoney}$, CAVA-PV$_{MEF-1}$ and CAVA-PV$_{Saukett}$ in Rats The CAVA vaccine strains, CAVA-PV$_{Mahoney}$, CAVA-PV$_{MEF-1}$ and CAVA-PV$_{Saukett}$, were purified and inactivated. Purification was performed by two subsequent chromatography steps using clarified crude harvest material from an infection under envisioned production conditions (2×250 ml in a roller bottle containing sPER.C6 cells with a cell density of 10×10$^6$ vc/ml in PERMEXCIS® medium, at an MOI of 1, at 30° C.). Cation Exchange Chromatography (CEX) was performed using Sartobind S cationic membranes, after which the eluted material was consequently used for Size Exclusion Chromatography step for further purification (polish) and buffer exchange. The SEC eluate was conditioned using M199 and glycine prior to inactivation. Inactivation was performed by addition of 0.009% formalin (or 3.3 mM formaldehyde) and incubated for 13 days at 37° C. Filtration was performed at days 6 and 13 of inactivation. The inactivated bulks were used for in vivo immunogenicity testing in rats. Four groups of Wistar female rats (n=10) were immunized with a dilution of 1:1 (full human dose), 1:2, 1:4 and 1:16 of each of the inactivated CAVA vaccine strains. The full human dose represents 40, 8 or 32 D-antigen units of Type 1, 2 and 3, respectively, which is the dosing of conventional IPV. Rats were left for 21 days, after which they were bled and sera was used for Virus Neutralization Assay using Sabin viruses as challenge viruses and Hep2C cells. FIG. 14 depicts the neutralizing antibody titers raised in rats after immunization with either inactivated CAVA-PV$_{Mahoney}$, CAVA-PV$_{MEF-1}$ or CAVA-PV$_{Saukett}$. All three vaccine strains showed to be immunogenic as they induced production of high titers of neutralizing antibodies in a dose-dependent fashion upon dilution of the full vaccine dose.

Example 10

Generation of an Additional CAVA-PV Strain

The 31 mutations that were derived from the three independent clones (see Example 1, Table 1) were analyzed for their conservation amongst a panel of PV strains. Fourteen mutations were identified that would likely play a significant role in providing the temperature-sensitive phenotype observed in CAVA-PV. These are depicted in Table 4. In this table, a single asterisk depicts mutations that are unique in CAVA-PV and where the nucleotides at those positions are conserved in all other PV strains used for the alignment, which were Brunenders, as well as Brunhilde, Mahoney, Sabin 1, Sabin 2, Sabin 3, MEF-1, and Saukett. A double asterisk in this table depicts mutations that are unique in CAVA-PV and where the nucleotides at those positions are conserved in all of the other Type 1 PV strains used for the alignment: Brunenders, Brunhilde, Mahoney and Sabin 1. The nucleotide mutation at position 4120 in CAVA-PV is shared with Sabin 1, but the nucleotide is conserved at that position in all of the other PV strains used for the alignment.

These 14 mutations were inserted as described in Table 4 into the parental sequence of Brunenders to determine the effects on temperature sensitivity. The virus was prepared as described in Example 1. Briefly; the recombinant cDNA plasmid containing the Brunenders genome with 14 mutations was synthesized. The resulting plasmid was subjected to in vitro transcription and subsequent RNA transfection. Replication kinetics was performed in PER.C6® cells by infecting cells at either 30° C. or 37° C. with an MOI of 1 and a cell density of 10×10$^6$ cells per ml in PERMEXCIS® medium supplemented with 4 mM L-Glutamine. Samples were taken at 0, 2, 8, 24 and 48 hours post-infection and subjected to titration.

Figure 15:
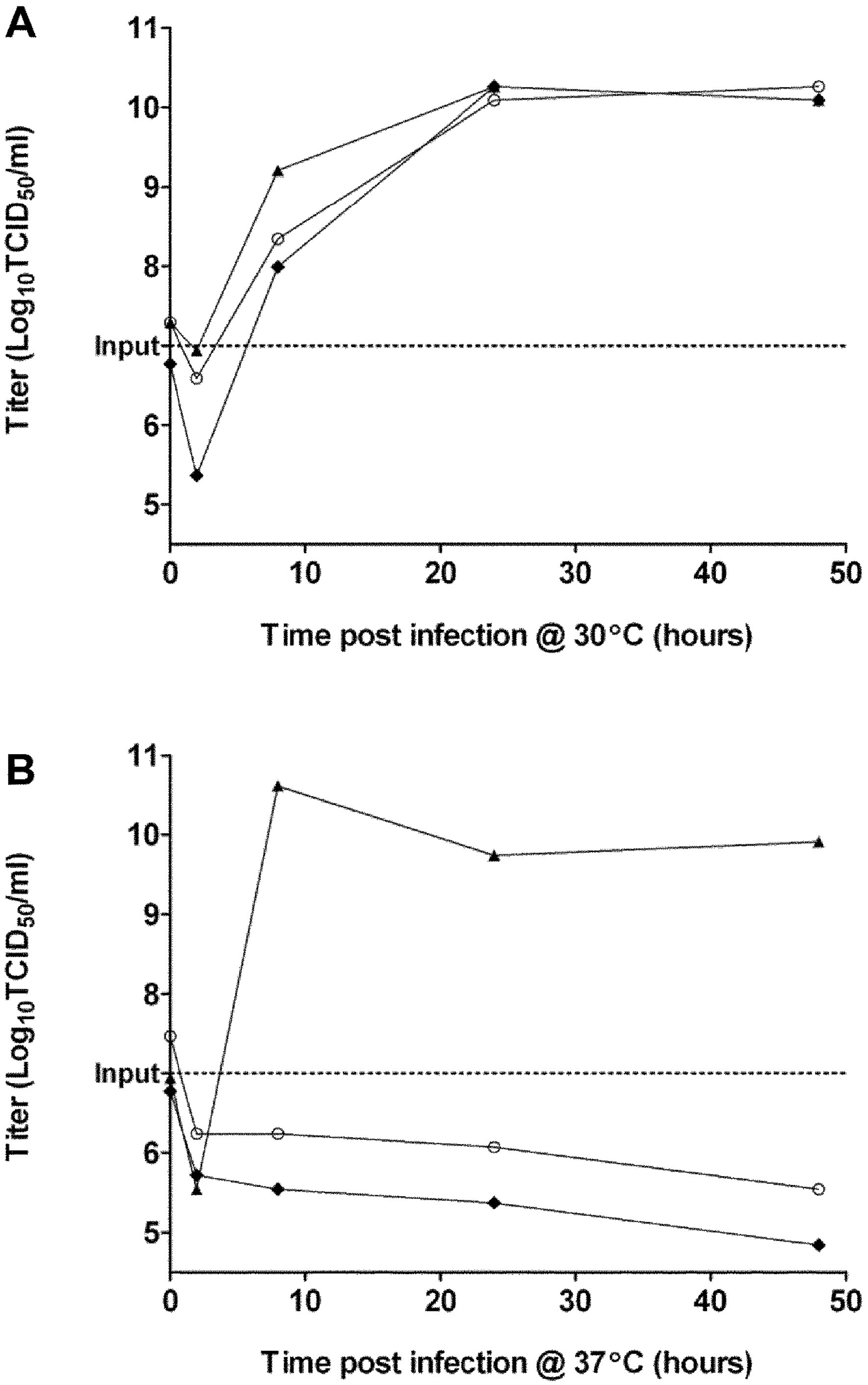
FIG. 15: Replication kinetics for parental Brunenders PV, CAVA-$PV_{Backbone}$ of Example 1 (having the 31 mutations of Table 1 compared to a Brunenders parental strain), and a further CAVA-PV of Example 10 (which corresponds to a parental Brunenders strain with the 14 mutations of Table 4). Panel A shows growth at 30° C. and Panel B shows growth at 37° C. Data for the parental Brunenders PV are shown as filled triangles, data for CAVA-$PV_{Backbone}$ of Example 1 are shown as open circles, and data for CAVA-PV of Example 10 are shown as filled diamonds.

FIG. 15 shows the growth curves of the new CAVA-PV strain with 14 mutations as described in this Example, and the CAVA-PV$_{Backbone}$ strain of Example 1 (having 31 mutations), as compared to their wild-type counterpart (Brunenders parental strain). The Brunenders parental strain shows growth curves as is expected from wild-type strains at both 37° C. and 30° C., reaching the plateau titer within 10 and 24 hours post-infection, respectively. Upon introducing the 14 mutations, the new CAVA-PV strain displays a growth phenotype similar to the CAVA-PV$_{Backbone}$ strain of Example 1 that had more than twice the amount (i.e., 31) of mutations compared to the parental strain. No replication is observed at 37° C., while at 30° C., the replication was comparable to wild-type.

These results show that the loss of fitness at physiological temperature can already be induced by these 14 mutations. Moreover, further to the various embodiments described above, this example provides yet another embodiment of a CAVA-PV strain according to the disclosure, i.e., a recombinant poliovirus strain that can be propagated in cell culture at 30° C. and that cannot be substantially propagated at 37° C.

Example 11

Generation of CAVA-PVs Strain from Different Parental Strains from Different Serotypes The previous examples all described the use of the Brunenders strain (a partially attenuated Type 1 PV strain) as the starting or parental strain for the generation of the various CAVA-PV strains. In this Example, two very dissimilar parental strains, namely the Type 2 neurovirulent, wild-type MEF-1 strain, and the Type 3 neuroattenuated Sabin 3 strains were used as a background (parental) strain. MEF-1 is routinely used as the Type 2 immunogen for conventional IPV preparations, while Sabin 3 is a component of OPV preparations.

Thirteen of the 14 mutations described in Table 4 with respect to the Brunenders strain were inserted at the corresponding nucleotide positions into the MEF-1 strain (SEQ ID NO:5; as the MEF-1 strain already contained an A at position 3481, this position was not mutated; hence the 13 instead of 14 mutations.) to determine the effects on temperature sensitivity. The same was performed using the Sabin 3 genomic sequence (SEQ ID NO:8, as the Sabin 3 strain already contained a G and an A at positions 163 and 3473, respectively, these nucleotides were not mutated, hence the 12 instead of 14 mutations; see Table 4 for detailed description of CAVA mutations per strain).

The MEF-1 and Sabin 3 viruses were prepared as described in Example 1. Briefly, the recombinant cDNA plasmids containing the MEF-1 and Sabin 3 genomes with 13 and 12 mutations were first synthesized. The resulting plasmids were subjected to in vitro transcription and subsequent RNA transfection. Replication kinetics was performed in PER.C6® cells by infecting cells at either 30° C. or 37° C. with an MOI of 1 and a cell density of 10×10$^6$ cells per ml in PERMEXCIS® medium supplemented with 4 mM L-Glutamine. Samples were taken at 0, 2, 8, 24 and 48 hours post-infection and subjected to titration.

Figure 16:
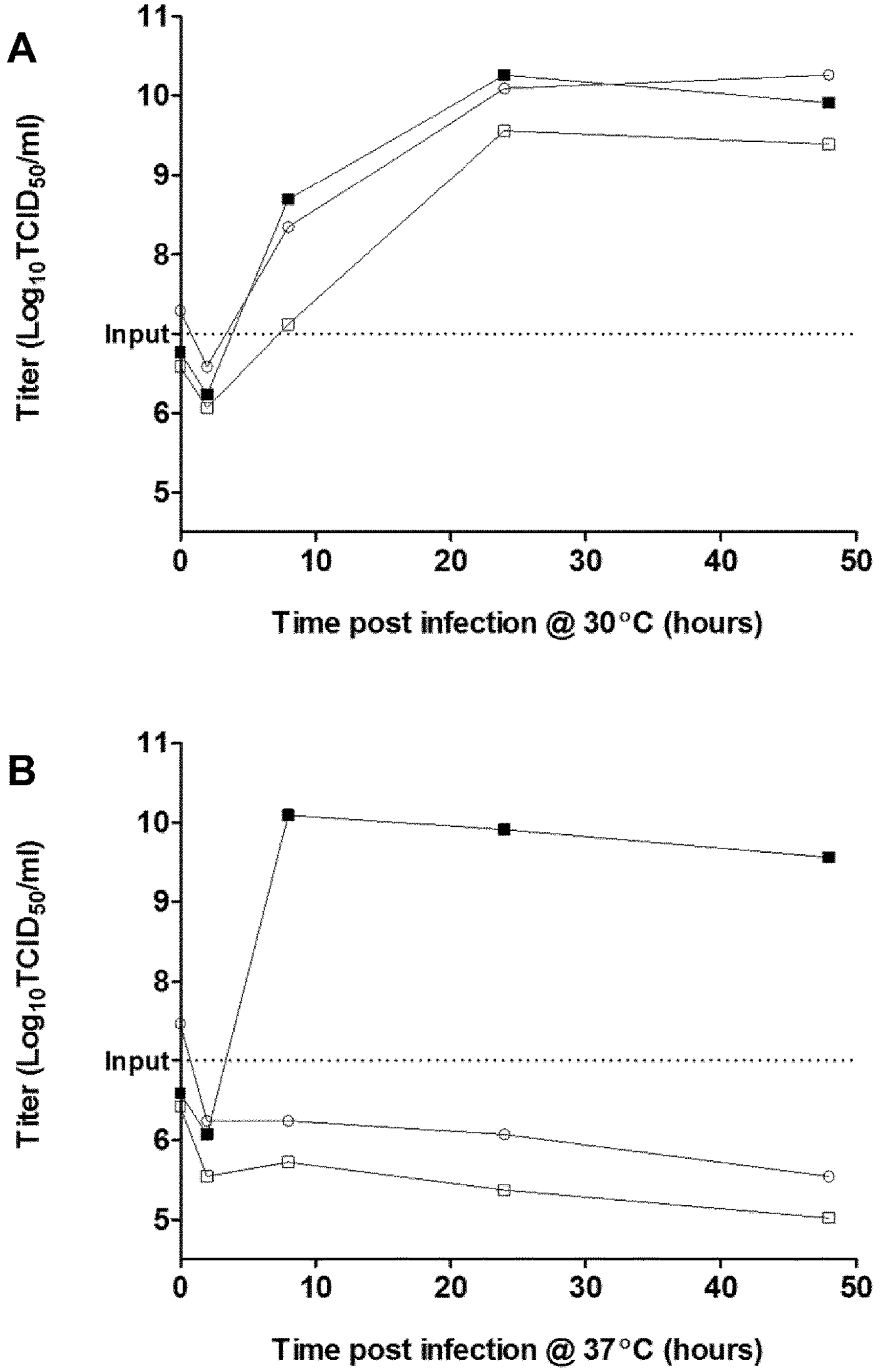
FIG. 16: Replication kinetics for parental wild-type MEF-1, CAVA-$PV_{Backbone}$ of Example 1 (having 31 mutations of Table 1 in a Brunenders background) and a further CAVA-PV strain of Example 11 (which corresponds to a parental MEF-1 PV with 13 mutations as indicated in Table 4). Panel A illustrates growth at 30° C. and Panel B shows growth at 37° C. Data for MEF-1 are shown as filled squares, data for CAVA-$PV_{Backbone}$ of Example 1 are shown as open circles, and data for MEF-1 with 13 CAVA mutations (CAVA-PV of Example 11) are shown as open squares.

FIG. 16 shows the growth curves of the new strain based on MEF-1 with 13 mutations as described in this Example, and the CAVA-PV$_{Backbone}$ strain of Example 1 (i.e., a Brunenders strain having 31 mutations), as compared to the wild-type MEF-1 strain. The MEF-1 parental strain shows growth curves as is expected from wild-type strains at both 37° C. and 30° C., reaching the plateau titer within 10 and 24 hours post-infection, respectively. Upon introducing the 13 mutations, the new MEF-1-based strain developed a growth phenotype similar to the CAVA-PV$_{Backbone}$ strain of Example 1 that was based on a Brunenders background strain and had more than twice the amount of mutations compared to its parental strain. No replication is observed at 37° C., while at 30° C., the replication was comparable to wild-type.

Figure 17:
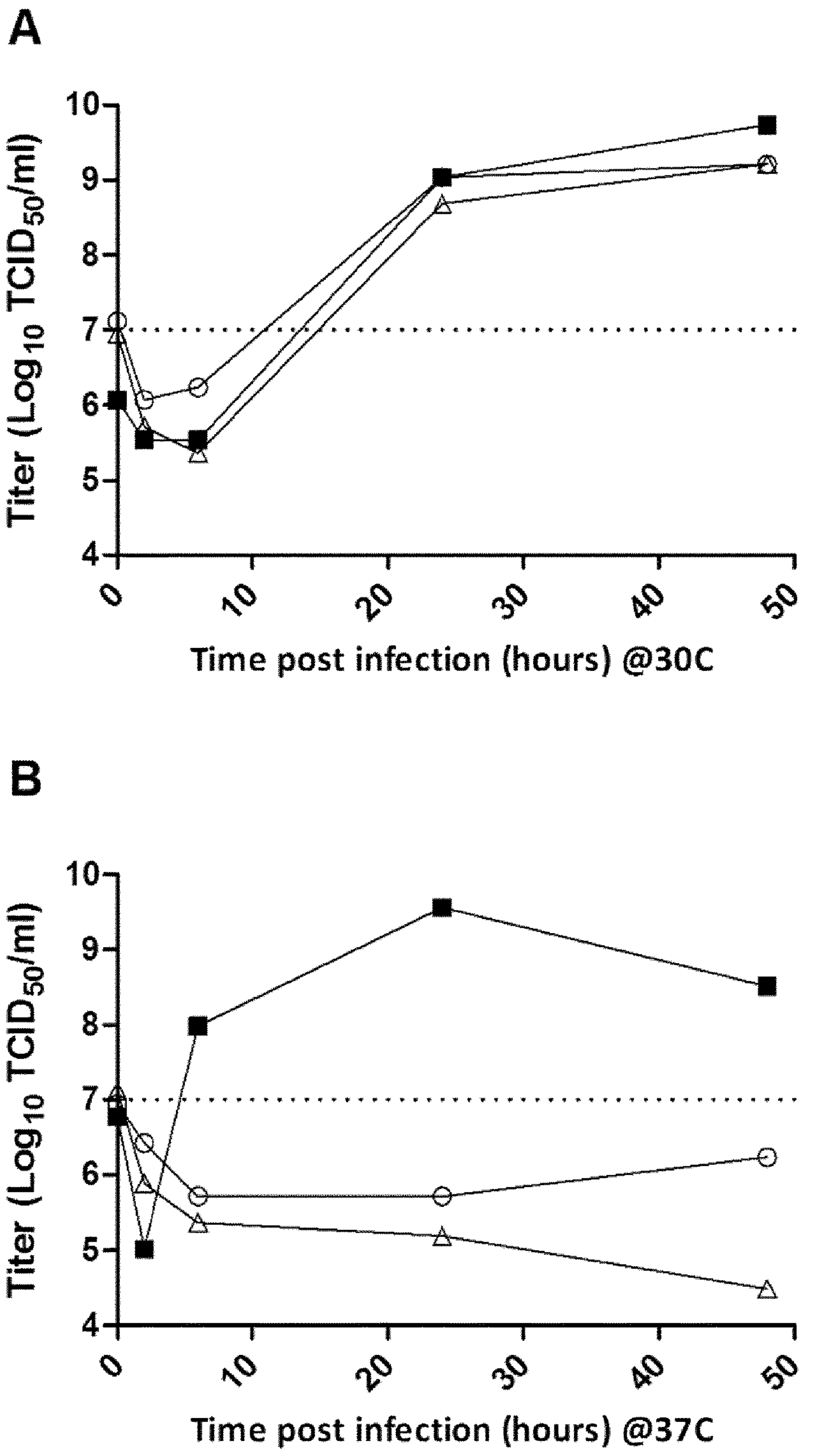
FIG. 17: Replication kinetics for parental Sabin 3, CAVA-$PV_{Backbone}$ of Example 1 (having 31 mutations of Table 1 in a Brunenders background) and a further CAVA-PV strain of Example 11 (which corresponds to a parental Sabin 3 PV with 12 mutations as indicated in Table 4). Panel A shows growth at 30° C. and Panel B illustrates growth at 37° C. Data for Sabin 3 are shown as filled squares, data for CAVA-$PV_{Backbone}$ of Example 1 are shown as open circles, and data for Sabin 3 with 12 CAVA mutations (CAVA-PV of Example 11) are shown as open triangles.

FIG. 17 shows the growth curves of the new strain based on Sabin 3 with 12 mutations described in this Example, as compared to the CAVA-PV$_{Backbone}$ of Example 1 (i.e., a Brunenders strain having 31 mutations), as compared to the attenuated Sabin 3 strain. The Sabin 3 OPV strain shows growth curves comparable to wild-type PV growth at both 37° C. and 30° C., reaching the plateau titer within 10 and 24 hours post-infection, respectively. Upon introduction of the 12 mutations, the new Sabin 3-based strain displayed a growth phenotype similar to the CAVA-PV$_{Backbone}$ strain of Example 1 that was based on a Brunenders background strain. No replication is observed at 37° C., while at 30° C., the replication was comparable to wild-type.

The data demonstrate that the new MEF-1 and Sabin 3 strains with 13 and 12 mutations, respectively, also have a CAVA-PV phenotype and is, thus, yet a further embodiment of a CAVA-PV strain according to the disclosure, i.e., a recombinant poliovirus strain that can be propagated in cell culture at 30° C. and that cannot be substantially propagated at 37° C. Therefore, in total, 14 mutations (of which 1 and 2 were already present in the new MEF-1 and Sabin 3 parental strains) are sufficient for conveying the CAVA-PV growth phenotype into a wild-type poliovirus strain. This example demonstrates yet an alternative way to create additional CAVA-PV strains, and it is shown that such strains can be prepared from different poliovirus parental strains. Notably, these data show that the parental strain neither needs to be a Type 1 PV strain, nor a wild-type or partially attenuated strain, since the parental strain for this example was a Type 2, neurovirulent and wild-type PV strain as well as a Type 3 attenuated strain. The new strain of this example has a MEF-1 wild-type capsid sequence, and can thus be used directly for generating a safe and effective IPV against Type 2 PVs. It can also be used as a starting point to swap this capsid for other wild-type capsids such as a Mahoney or a Saukett capsid. The skilled person will also appreciate that this example makes plausible that introduction of the 14 mutations (or a subset thereof) of Table 4 into the corresponding positions in the genome of a Mahoney, Saukett, Sabin 1 and Sabin 2 strains would result in further CAVA-PV strains that could be used as safe and effective vaccine strains for IPV production.

Example 12

Quantification of CAVA-PV Infection by EM

Figure 18:
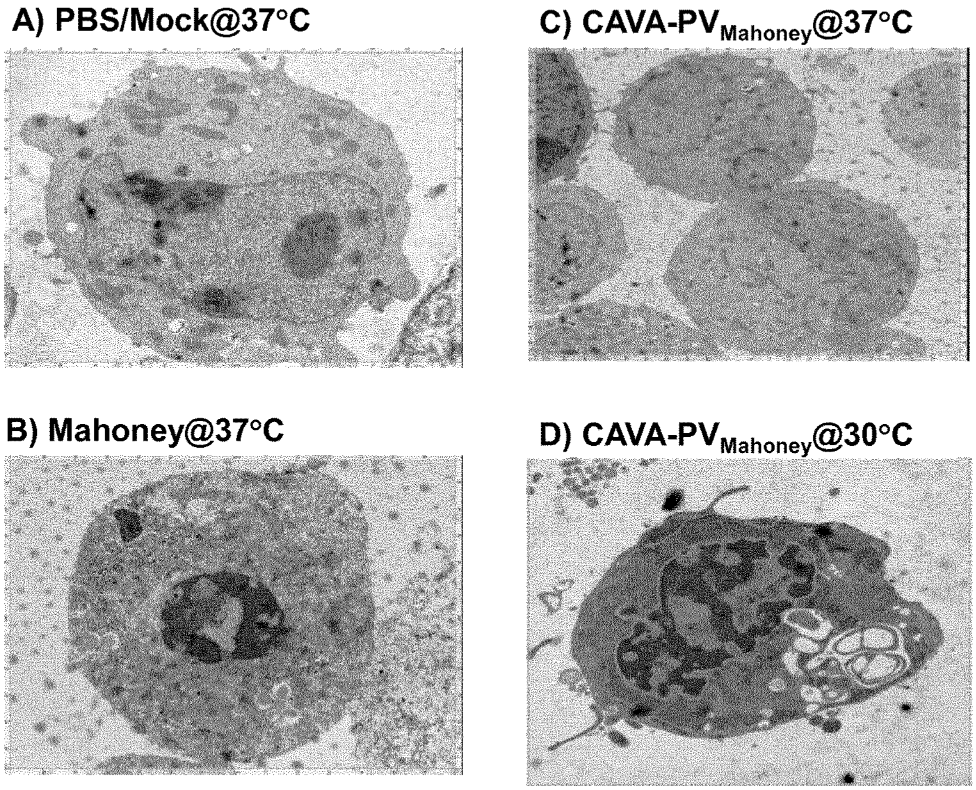
FIG. 18: EM micrographs of representative cells during infection with (Panel A) PBS (Mock) at 37° C., (Panel B)

Quantification of viral infection by titration ($TCID_{50}$) at 37° C. of CAVA-PV strains does not result in the observation of cytopathic effects (CPE), hence titration must be performed at 30° C. This is corroborated by the replication kinetic curves of the CAVA-PV strains demonstrating no increase in infectious units during infection at 37° C. (FIGS. 2-11, 13, 15-17). This indicates that the viruses are unable to replicate at this temperature. However, to further understand the block in replication at 37° C., Electron Microscopy (EM) was performed as an alternative method to characterize PV infection. FIG. 18 depicts results of the EM after infection of sPER.C6 cells with a cell density of $10\times10^6$ cells/ml with an MOI 1 at 30° C. and 37° C. using Mahoney, CAVA-PV$_{Mahoney}$ or PBS (mock-infected).

EM samples were fixed in 1.5% glutaraldehyde in 0.1 M cacodylate buffer (pH 7.4) and stained with 1% osmium tetroxide. The samples were then washed in 0.14 M cacodylate buffer and pelleted in 3% agar, after which the pellets were gradually dehydrated with an ethanol series. The samples were then infiltrated for one hour with a 1:1 mixture of propylene oxide and epoxy LX-112 resin (Ladd Research) and an additional hour in 100% epoxy LX-112, after which the samples were polymerized for 48 hours at 60° C. Cell sections of 50 nm thickness were cut, placed onto carbon-coated formvar grids, and counterstained with 7% uranyl acetate and lead citrate. A Tecnai 12 BioTwin transmission electron microscope (FEI company) operated at 120 kV was used for imaging.

The EM data in FIG. 18 depict representative cells from each infection. The cells infected with CAVA-PV$_{Mahoney}$ at 30° C. resembled those infected with the wild-type Mahoney strains, most cells were already dead and lysed or apoptotic. The apoptotic cells had shrunk in size and were very dark in color. These apoptotic cells contained rearrangements of ER membranes as well as virus-induced vesicle formation. When poliovirus concentrations are high in a cell, highly structured virus lattices can be formed, which were visible in the Mahoney and CAVA-PV$_{Mahoney}$ (at 30° C.) samples.

However, at 37° C., the CAVA-PV$_{Mahoney}$-infected cells did not show any of these features associated with PV infection. In fact, these cells showed to be healthy with no signs of infection in any of the cells in the samples. The CAVA-PV$_{Mahoney}$-infected cells that were incubated at 37° C. resembled the PBS mock-infected samples. The CAVA-PV$_{Mahoney}$ titer of this 37° C-incubated sample was measured to be 4.32 $TCID_{50}$/ml, which is less than the theoretical input (7.0 $TCID_{50}$/ml as calculated MOI of added volume of input virus of known titer), however, it confirms that CAVA-PV$_{Mahoney}$ virus had indeed been added to the infection without inducing any signs of infection.

Example 13

Quantification of CAVA-PV Infection by qPCR

The samples used for EM (Example 12) were subjected to quantitative PCR as to determine the levels of viral RNA during infection. Viral RNA was isolated from infection harvests using a QIAamp® viral RNA isolation kit after which the PowerSYBR Green RNA-to-Ct 1 step Kit was used for RT-qPCR, using primers binding to the 3D polymerase gene. FIG. 19 depicts vRNA levels, as observed by titration of infection harvests, the viral RNA levels decrease when CAVA-1 Mahoney infection is maintained at 37° C., however, this is not the case when infection temperatures are at 30° C., where an increase of vRNA is observed. It can, therefore, be concluded that there are defects in RNA replication, and it is likely that it is blocked completely at 37° C. The block in CAVA-PV replication, therefore, takes place at RNA replication level, or earlier in the infection cycle.

Example 14

Generation of PVs that Do Not Display the CAVA Phenotype

To further understand which mutations are involved in the CAVA-phenotype, new intermediate viruses were constructed using either the seven CAVA mutations in the 5'UTR or the 17 mutations in the non-structural proteins in the background of the parental Brunenders strain (SED ID NO:1, see Table 4 for the CAVA mutations in these two regions). The CAVA-PV strains of Example 6 has already demonstrated that the CAVA mutation in the capsid could be removed without effects on the CAVA phenotype; therefore, only the mutations in the 5'UTR and non-structural regions were examined here. The intermediate viruses were tested for replication kinetics at 30° C. and 37° C. as compared to the parental Brunenders strain, the CAVA-$PV_{Backbone}$ of Example 1 and CAVA-$PV_{Mahoney}$ of Example 6.

The intermediate viruses were prepared as described in Example 1. Briefly, the recombinant cDNA plasmids containing the Brunenders genomes with either seven CAVA mutations in the 5'UTR or 17 CAVA mutations in the non-structural proteins were first synthesized. The resulting plasmids were subjected to in vitro transcription and subsequent RNA transfection. Replication kinetics was performed in PER.C6® cells by infecting cells at either 30° C. or 37° C. with an MOI of 1 and a cell density of $10\times10^6$ cells per ml in PERMEXCIS® medium supplemented with 4 mM L-Glutamine. Samples were taken at 0, 2, 8, 24 and 48 hours post-infection and subjected to titration.

FIG. 20 shows the growth curves of the new strains based on the Brunenders parental strains with mutations as described in this Example, as well as the CAVA-$PV_{Backbone}$ strain of Example 1 (i.e., a Brunenders strain having 31 mutations), as compared to the wild-type Brunenders strain. The intermediate strains show impaired growth curves at 37° C., where replication is hampered as compared to the Brunenders parental strains, but not abolished as compared to the CAVA-$PV_{Backbone}$. Here, the intermediate viruses grow at a slower rate as compared to the Brunenders parental strain, as well as to lower maximum titers. At 30° C., the intermediate viruses show identical growth curves as compared to the Brunenders parental strain as well as the CAVA-$PV_{Backbone}$ and CAVA-$PV_{Mahoney}$ strains of Examples 1 and 6, respectively. The plateau titer was reached within 24 hours post-infection. Upon introducing the 5'UTR or non-structural mutations, the new strains did not have a phenotype identical to the CAVA-$PV_{Backbone}$ and CAVA-$PV_{Mahoney}$ strains; therefore, it can be concluded that the CAVA phenotype can only be induced when mutations from both regions (5'UTR and non-structural proteins) are combined into one parental genome.

TABLE 1

CAVA-PV with a total of 31 mutations, including seven mutations in the 5'UTR, seven mutations in the capsid, and 17 mutations in the non-structural proteins. The nucleotide positions described in Table 1 are referenced to the genome of a Brunenders strain; for other PVs, the exact nucleotide numbering may differ slightly.

7 mutations in 5'UTR

| Where | nt# | nt change |
|---|---|---|
| 5'UTR | 133 | A → G |
| 5'UTR | 142 | U → C |

TABLE 1-continued

CAVA-PV with a total of 31 mutations, including seven mutations in the 5'UTR, seven mutations in the capsid, and 17 mutations in the non-structural proteins. The nucleotide positions described in Table 1 are referenced to the genome of a Brunenders strain; for other PVs, the exact nucleotide numbering may differ slightly.

| | | |
|---|---|---|
| 5'UTR | 146 | G → A |
| 5'UTR | 163 | A → G |
| 5'UTR | 579 | G → A |
| 5'UTR | 597 | C → U |
| 5'UTR | 609 | G → A |

| nt# | Where | nt change | aa Change |
|---|---|---|---|
| 7 mutations in the capsid | | | |
| 805 | VP4 | A → C | Y→ S |
| 1787 | VP3 | C → U | silent |
| 1905 | VP3 | U → C | silent |
| 2756 | VP1 | U → C | silent |
| 3236 | VP1 | C → U | silent |
| 3323 | VP1 | C → U | silent |
| 3376 | VP1 | A → G | E → G |
| 17 mutations in the non-structural proteins | | | |
| 3476 | 2A | C → U | silent |
| 3486 | 2A | G → A | V → I |
| 3852 | 2B | A → U | I → F |
| 4120 | 2B | U → C | I → T |
| 4253 | 2C | C → U | silent |
| 4301 | 2C | U → C | silent |
| 4428 | 2C | A → G | I → V |
| 4563 | 2C | A → U | I → L |
| 4811 | 2C | A → G | silent |
| 5436 | 3A | G → A | V → M |
| 5705 | 3BC | A → G | silent |
| 6059 | 3D | C → U | silent |
| 6210 | 3D | A → G | M → V |
| 6488 | 3D | C → U | silent |
| 6848 | 3D | G → A | M → I |
| 7079 | 3D | U → C | silent |
| 7102 | 3D | U → C | V → A |

TABLE 2

Mouse model for in vivo neurovirulence in CD155 transgenic mice

| Virus | Route | (P)$LD_{50}$ ($TCID_{50}$) |
|---|---|---|
| CAVA-$PV_{Backbone}$ | i.c. | $>9\times10^7$ |
| | i.m. | $>10^8$ |
| | i.p. | $>10^8$ |
| CAVA-$PV_{Mahoney}$ | i.c. | $>2.4\times10^8$ |
| CAVA-$PV_{MEF\text{-}1}$ | i.c. | $>2.4\times10^8$ |
| CAVA-$PV_{Saukett}$ | i.c. | $>1.7\times10^8$ |
| Brunenders | i.c. | $1.5\times10^6$ |
| | i.m. | $3.2\times10^6$ |
| | i.p. | $1.7\times10^7$ |
| Brunhilde | i.c. | $4.2\times10^2$ |
| | i.m. | $2.4\times10^4$ |
| | i.p. | $6.9\times10^6$ |
| Mahoney | i.c. | $10^2$ |
| | i.m. | $1.6\times10^4$ |
| | i.p. | $5\times10^5$ |
| MEF-1 | i.c. | $3.2\times10^4$ |
| | i.m | $>10^8$ |
| | i.p | $>10^8$ |
| Saukett | i.c. | $7.0\times10^2$ |
| | i.m | $1.0\times10^6$ |
| | i.p | $2.3\times10^6$ |
| Sabin 1 | i.c. | $>2\times10^7$ |
| Sabin 2 | i.c. | $>10^8$ |
| Sabin 3 | i.c. | $>10^8$ |

TABLE 3

| Antigenic content of CAVA-$PV_{Mahoney}$, CAVA-$PV_{MEF-1}$ and CAVA-$PV_{Saukett}$ | | | | |
|---|---|---|---|---|
| | Poliovirus | DU/ml | Titer ($TCID_{50}$/ml) | DU/$TCID_{50}$ |
| Type I | CAVA-1-Mahoney | 2652 | 9.56 | $7.3 \times 10^{-07}$ |
| | Mahoney | 3288 | 10.09 | $2.7 \times 10^{-07}$ |
| Type II | CAVA-2 MEF-1 | 705 | 9.91 | $8.7 \times 10^{-08}$ |
| | MEF-1 | 501 | 10 | $5.0 \times 10^{-08}$ |
| Type III | CAVA-3 Saukett | 866 | 9.56 | $2.4 \times 10^{-07}$ |
| | Saukett | 1334 | 9.56 | $3.7 \times 10^{-07}$ |

TABLE 4

| 14 mutations for temperature sensitivity of some CAVA-PV strains (e.g., Examples 10 and 11). Nucleotide position in respective PV genome | | | | | | | | |
|---|---|---|---|---|---|---|---|---|
| Where | Brunenders | MEF-1 | Mahoney | Saukett | Sabin 1 | Sabin 2 | Sabin 3 | nt change |
| 5 mutations in 5'UTR | | | | | | | | |
| IRES Domain II | 133 | 134 | 131 | 133 | 131 | 131 | 133 | A → G* |
| IRES Domain II | 142 | 143 | 140 | 142 | 140 | 140 | 142 | U → C* |
| IRES Domain II | 163 | 164 | 161 | 163 | 161 | 161 | $163^{b}$ | A → G** |
| IRES Domain VI | 587 | 589 | 593 | 596 | 593 | 594 | 596 | C → U* |
| IRES Domain VI | 609 | 610 | 605 | 608 | 605 | 606 | 608 | G → A* |
| 9 mutations in the non-structural proteins | | | | | | | | |
| 2A | 3486 | $3481^{a}$ | 3482 | $3473^{a}$ | 3482 | 3481 | $3473^{a}$ | G → A**$^{a}$ |
| 2B | 3852 | 3847 | 3848 | 3839 | 3848 | 3847 | 3839 | A → U* |
| 2B | 4120 | 4115 | 4116 | 4107 | $4116^{c}$ | 4115 | 4107 | U → C |
| 2C | 4428 | 4423 | 4424 | 4415 | 4424 | 4423 | 4415 | A → G* |
| 2C | 4563 | 4558 | 4559 | 4550 | 4559 | 4558 | 4550 | A → U* |
| 3A | 5436 | 5431 | 5432 | 5423 | 5432 | 5431 | 5423 | G → A* |
| 3D | 6210 | 6205 | 6206 | 6197 | 6206 | 6205 | 6197 | A → G* |
| 3D | 6848 | 6843 | 6844 | 6835 | 6844 | 6843 | 6835 | G → A* |
| 3D | 7102 | 7097 | 7098 | 7089 | 7098 | 7097 | 7089 | U → C* |

*mutations that are unique in CAVA-PV and the parental Brunenders nucleotides at those positions are conserved in all other PV strains used for the alignment.

**mutations that are unique in CAVA-PV and the parental Brunenders nucleotides at those positions are conserved in all of the other PV1 strains used for the alignment. Representative parent strain genome sequences are provided as SEQ ID NO: 1 (Brunenders), SEQ ID NO: 5 (MEF-1), SEQ ID NO: 6 (Mahoney), SEQ ID NO: 7 (Saukett), SEQ ID NO: 8 (Sabin 3), SEQ ID NO: 9 (Sabin 1) and SEQ ID NO: 10 (Sabin 2). All the nucleotide changes as described are identical for all strains and corresponding positions, with the exception of: mutation in the sequence encoding 2A protein, which is already an adenine in MEF-1, Saukett and Sabin 3 strains at positions 3481 and 3473, respectively, annotated as "$^{a}$" in the table. Mutation in IRES Domain II is already an guanine in Sabin 3 at position 163, annotated as "$^{b}$" in the table. Mutation at position 4120 in the 2B protein in Sabin 1 was already a "$^{c}$" in this position.

BIBLIOGRAPHY

US Patent Documents

U.S. Pat. No. 8,546,123 (Oct. 1, 2013). "Production of poliovirus at high titers for vaccine production." Lewis.

U.S. Pat. No. 4,525,349 (Jun. 25, 1985). "Process for the large-scale production of a vaccine against poliomyelitis and the resulting vaccine." Montagnon and Fanget.

Foreign Patent Documents

WO 2007/007344 (Jan. 18, 2007). "Inactivated Poliomyelitis Vaccine Derived From Sabin Strain Of Polio Virus." Jain, Chawla, and Kumraj.

Other References

Beale, A. J. (1961). "The D-antigen content in poliovaccine as a measure of potency." *Lancet* 2(7213): 1166-1168.

Bouchard, M. J., D. H. Lam and V. R. Racaniello (1995). "Determinants of attenuation and temperature sensitivity in the type 1 poliovirus Sabin vaccine." *J. Virol.* 69(8):4972-4978.

Enders, J. F., T. H. Weller, and F. C. Robbins (1952). "Alteration in pathogenicity for monkeys of Brunhilde strain of poliomyelitis virus following cultivation in human tissues." *Fed. Proc.* 11:467.

Grassly, N. C. (2014). "Immunogenicity and Effectiveness of Routine Immunization With 1 or 2 Doses of Inactivated Poliovirus Vaccine: Systematic Review and Meta-analysis." *J. Infect. Dis.*

Hawken, J. and S. B. Troy (2012). "Adjuvants and inactivated polio vaccine: a systematic review." *Vaccine* 30(49): 6971-6979.

Heinsbroek, E. and E. J. Ruitenberg (2010). "The global introduction of inactivated polio vaccine can circumvent the oral polio vaccine paradox." *Vaccine* 28(22):3778-3783.

Henderson, D. A., J. J. Witte, L. Morris and A. D. Langmuir (1964). "Paralytic Disease Associated with Oral Polio Vaccines." *Jama.* 190:41-48.

Jahan, N., E. Wimmer and S. Mueller (2011). "A host-specific, temperature-sensitive translation defect determines the attenuation phenotype of a human rhinovirus/poliovirus chimera, PV1(RIPO)." *J. Virol.* 85(14):7225-7235.

Jiang, S. D., D. Pye and J. C. Cox (1986). "Inactivation of poliovirus with beta-propiolactone." *J. Biol. Stand.* 14(2): 103-109.

John, J. (2009). "Role of injectable and oral polio vaccines in polio eradication." *Expert Rev Vaccines* 8(1):5-8.

John, T. J. (2004). "A developing country perspective on vaccine-associated paralytic poliomyelitis." *Bull. World Health Organ.* 82(1):53-57; discussion 57-58.

Koike, S., C. Taya, T. Kurata, S. Abe, I. Ise, H. Yonekawa and A. Nomoto (1991). "Transgenic mice susceptible to poliovirus." *Proc. Natl. Acad. Sci. U.S.A.* 88(3):951-955.

Liao, G., R. Li, C. Li, M. Sun, Y. Li, J. Chu, S. Jiang and Q. Li (2012). "Safety and immunogenicity of inactivated poliovirus vaccine made from Sabin strains: a phase II, randomized, positive-controlled trial." *J. Infect. Dis.* 205(2): 237-243.

Mahmood, K., S. Pelkowski, D. Atherly, R. Sitrin and J. J. Donnelly (2013). "Hexavalent IPV-based combination vaccines for public-sector markets of low-resource countries: A product review." *Hum. Vaccin. Immunother.* 9(9).

Minor, P. D. (1999). "Poliovirus vaccination: current understanding of poliovirus interactions in humans and implications for the eradication of poliomyelitis." *Expert Rev. Mol. Med.* 1999:1-17.

Montagnon, B. J., B. Fanget and J. C. Vincent-Falquet (1984). "Industrial-scale production of inactivated poliovirus vaccine prepared by culture of Vero cells on microcarrier." *Rev. Infect. Dis.* 6 Suppl. 2:S341-344.

Okada, K., C. Miyazaki, Y. Kino, T. Ozaki, M. Hirose and K. Ueda (2013). "Phase II and III Clinical Studies of Diphtheria-Tetanus-Acellular Pertussis Vaccine Containing Inactivated Polio Vaccine Derived from Sabin Strains (DTaP-sIPV)." *J. Infect. Dis.* 208(2):275-283.

Pfeiffer, J. K. (2010). "Innate host barriers to viral trafficking and population diversity: lessons learned from poliovirus." *Adv. Virus Res.* 77:85-118.

Racaniello, V. R. (2006). "One hundred years of poliovirus pathogenesis." *Virology* 344(1):9-16.

Resik, S., A. Tejeda, R. W. Sutter, M. Diaz, L. Sarmiento, N. Alemani, G. Garcia, M. Fonseca, L. H. Hung, A. L. Kahn, A. Burton, J. M. Landaverde and R. B. Aylward (2013). "Priming after a fractional dose of inactivated poliovirus vaccine." *N. Engl. J. Med.* 368(5):416-424.

Sabin, A. B. (1956). "Present status of attenuated live-virus poliomyelitis vaccine." *J. Am. Med. Assoc.* 162(18): 1589-1596.

Sabin, A. B. B., L. R. (1973). "History of Sabin attenuated poliovirus oral live vaccine strains." *Journal of Biological Standardization* 1:115-118.

Salk, J. E. (1953). "Studies in human subjects on active immunization against poliomyelitis. I. A preliminary report of experiments in progress." *J. Am. Med. Assoc.* 151(13): 1081-1098.

Sanders, B. P., D. Edo-Matas, J. H. Custers, M. H. Koldijk, V. Klaren, M. Turk, A. Luitjens, W. A. Bakker, F. Uytdehaag, J. Goudsmit, J. A. Lewis and H. Schuitemaker (2012). "PER.C6® cells as a serum-free suspension cell platform for the production of high titer poliovirus: a potential low cost of goods option for world supply of inactivated poliovirus vaccine." *Vaccine* 31(5):850-856.

Sanders, B. P., Y. Liu, A. Brandjes, V. van Hoek, I. de Los Rios Oakes, J. Lewis, E. Wimmer, J. H. Custers, H. Schuitemaker, J. Cello and D. Edo-Matas (2015). "Brunenders: A partially attenuated historic poliovirus Type I vaccine strain." *J. Gen. Virol.*

Skern, T. and H. D. Liebig (1994). "Picornains 2A and 3C." *Methods Enzymol.* 244:583-595.

Toyoda, H., M. Kohara, Y. Kataoka, T. Suganuma, T. Omata, N. Imura and A. Nomoto (1984). "Complete nucleotide sequences of all three poliovirus serotype genomes. Implication for genetic relationship, gene function and antigenic determinants." *J. Mol. Biol.* 174(4): 561-585.

van der Werf, S., J. Bradley, E. Wimmer, F. W. Studier and J. J. Dunn (1986). "Synthesis of infectious poliovirus RNA by purified T7 RNA polymerase." *Proc. Natl. Acad. Sci. U.S.A.* 83(8):2330-2334.

van Wezel, A. L., G. van Steenis, C. A. Hannik and H. Cohen (1978). "New approach to the production of concentrated and purified inactivated polio and rabies tissue culture vaccines." *Dev. Biol. Stand.* 41:159-168.

Verdijk, P., N. Y. Rots and W. A. Bakker (2011). "Clinical development of a novel inactivated poliomyelitis vaccine based on attenuated Sabin poliovirus strains." *Expert Rev. Vaccines* 10(5):635-644.

Westdijk, J., D. Brugmans, J. Martin, A. van't Oever, W. A. Bakker, L. Levels and G. Kersten (2011). "Characterization and standardization of Sabin based inactivated polio vaccine: proposal for a new antigen unit for inactivated polio vaccines." *Vaccine* 29(18):3390-3397.

WHO (1988). Polio eradication by the year 2000. *Rep. Resolution* 41.28. W. H. Assembly. Geneva, WHO.

WHO (2005). Cessation of routine oral polio vaccine use after global polio eradication. Framework for National Policy Makers in OPV-Using Countries. Geneva, WHO.

WHO (2006). "Inactivated poliovirus vaccine following oral poliovirus vaccine cessation." *Wkly. Epidemiol. Rec.* 81(15): 137-144.

WHO (2009). WHO global action plan to minimize poliovirus facility-associated risk after eradication of wild polioviruses and cessation of routine OPV use. Geneva, WHO.

Zehrung, D. (2010). Improving the affordability of inactivated poliovirus vaccines (IPV) for use in low- and middle-income countries. *An economic analysis of strategies to reduce the cost of routine IPV immunization* PATH.

The invention claimed is:

1. A recombinant attenuated temperature sensitive poliovirus strain that can be propagated in cell culture at 30° C. and that cannot be propagated to more than a 5% increase in the number of infectious units for the virus in cell culture at 37° C., comprising a capsid from a Mahoney, MEF-1, or Saukett strain, wherein the genome of the recombinant attenuated poliovirus strain comprises mutations corresponding to the following positions as compared to the genome of the Brunenders strain (SEQ ID NO:1): 133 (A), 142 (U), 163 (A), 597 (C), and 609 (G) in the 5'UTR; and 3486 (G), 3852 (A), 4120 (U), 4428 (A), 4563 (A), 5436 (G), 6210 (A), 6848 (G), and 7102 (U) in the non-structural proteins.

2. A recombinant attenuated temperature-sensitive poliovirus type 1strain that can be propagated in cell culture at 30° C. and cannot be propagated to more than a 5% increase in the number of infectious units for the virus in cell culture at 37° C. wherein the genome of the recombinant attenuated poliovirus strain comprises mutations corresponding to the following positions as compared to the genome of the Mahoney strain (SEQ ID NO: 6): 131 (A to G), 140 (U to C), 161 (A to G), 593 (C to U), and 605 (G to A) in the 5'UTR; and 3482 (G to A), 3848 (A to U), 4116 (U to C), 4424 (A to G), 4559 (A to U), 5432 (G to A), 6206 (A to G), 6844 (G to A), and 7098 (U to C) in the non-structural proteins.

3. The recombinant attenuated temperature-sensitive poliovirus type 2strain that can be propagated in cell culture at 30° C. and cannot be propagated to more than a 5% increase in the number of infectious units for the virus in cell culture at 37° C., wherein the genome of the recombinant attenuated poliovirus strain comprises mutations corresponding to the following positions as compared to the genome of a MEF-1 strain (SEQ ID NO: 5): 134 (A to G), 143 (U to C), 164 (A to G), 598 (C to U), and 610 (G to A) in the 5'UTR; and 3481 (A to A), 3847 (A to U), 4115 (U to C), 4423 (A to G), 4558 (A to U), 5431 (G to A), 6205 (A to G), 6843 (G to A), and 7097 (U to C) in the non-structural proteins.

4. The recombinant attenuated temperature-sensitive poliovirus type 3strain that can be propagated in cell culture at 30° C. and cannot be propagated to more than a 5% increase in the number of infectious units for the virus in cell culture at 37° C., wherein the genome of the recombinant attenuated poliovirus strain comprises mutations corresponding to the following positions as compared to the genome of a Saukett strain (SEQ ID NO: 7): 133 (A to G), 142 (U to C), 163 (A to G), 596 (C to U), and 608 (G to A) in the 5'UTR; and 3472 (A to A), 3839 (A to U), 4107 (U to C), 4415 (A to G), 4550 (A to U), 5423 (G to A), 6197 (A to G), 6835 (G to A), and 7089 (U to C) in the non-structural proteins.

5. A composition comprising:

the poliovirus strain of claim 1; and a pharmaceutically acceptable carrier and/or excipient.

6. A composition comprising first, second and third recombinant poliovirus strains, wherein each of the first, second and third recombinant poliovirus strains can be propagated in cell culture at 30° C. but cannot be substantially propagated in cell culture at 37° C., and wherein the first recombinant poliovirus strain comprises a capsid from a Mahoney strain, wherein the second recombinant poliovirus strain comprises a capsid from a MEF-1 strain, and wherein the third recombinant poliovirus strain comprises a capsid from a Saukett strain.

7. The composition according to claim 6, further comprising a pharmaceutically acceptable carrier and/or excipient.

8. An inactivated poliovirus vaccine (IPV) composition, comprising:

the composition of claim 5, wherein the polioviruses in the composition are inactivated.

9. A combination vaccine composition comprising:

the IPV composition according to claim 8, and at least one antigen selected from the group consisting of diphtheria, tetanus, pertussis, *Haemophilus influenzae* type b (Hib), and Hepatitis B virus (HBV).

10. A method for vaccinating against poliomyelitis, the method comprising administering to a subject the composition according to claim 8.

11. A recombinant nucleic acid molecule comprising a polynucleotide that codes for the genome or the complement of the genome of the poliovirus strain of claim 1.

12. A method for preparing a preparation, the method comprising:

infecting at least one cell in a cell culture with the recombinant poliovirus strain of claim 1;

culturing the thus infected cells in the cell culture to propagate the poliovirus; and isolating the poliovirus from the cells or from the cell culture to obtain the preparation.

13. A method according to claim 12, further comprising inactivating the poliovirus.

14. The method according to claim 13, further comprising:

formulating the inactivated poliovirus into a pharmaceutical composition so as to form an inactivated poliovirus vaccine (IPV).

15. A method for obtaining a recombinant attenuated poliovirus strain that can be propagated in cell culture at 30° C., but cannot be substantially propagated in cell culture at 37° the method comprising:

passaging a parental poliovirus strain at 30° C. or less for sufficient passages to produce a virus with impaired growth at 37° C.;

isolating two or more different temperature-sensitive clones that display impaired growth at 37° C.;

sequencing the genomes of the temperature-sensitive clones;

identifying mutations in the sequences of the genomes of temperature-sensitive clones by comparing the sequences of the temperature-sensitive clones to the sequence of the parental poliovirus strain;

synthesizing the recombinant attenuated poliovirus strain by combining mutations from two or more different temperature-sensitive clones into the genome of a poliovirus strain; and rescuing the recombinant attenuated poliovirus strain that can be propagated in cell culture at 30° C. and that cannot be substantially propagated in cell culture at 37° C.

16. A method according to claim 15, farther comprising:

replacing the sequence coding for the capsid from the rescued recombinant attenuated poliovirus strain with a sequence coding for a capsid from a different poliovirus strain.

17. A method according to claim 15, further comprising:

replacing the sequence coding for the capsid from the rescued recombinant attenuated. poliovirus strain with a sequence coding for a capsid from a Mahoney, MEF-1, or Saukert strain.

18. A recombinant attenuated poliovirus strain produced by the method of claim 15.

19. The recombinant attenuated temperature-sensitive poliovirus type 1strain that can be propagated in cell culture at 30° C. and cannot be propagated to more than a 5% increase in the number of infectious units for the virus in cell culture at 37° C., wherein the genome of the recombinant attenuated poliovirus strain comprises mutations corresponding to the following positions as compared to the genome of a Sabin 1 strain (SEQ ID NO: 9): 131 (A to G), 140 (U to C), 161 (A to G), 593 (C to U), and 605 (G to A) in the 5'UTR; and 3482 (G to A). 3848 (A to U), 4116 (C to C), 4424 (A to G), 4559 (A to U), 5432 (G to A), 6206 (A to G), 6844 (G to A), and 7098 (U to C) in the non-structural proteins.

20. The method according to claim 16, further comprising:

replacing the polynucleotide encoding the capsid from the rescued recombinant attenuated poliovirus strain with a polynucleotide encoding a capsid from a Mahoney, MEF-1, or Saukett strain.

21. A recombinant attenuated temperature sensitive poliovirus type 2 strain that can be propagated in cell culture at 30° C. and cannot be propagated to more than a 5% increase in the number of infectious units for the virus in cell culture at 37° C., wherein the genome of the recombinant attenuated poliovirus strain comprises mutations corresponding to the following positions as compared to the genome of a Sabin 2 strain (SEQ ID NO: 10): 131 (A to G), 140 (U to C), 161 (A to G), 594 (C to U), and 606 (G to A) in the 5'UTR; and 3481 (G to A), 3847 (A to U), 4115 (U to C), 4424 (A to G), 4559 (A to U), 5432 (G to A), 6206 (A to G), 6844 (G to A), and 7098(U to C) in the non-structural proteins.

22. A recombinant attenuated temperature sensitive poliovirus type 3 strain that can be propagated in cell culture at 30° C. and cannot be propagated to more than a 5% increase in the number of infectious units for the virus in cell culture at 37° C., wherein the genome of the recombinant attenuated poliovirus strain comprises mutations corresponding to the following positions as compared to the genome of a Sabin 3 strain (SEQ ID NO: 8): 133 (A to G), 142 (U to C), 163 (G to G), 596 (C to U), and 608 (G to A) in the 5'UTR; and 3473 (A to A), 3839 (A to U), 4107 (U to C), 4415 (A to G), 4550 (A to U), 5423 (G to A), 6197 (A to G), 6835 (G to A), and 7089(U to C) in the non-structural proteins.

* * * * *